US012584125B2

(12) United States Patent (10) Patent No.: US 12,584,125 B2

Yeo et al. (45) Date of Patent: Mar. 24, 2026

(54) METHODS AND USE OF CHIMERIC PROTEINS

(71) Applicant: The Regents of the University of California, Oakland, CA (US)

(72) Inventors: Eugene Yeo, La Jolla, CA (US); Kristopher W. Brannan, Missouri City, TX (US); Ryan Marina, Boston, MA (US); Isaac A. Chaim, San Diego, CA (US); Daniel A. Lorenz, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 752 days.

(21) Appl. No.: 17/910,967

(22) PCT Filed: Mar. 12, 2021

(86) PCT No.: PCT/US2021/022150
§ 371 (c)(1),
(2) Date: Sep. 12, 2022

(87) PCT Pub. No.: WO2021/183914
PCT Pub. Date: Sep. 16, 2021

(65) Prior Publication Data

US 2023/0138328 A1 May 4, 2023

Related U.S. Application Data

(60) Provisional application No. 62/988,722, filed on Mar. 12, 2020.

(51) Int. Cl.
*C12N 15/10* (2006.01)
*C12Q 1/6869* (2018.01)

(52) U.S. Cl.
CPC ....... *C12N 15/1062* (2013.01); *C12Q 1/6869* (2013.01); *C12Q 2600/158* (2013.01)

(58) Field of Classification Search
None
See application file for complete search history.

(56) References Cited

U.S. PATENT DOCUMENTS

2011/0314565 A1 12/2011 Heintz et al.

FOREIGN PATENT DOCUMENTS

WO WO 2018/017144 1/2018
WO WO 2020/047498 3/2020

OTHER PUBLICATIONS

International Preliminary Report on Patentability in International Appln. No. PCT/US2021/022150, mailed on Sep. 22, 2022, 8 pages.
International Search Report and Written Opinion in International Appln. No. PCT/US2021/022150, mailed on Jun. 9, 2021, 10 pages.
Michel et al. "Ribosome profiling: a Hi-Def monitor for protein synthesis at the genome-wide scale." Wiley Interdisciplinary Reviews: RNA. Sep. 2013, 4(5):18 pages.

*Primary Examiner* — Michail A Belyavskyi
(74) *Attorney, Agent, or Firm* — Fish & Richardson P.C.

(57) ABSTRACT

Provided are methods for using chimeric proteins to produce RNA modifications that can be detected by sequencing methods, including methods detecting relative translation rates of various mRNAs. Also provided herein are compositions comprising chimeric proteins, wherein the chimeric proteins comprise a RNA editing protein and a ribosomal protein.

12 Claims, 38 Drawing Sheets

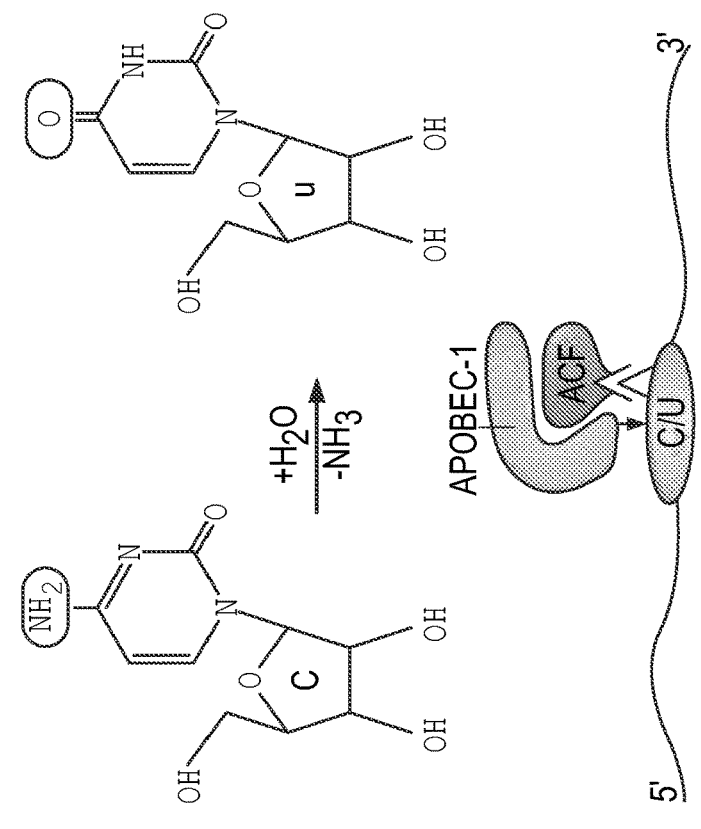
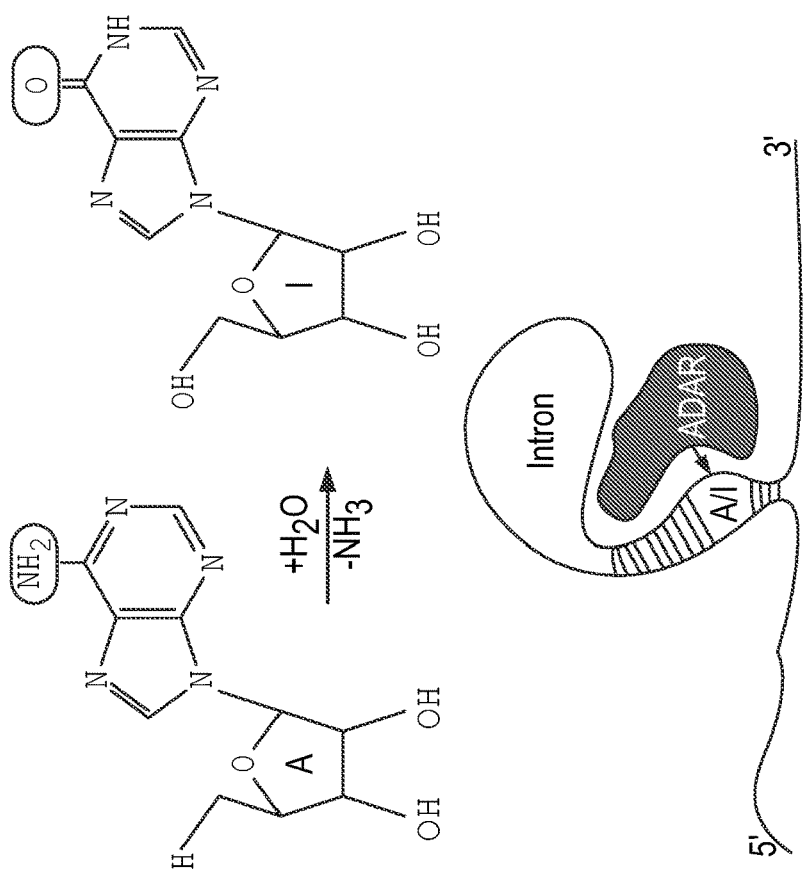
FIG. 1

| | RBFOX2-STAMP | | control-STAMP | |
|---|---|---|---|---|
| | sites | edit-clusters | sites | edit-clusters |
| raw STAMP edits | 389,322 | 92,793 | 63,968 | 51,020 |
| Poisson-based threshold | 56,706 | 29,570 | 37,651 | 33,966 |
| confidence score threshold | 27,481 | 11,136 | 559 | 531 |
| isolated site removal | 21,389 | 5,044 | 49 | 21 | distal STAMP edit-clusters (n=1163) on eCLIP target genes

N-terminal fusion RBFOX2-STAMP-edit clusters (n=8370) compared to RBFOX2-APOBEC1 (N-terminal) eCLIP RBFOX2-STAMP-no dox All
p=1e-04

RBFOX2-STAMP-low

All
p=1e-68

RBFOX2-STAMP-high

All
p=1e-131

TIA1-STAMP

SLBP-STAMP fraction of eCLIP peaks eCLIP peaks
shuffled regions score threshold 0.0    0.5    0.75    0.0    0.5    0.75 no filter          filter

TIA1-STAMP fraction of eCLIP peaks eCLIP peaks
shuffled regions score threshold 0.0    0.75    0.95    0.0    0.75    0.95 no filter          filter

TIA1-STAMP-high

UUUUAC

All
p=1e-41

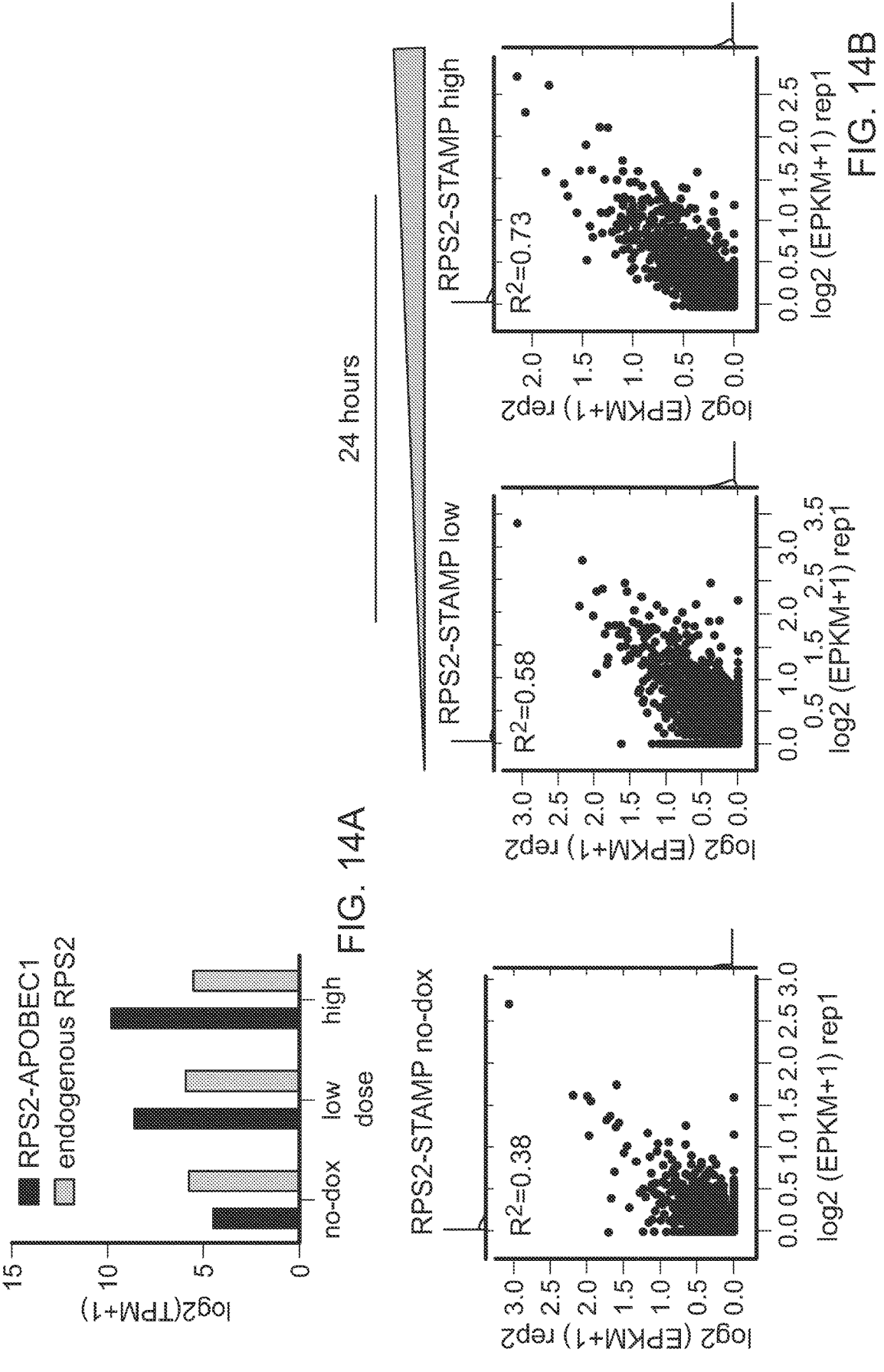

RBFOX2-STAMP
long-read ONT
UACUGCAUGU
p = 1e-71

RBFOX2-STAMP
long-read PB
AUGGCAUG
p = 1e-259

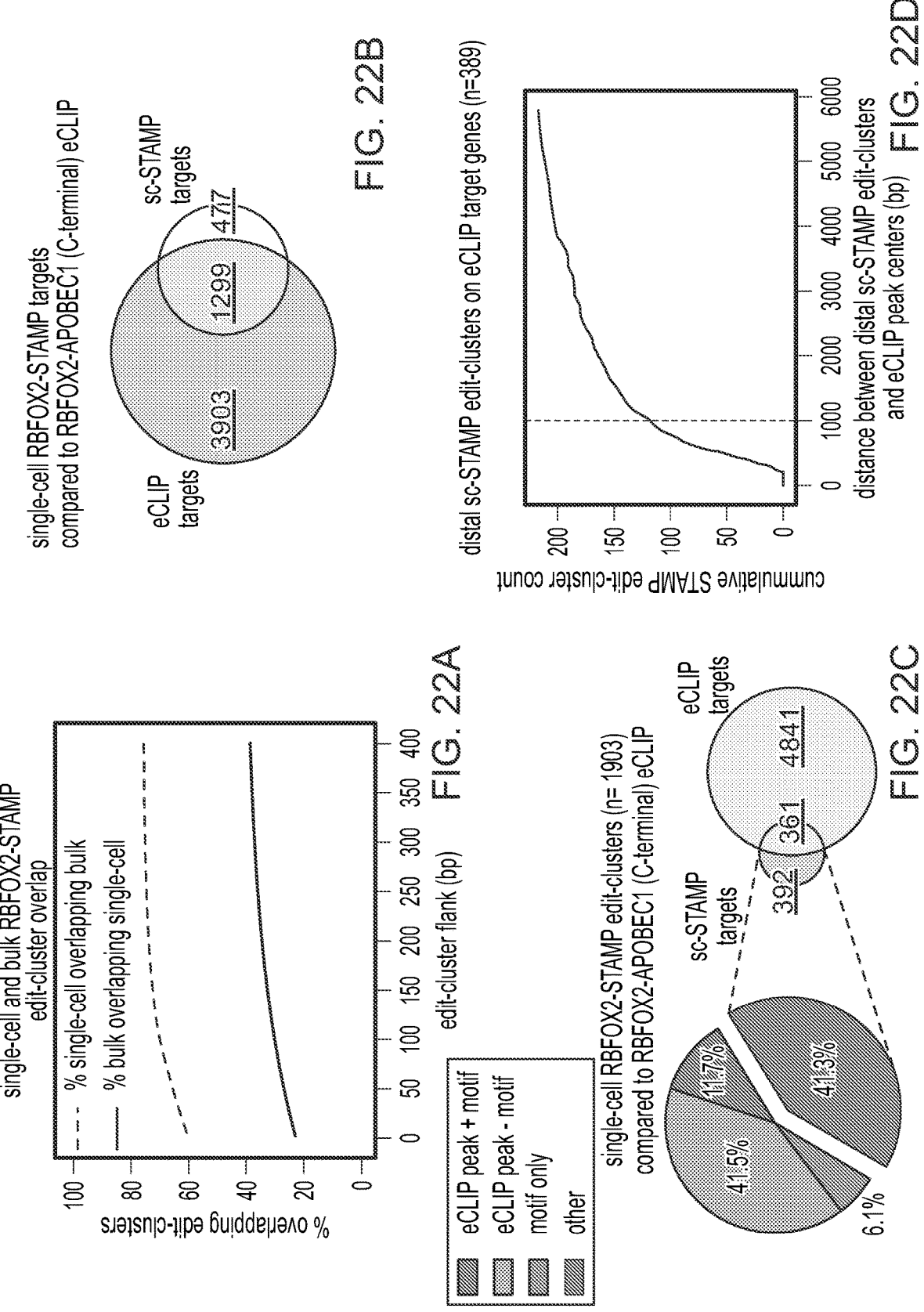

RBFOX2-cluster all cells
All
p=1e-87
control-STAMP all cells
All
p=1e-11
FIG. 26C

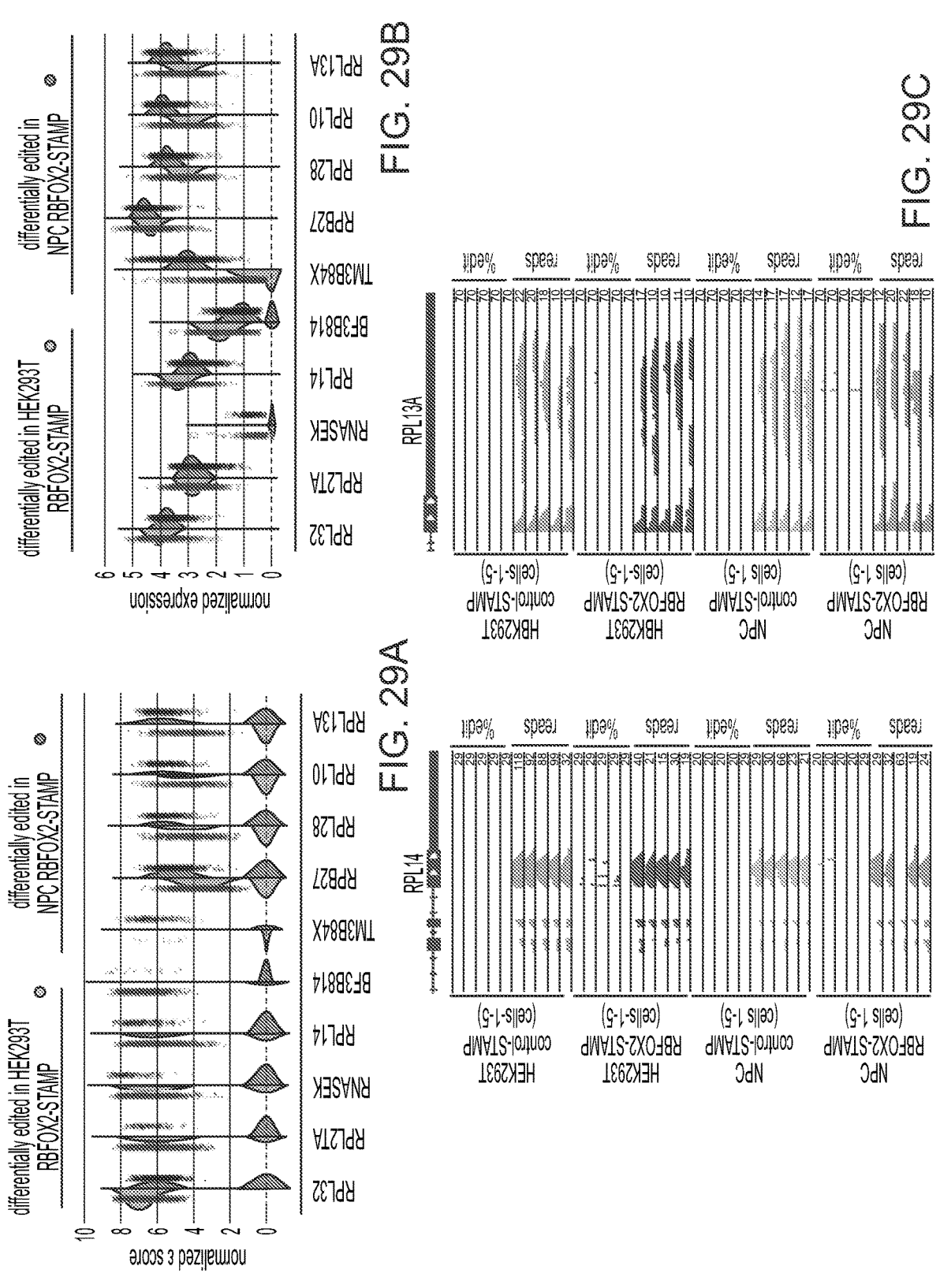

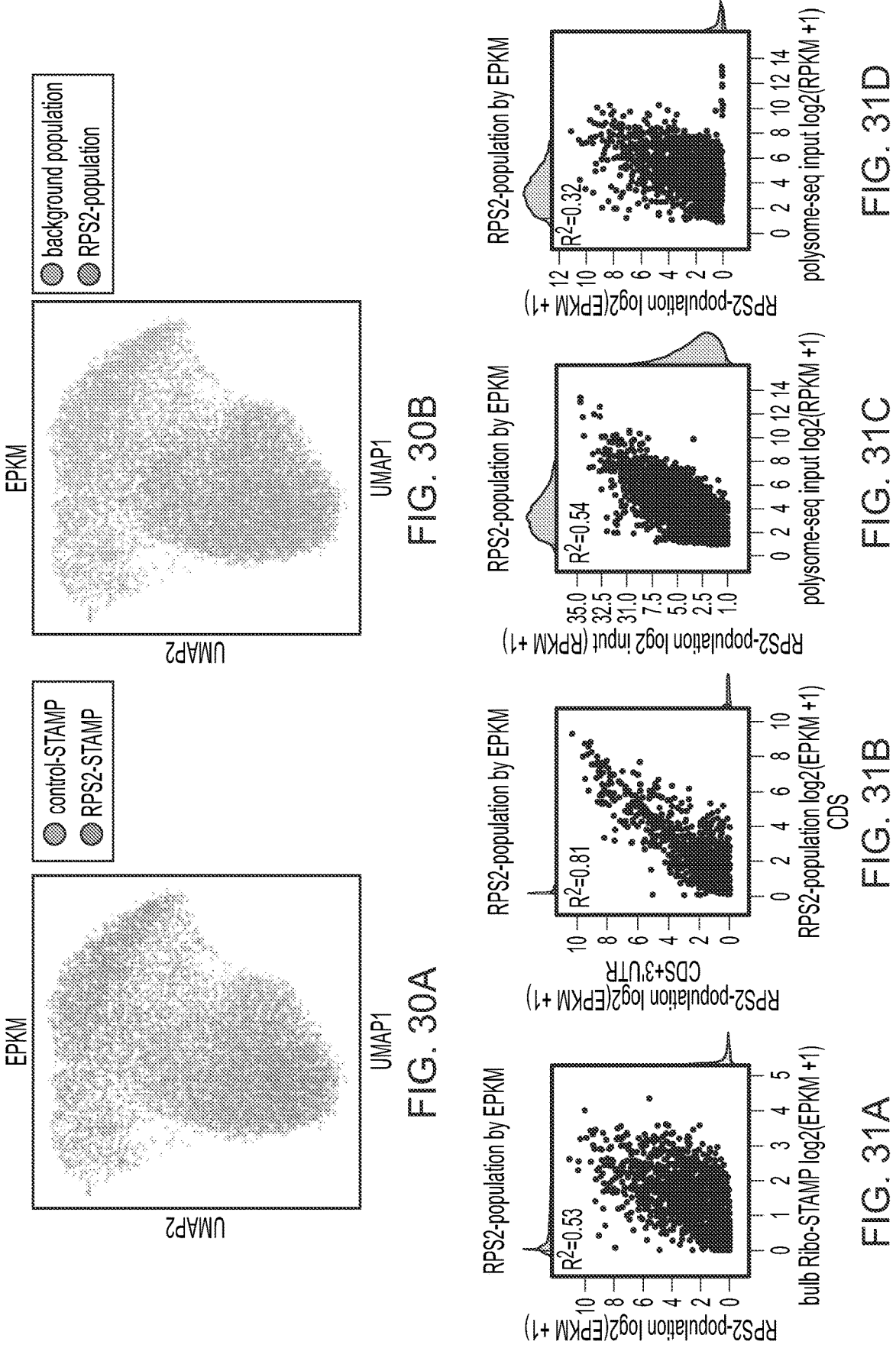

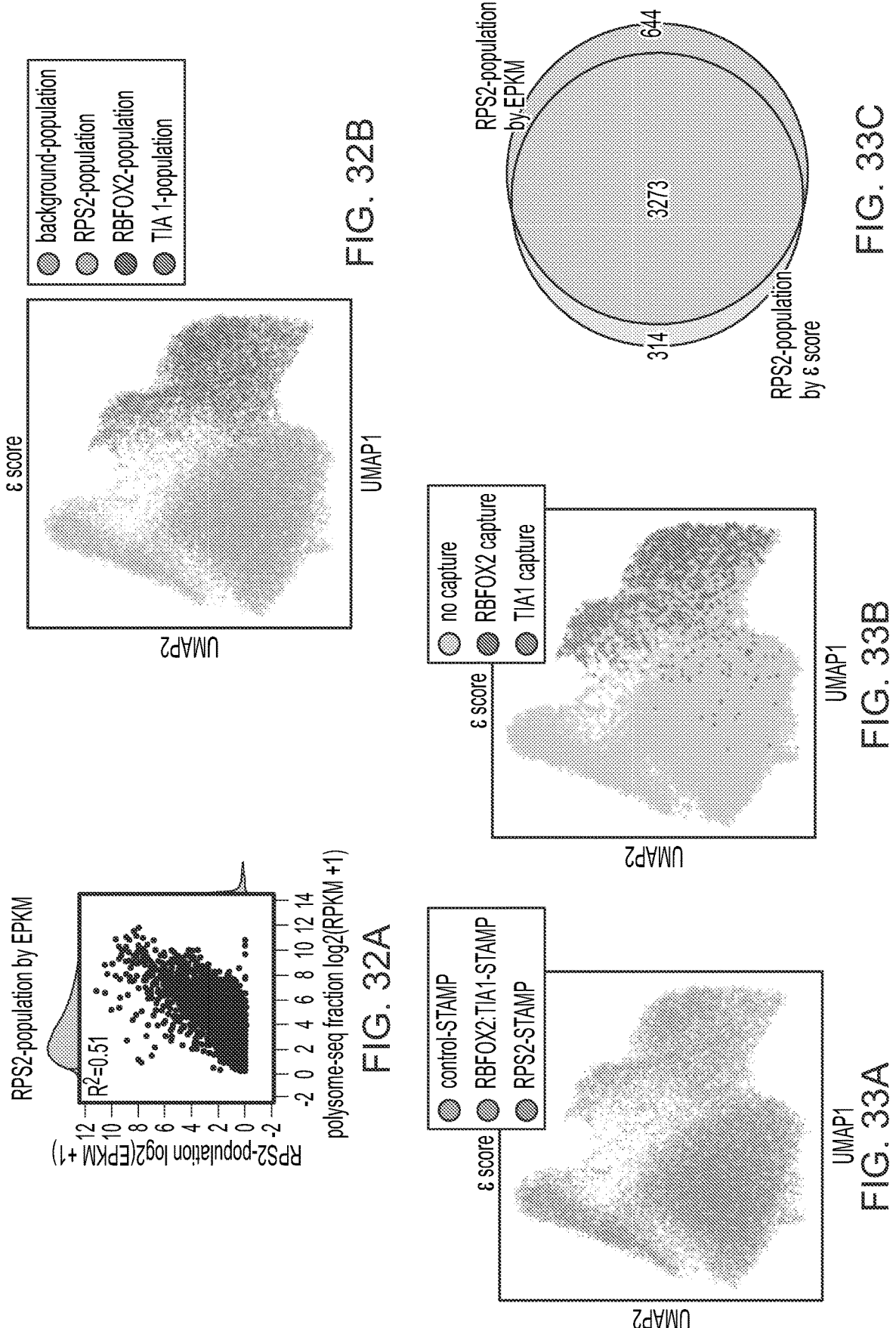

METHODS AND USE OF CHIMERIC PROTEINS

CROSS-REFERENCE TO RELATED APPLICATIONS

This application is a National Stage Application under 35 U.S.C. § 371 and claims the benefit of International Application No. PCT/US2021/022150, filed Mar. 12, 2021, which claims priority to U.S. Provisional Application Ser. No. 62/988,722, filed on Mar. 12, 2020. The disclosure of the prior application is considered part of the disclosure of this application, and is incorporated herein by reference in its entirety.

FEDERALLY SPONSORED RESEARCH OR DEVELOPMENT

This invention was made with Government support under Grant Nos. HG004659, H0009889, NS112678, GM068524, CA067754, and NS111859 awarded by the National Institutes of Health. The Government has certain rights in the invention.

BACKGROUND

Current techniques and tools for measuring translation efficiency often require techniques such as ribosome profiling and/or polysome profiling which requires the removal of ribosomal RNA due to unwanted contamination of the ribosome/polysome fractions and/or libraries.

SUMMARY

The present disclosure is based, at least in part, on the generation of chimeric proteins to enable RNA modifications that can be detected by sequencing methods as a surrogate measure for ribosome initiation, scanning, elongation, and release.

Provided herein are methods for determining a relative translation rate of a target mRNA in a cell, as compared to a non-target mRNA, the method comprising: (a) introducing into the cell a chimeric protein comprising (i) an RNA binding protein and (ii) an RNA editing protein; (b) determining a plurality of nucleotide substitutions introduced into the target mRNA by the RNA editing protein; and (c) comparing the determined plurality of nucleotide substitutions introduced into the target mRNA to a plurality of nucleotide substitutions introduced into the non-target mRNA in the cell, thereby determining the relative translation rate of the target mRNA in the cell, as compared to the non-target mRNA.

Provided herein are methods for determining an RNA binding protein binding site on a target mRNA in a cell, the method comprising: (a) introducing into the cell a chimeric protein comprising (i) an RNA binding protein or a fragment thereof and (ii) an RNA editing protein or a fragment thereof; (b) determining a plurality of nucleotide substitutions introduced into the target mRNA by the RNA editing protein or fragment thereof; and (c) identifying a region on the target mRNA where the plurality of nucleotide substitutions are introduced into the target mRNA, thereby determining an RNA binding protein binding site wherein the RNA binding protein binds to the mRNA in the cell.

In some embodiments, the RNA binding protein is a full-length RNA binding protein. In some embodiments, the chimeric protein further comprises a ribosomal protein. In some embodiments, the ribosomal protein is a full-length ribosomal protein. In some embodiments, the ribosomal protein is a ribosomal protein subunit. In some embodiments, the chimeric protein comprises two or more ribosomal proteins. In some embodiments, the ribosomal protein is a translation initiation factor or a fragment thereof. In some embodiments, the ribosomal protein is a translation elongation factor or a fragment thereof. In some embodiments, the ribosomal protein is a translation termination factor or a fragment thereof. In some embodiments, the ribosomal protein or fragment thereof is selected from the group consisting of: RPS2, RPS3, RPS3A, RPS4X, RPS4Y1, RPS4Y2, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS28, RPS29, RPS30, RSSA, RACK1, RPL3, RPL4, RPL5, RPL6, RPL7A, RPL7, RPL8, RPL9, RPL10A, RPL10, RPL11, RPL12, RPL13A, RPL13, RPL14, RPL15, RPL17, RPL18A, RPL18, RPL19, RPL21, RPL22, RPL23A, RPL23, RPL24, RPL26, RPL27A, RPL27, RPL28, RPL29, RPL30, RPL31, RPL32, RPL34, RPL35A, RPL35, RPL36, RPL37A, RPL37, RPL38, RPL39, RPL40, RPL41, RPLA0, RPLA1, and RPLA2.

In some embodiments, the target mRNA is a full-length mRNA isoform.

In some embodiments, step (a) introducing into the cell the chimeric protein comprises introducing a nucleic acid encoding the chimeric protein. In some embodiments, the nucleic acid is present in an expression vector. In some embodiments, the expression vector is a viral vector. In some embodiments, the viral vector is a lentiviral vector.

In some embodiments, the RNA editing protein is a cytidine deaminase or a fragment thereof. In some embodiments, the cytidine deaminase is an apolipoprotein B mRNA editing enzyme, catalytic polypeptide-like (APOBEC) protein. In some embodiments, the APOBEC protein is selected from the group consisting of: APOBEC1, APOBEC2, APOBEC3A, APOBEC3B, APOBEC3C, APOBEC3D, APOBEC3F, APOBEC3G, APOBEC3H, and APOBEC4. In some embodiments, the RNA editing protein is an adenosine deaminase or a fragment thereof. In some embodiments, the adenosine deaminase is an adenosine deaminase acting on RNA (ADAR). In some embodiments, the adenosine deaminase is an adenosine aminohydrolase (ADA). In some embodiments, the RNA editing protein is N-terminally positioned relative to the RNA binding protein in the chimeric protein. In some embodiments, the RNA editing protein is C-terminally positioned relative to the RNA binding protein in the chimeric protein.

In some embodiments, step (b) comprises sequencing the target mRNA. In some embodiments, the sequencing of the target mRNA is performed using single cell nucleic acid sequencing. In some embodiments, the sequencing of the target mRNA is performed using long-read sequencing.

Provided herein are chimeric proteins comprising (a) an RNA binding protein and (b) an RNA editing protein, wherein the RNA editing protein introduces a plurality of nucleotide substitutions into a target mRNA in a cell.

In some embodiments, the RNA binding protein is a full-length RNA binding protein. In some embodiments, the chimeric protein further comprising a ribosomal protein. In some embodiments, the ribosomal protein is a full-length ribosomal protein. In some embodiments, the ribosomal protein is a ribosomal protein subunit. In some embodiments, the chimeric protein comprises two or more ribosomal proteins. In some embodiments, the ribosomal protein is a translation initiation factor or a fragment thereof. In some embodiments, the ribosomal protein is a translation elongation factor or a fragment thereof. In some embodiments, the ribosomal protein is a translation termination factor or a fragment thereof. In some embodiments, the ribosomal protein is selected from the group consisting of: RPS3, RPS3A, RPS4X, RPS4Y1, RPS4Y2, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS28, RPS29, RPS30, RSSA, RACK1, RPL3, RPL4, RPL5, RPL6, RPL7A, RPL7, RPL8, RPL9, RPL10A, RPL10, RPL11, RPL12, RPL13A, RPL13, RPL14, RPL15, RPL17, RPL18A, RPL18, RPL19, RPL21, RPL22, RPL23A, RPL23, RPL24, RPL26, RPL27A, RPL27, RPL28, RPL29, RPL30, RPL31, RPL32, RPL34, RPL35A, RPL35, RPL36, RPL37A, RPL37, RPL38, RPL39, RPL40, RPL41, RPLA0, RPLA1, and RPLA2.

In some embodiments, the RNA editing protein is a cytidine deaminase or a fragment thereof. In some embodiments, the cytidine deaminase is an apolipoprotein B mRNA editing enzyme, catalytic polypeptide-like (APOBEC) protein. In some embodiments, the APOBEC protein is selected from the group consisting of: APOBEC1, APOBEC2, APOBEC3A, APOBEC3B, APOBEC3C, APOBEC3D, APOBEC3F, APOBEC3G, APOBEC3H, and APOBEC4. In some embodiments, the RNA editing protein is an adenosine deaminase or a fragment thereof. In some embodiments, the adenosine deaminase is an adenosine deaminase acting on RNA (ADAR). In some embodiments, the adenosine deaminase is an adenosine aminohydrolase (ADA). In some embodiments, the RNA editing protein is N-terminally positioned relative to the RNA binding protein in the chimeric protein. In some embodiments, the RNA editing protein is C-terminally positioned relative to the RNA binding protein in the chimeric protein.

Provided herein are cells comprising any one of the chimeric proteins described herein.

Provided herein are nucleic acids encoding any one of the chimeric proteins described herein.

Provided herein are expression vectors comprising any one of the nucleic acids described herein. In some embodiments, the expression vector is a viral vector. In some embodiments, the viral vector is a lentiviral vector.

Provided herein are cells comprising any one of the nucleic acids described herein or any one of the expression vectors described herein.

Provided herein are kits comprising any one of the chimeric proteins described herein, any one of the nucleic acids described herein, or any one of the expression vectors described herein. In some embodiments, the kit further comprises instructions for performing any one of the methods described herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 1 is an exemplary schematic showing that APOBEC protein edits single-stranded substrates to convert cytosine to uracil and ADAR proteins edits adenosines within double-stranded RNA substrates to inosines.

FIG. 14A is a bar graph showing quantification of expression from no dox (0 ng/ml) low (50 ng/ml) or high (1 µg/ml) doxycycline induction of RPS2-APOBEC1 fusion compared to endogenous expression. Results show dose-dependent STAMP-fusion expression compared to endogenous RPS2 levels.

FIGS. 14B-14D show scatterplot comparisons of CDS+3'UTR EPKM values from RPS2-STAMP replicate experiments showing high, dose-dependent correlation at 24 (FIG. 14B), 48 (FIG. 14C) and 72 hours (FIG. 14D). Results show strong EPKM reproducibility between replicates as well as low overlap between control-STAMP and RPS2-STAMP edit sites at high induction.

FIG. 14E shows scatterplot comparison of CDS EPKM values with CDS+3'UTR EPKM values for RPS2-STAMP. Results indicate that 3'UTR edits may provide edits otherwise missed of only CDS regions in genes with short open-reading frames were considered.

STAMP across 5'UTR, CDS and 3'UTR gene regions for the top quartile (n=4,931) of ribosome occupied genes (ribo-seq).

Figures 17A, 17B:
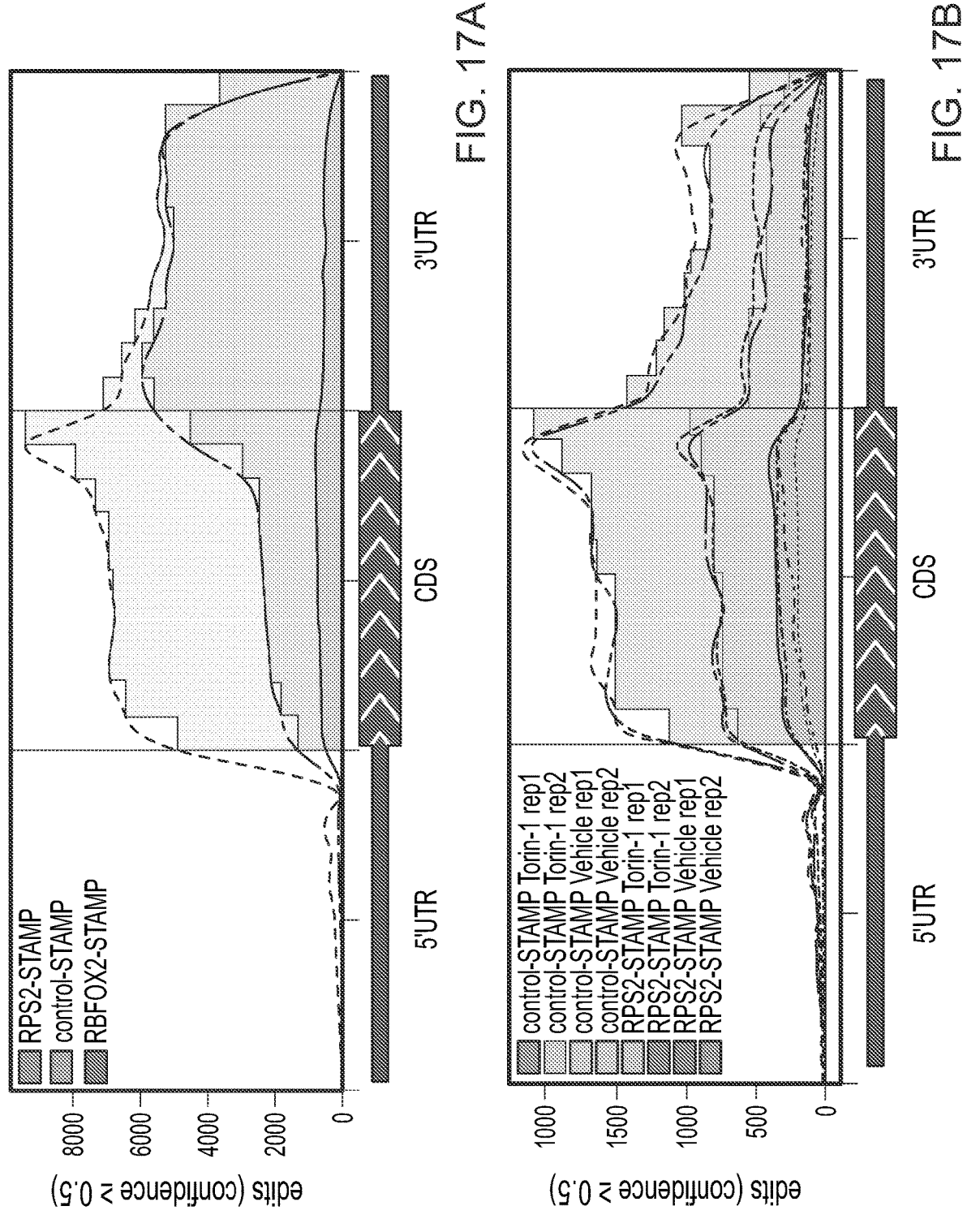
FIG. 17A shows a metagene plot showing edit (≥0.5 confidence score) distribution for high-induction RPS2-STAMP compared to control-STAMP and RBFOX2-

FIG. 17B is a metagene plot as in FIG. 17A showing edit (≥0.5 confidence level) distribution for vehicle-treated 72-hour high-induction RPS2-STAMP compared to replicate Torin-1 treated 72-hour high-induction RPS2-STAMP across 5'UTR, CDS and 3'UTR gene regions for the top quartile of ribosome occupied genes.

Figures 18A, 18B:
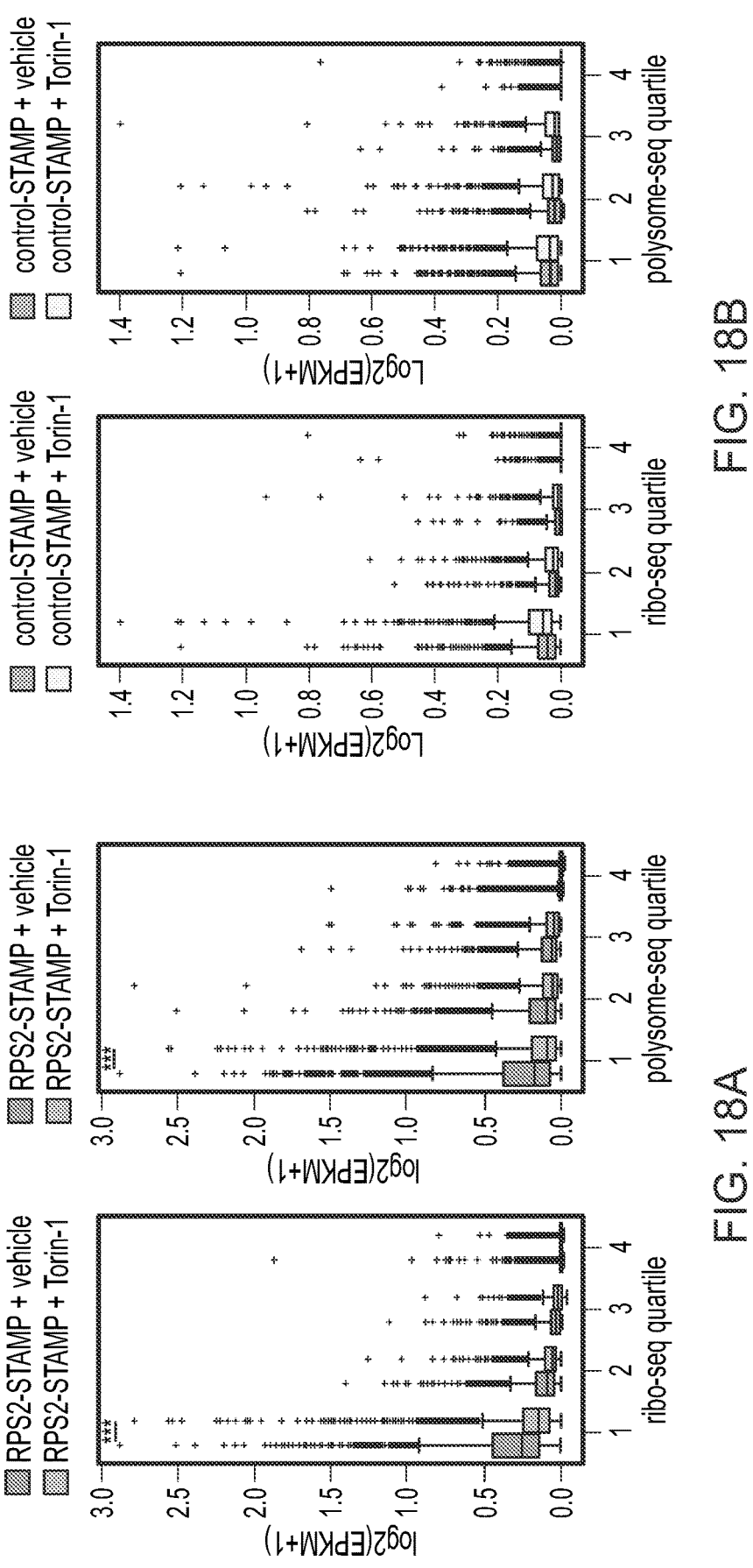

FIG. 18A shows comparison of EPKM from vehicle treated 72-hour high induction RPS2-STAMP compared to Torin-1 treated 72-hour high-induction RPS2-STAMP showing significant signal reduction for top ribosome occupied quartile genes containing Torin-1 sensitive TOP genes as detected by ribo-seq (Q1 p=1.5 e-144, Wilcoxon rank-sum) and polysome profiling (Q1 p=5.5 e-108, Wilcoxon rank-sum).

FIG. 18B shows comparison of EPKM from vehicle treated 72-hour high-induction control-STAMP compared to Torin-1 treated 72-hour high-induction control-STAMP showing no significant signal reduction for top ribosome occupied quartile genes containing Torin-1 sensitive TOP genes as detected by ribo-seq. Results demonstrate that specific and dynamic translational responses can be detected by Ribo-STAMP.

Figure 19B:
Figure 19A:
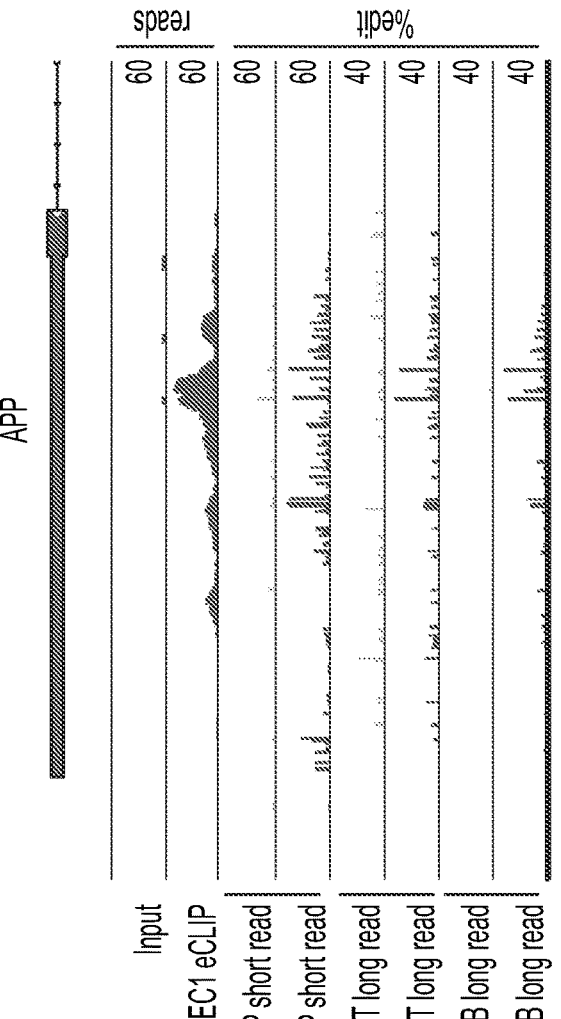

FIG. 19A shows IGV tracks showing RBFOX2 eCLIP peak on the target gene APP, compared with 72-hour high-induction control- and RBFOX2-STAMP SAILOR quantified edit fractions for both long-read (Oxford Nanopore Technologies (ONT) or PacBio (PB)) direct cDNA, and short read (NGS) outputs. Results show long-read sequencing approaches resulted in enrichment above control of C-to-U edits from RBFOX2-STAMP that overlapped with both eCLIP signal and short read (Illumina) RBFOX2-STAMP signal, as illustrated by the target gene APP 3'UTR.

FIG. 19B shows homer motif analysis of RBFOX2-STAMP long-reads (ONT and PB) for edits above 0.99 confidence.

Figures 20A, 20B:
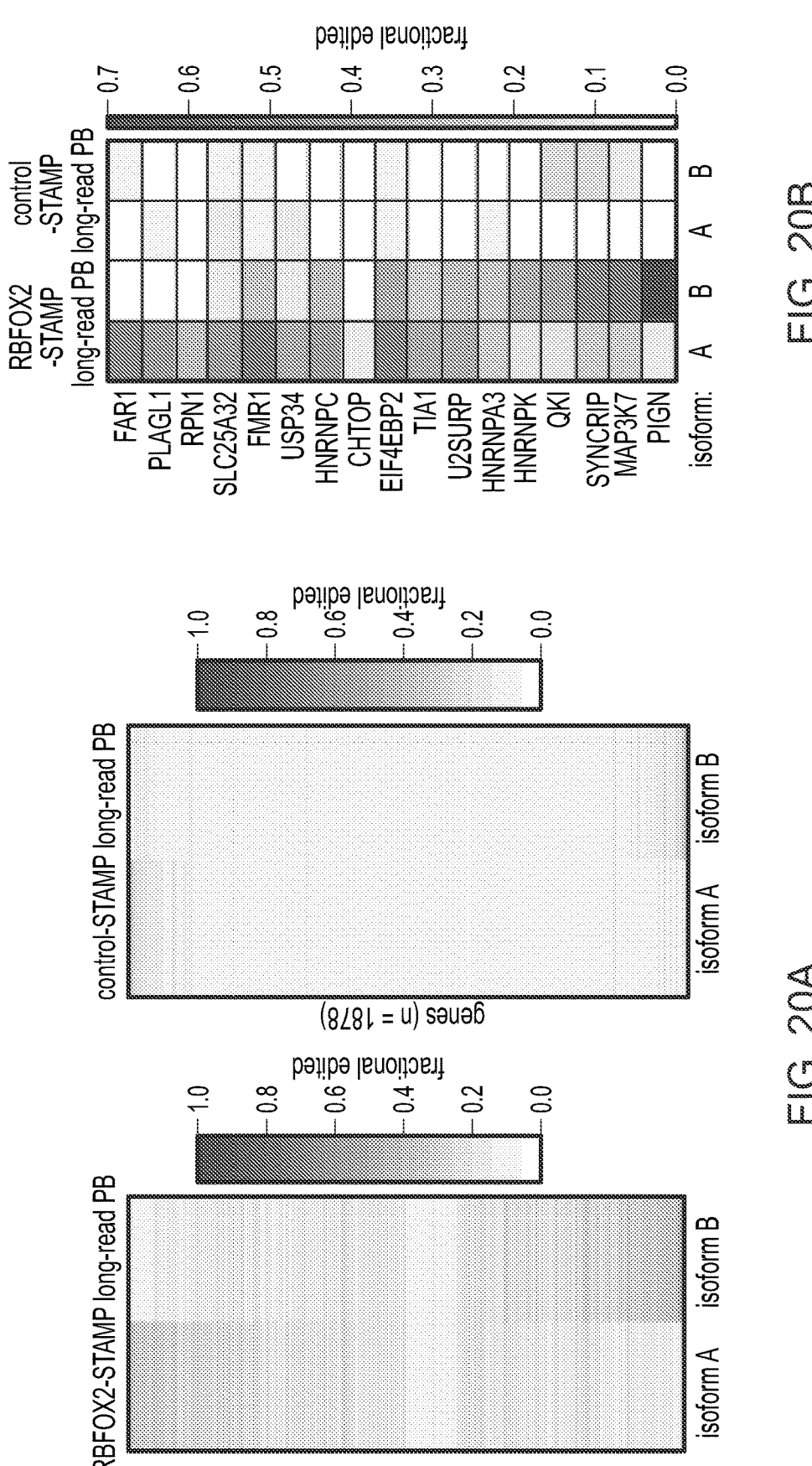

FIG. 20A shows a heatmap of control- and RBFOX2-STAMP edit fractions calculated from the final exon of all detected primary and secondary alternative polyadenylation (APA) isoforms meeting coverage criteria where differential isoform editing signatures were observed for RBFOX2-STAMP and compared to control-STAMP.

FIG. 20B shows a heatmap of control- and RBFOX2-STAMP edit fractions on the two primary alternative polyadenylation (APA) isoforms for the top differentially edited RBFOX2-STAMP APA targets.

Figure 20C:
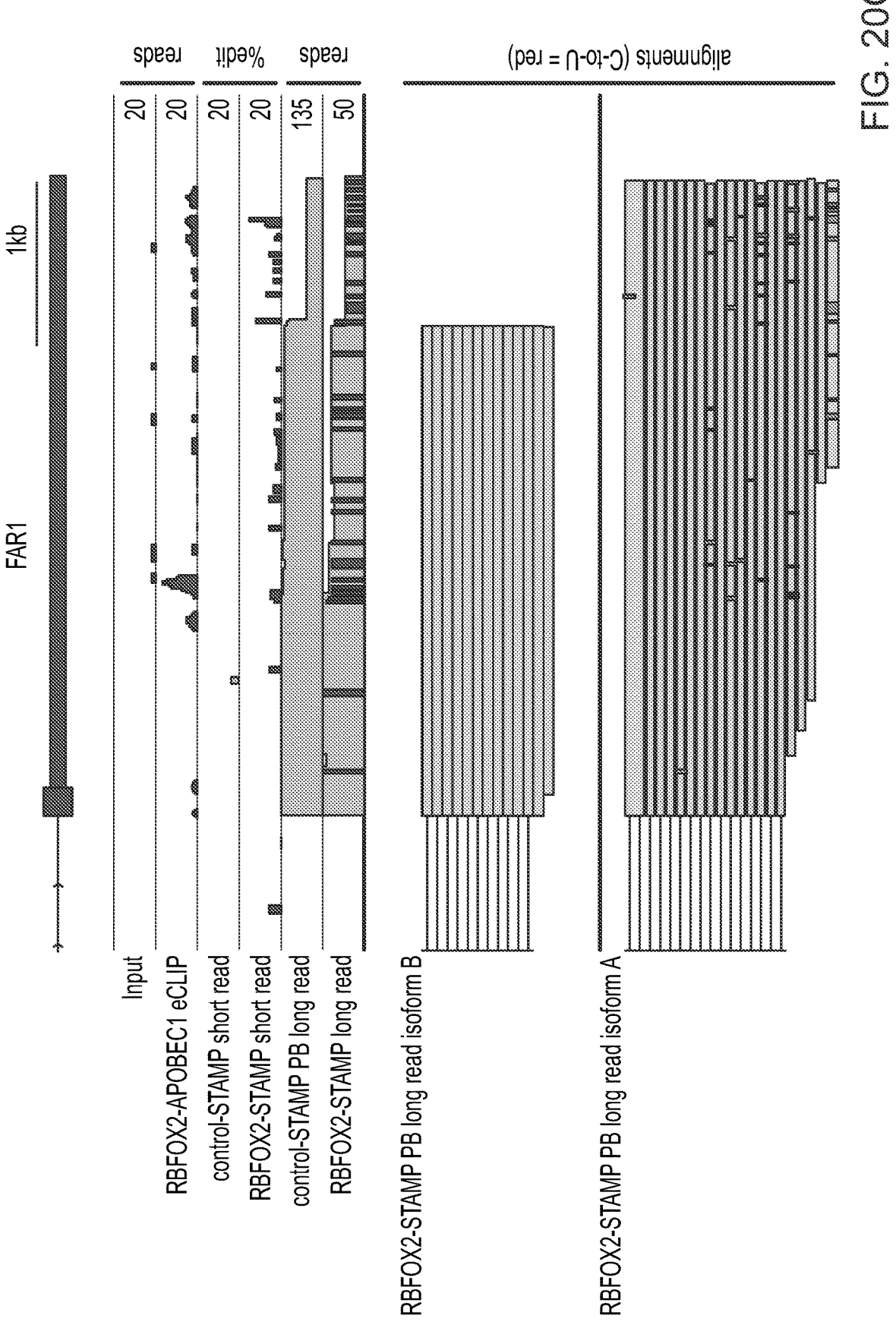

FIG. 20C shows IGV tracks showing RBFOX2-APOBEC1 eCLIP peaks, control and RBFOX2-STAMP short-read edit frequencies, and control- and RBFOX2-756 STAMP long-read (PB) alignments on the two primary isoforms of the target gene FAR1, with C-to-U conversions shown on different isoforms.

Figure 20D:
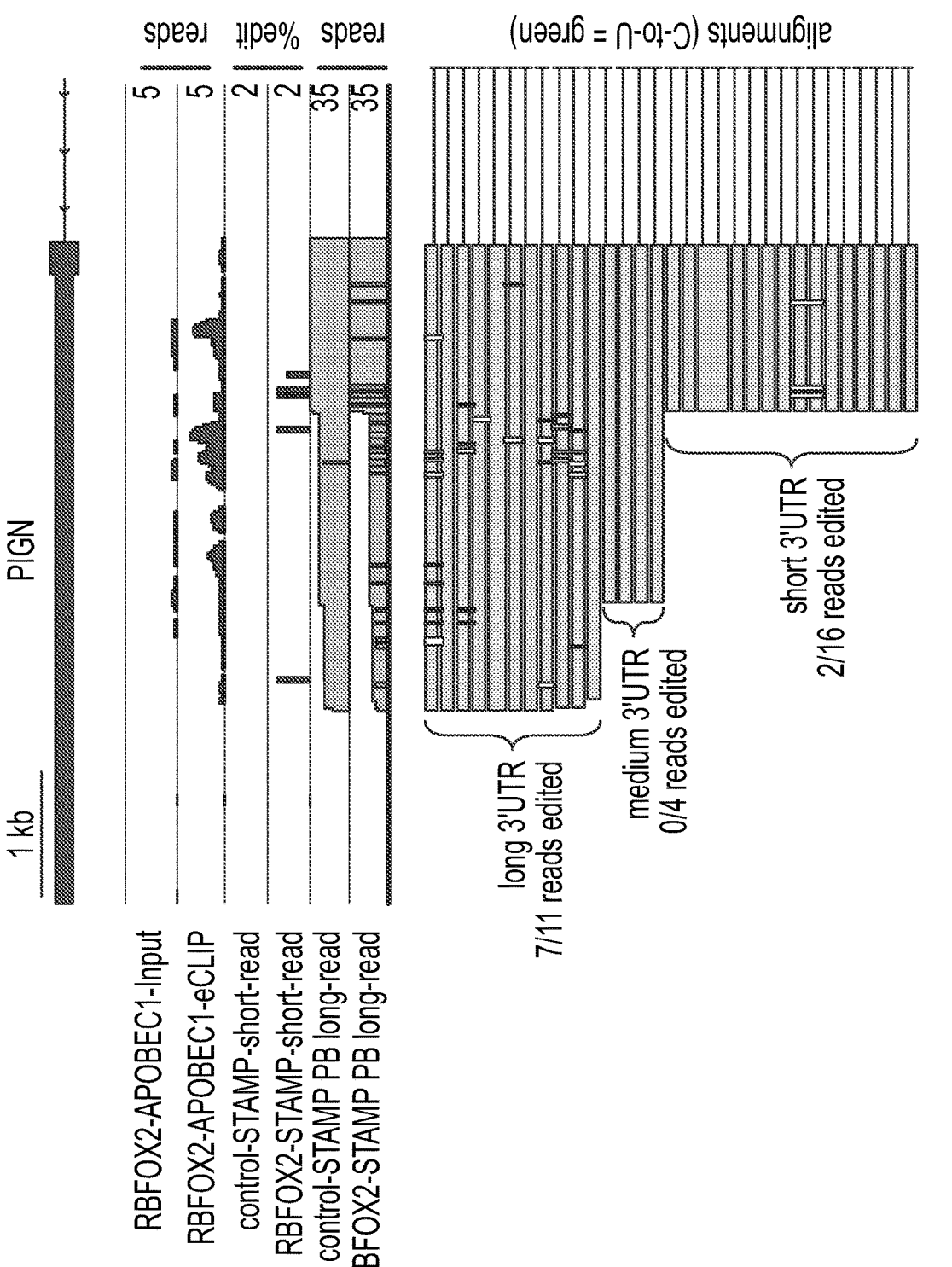

FIG. 20D shows IGV tracks showing RBFOX2-APOBEC1 eCLIP peaks, control- and RBFOX2-STAMP short-read edit clusters, compared to control- and RBFOX2-STAMP long-read (PB) alignments on long, middle and short APA isoforms of the target gene PIGN, with C-to-U conversions shown on different isoforms. Results demonstrate that STAMP enables isoform-aware long read detection of RBP-RNA interactions.

Figures 21A, 21B, 21C:
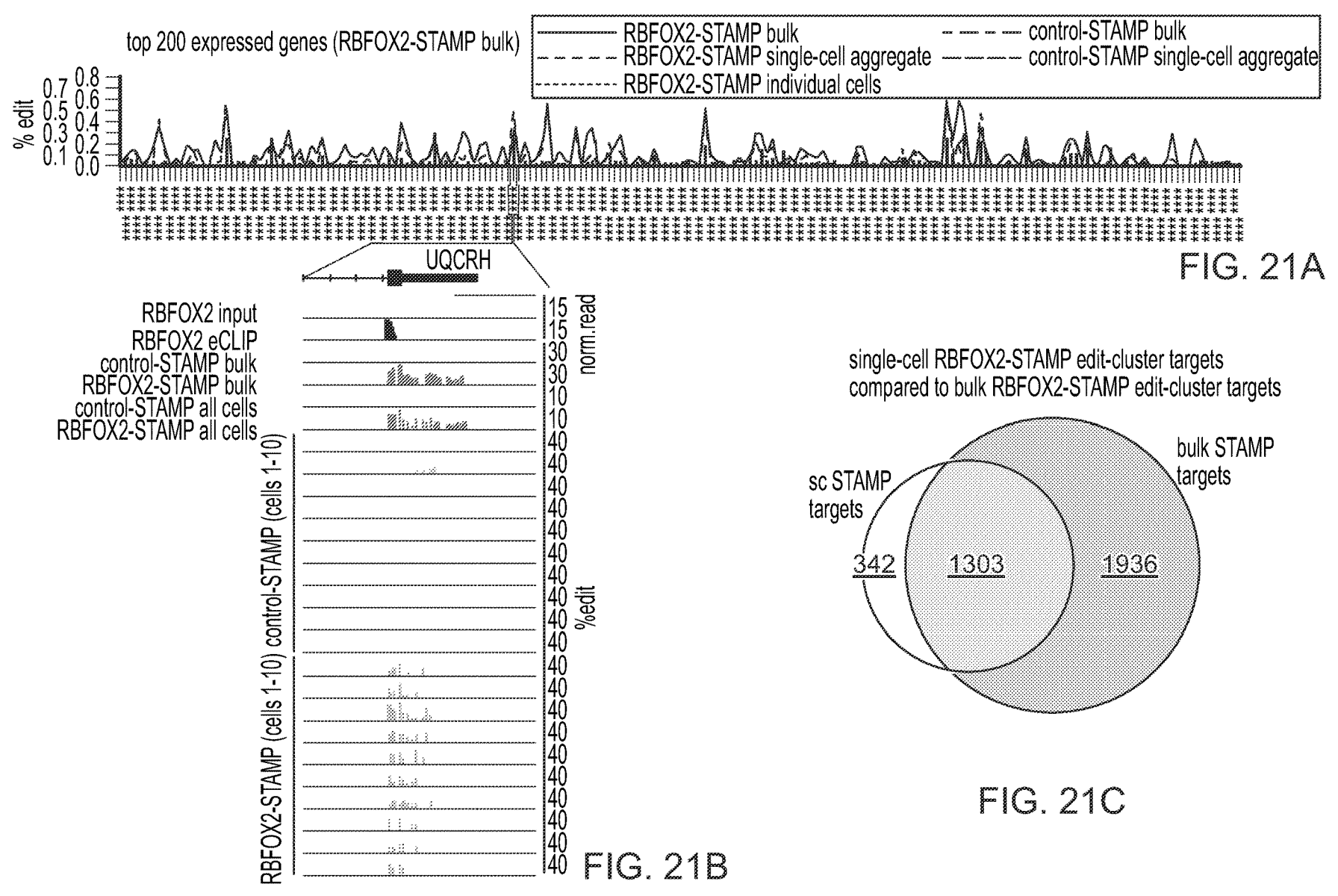

FIG. 21A shows edit fraction comparison of bulk 72-hour high-induction control- and RBFOX2-STAMP with single-cell control- and RBFOX2-STAMP across the top 200 genes ranked by transcripts per million (TPM) from bulk RBFOX2-STAMP RNA-seq.

FIG. 21B shows IGV tracks showing the RBFOX2 eCLIP peak on the target gene UQCRH, compared with RBFOX2-STAMP edit fractions for the top 10 control- and RBFOX2-STAMP cells ranked by summed ε scores. Results show consistent edit signal in close proximity to the RBFOX2 eCLIP peak that overlapped with edit enrichment from both bulk RBFOX2-STAMP and the aggregate of all RBFOX2-STAMP cells, demonstrating that STAMP can define RBP binding sites at single-cell resolution.

FIG. 21C shows overlap between single-cell and bulk RBFOX2-STAMP target genes containing edit-clusters.

FIG. 22A is a graph showing evaluation of percentage overlap between bulk and single-cell edit-clusters showing that 60-75% of single-cell edit clusters overlap bulk edit clusters over increasing cluster-flanking regions.

FIG. 22B shows overlap between RBFOX2-APOBEC1 eCLIP target transcripts (peaks log2fc>2 and –log10p>3 over input) and single-cell RBFOX2-STAMP edit-cluster containing target transcripts. Results show that 73% of single-cell STAMP targets that contained edit-clusters also contained significant RBFOX2-APOBEC1 eCLIP peaks.

FIG. 22C is a pie chart showing the proportion of single-cell RBFOX2-STAMP edit-clusters overlapping either 1) RBFOX2-APOBEC1 fusion high-confidence eCLIP peaks (log2fc>2 and –log10p>3 over input) containing the conserved RBFOX2 binding motif (GCAUG), 2) equally stringent eCLIP peaks not containing the conserved motif, 3) the conserved motif falling outside of eCLIP peaks, or 4) neither eCLIP peaks nor conserved motifs.

FIG. 22D is a graph showing cumulative distance measurement from single-cell RBFOX2-STAMP distal edit-clusters to eCLIP peaks on targets genes.

Figure 23A:
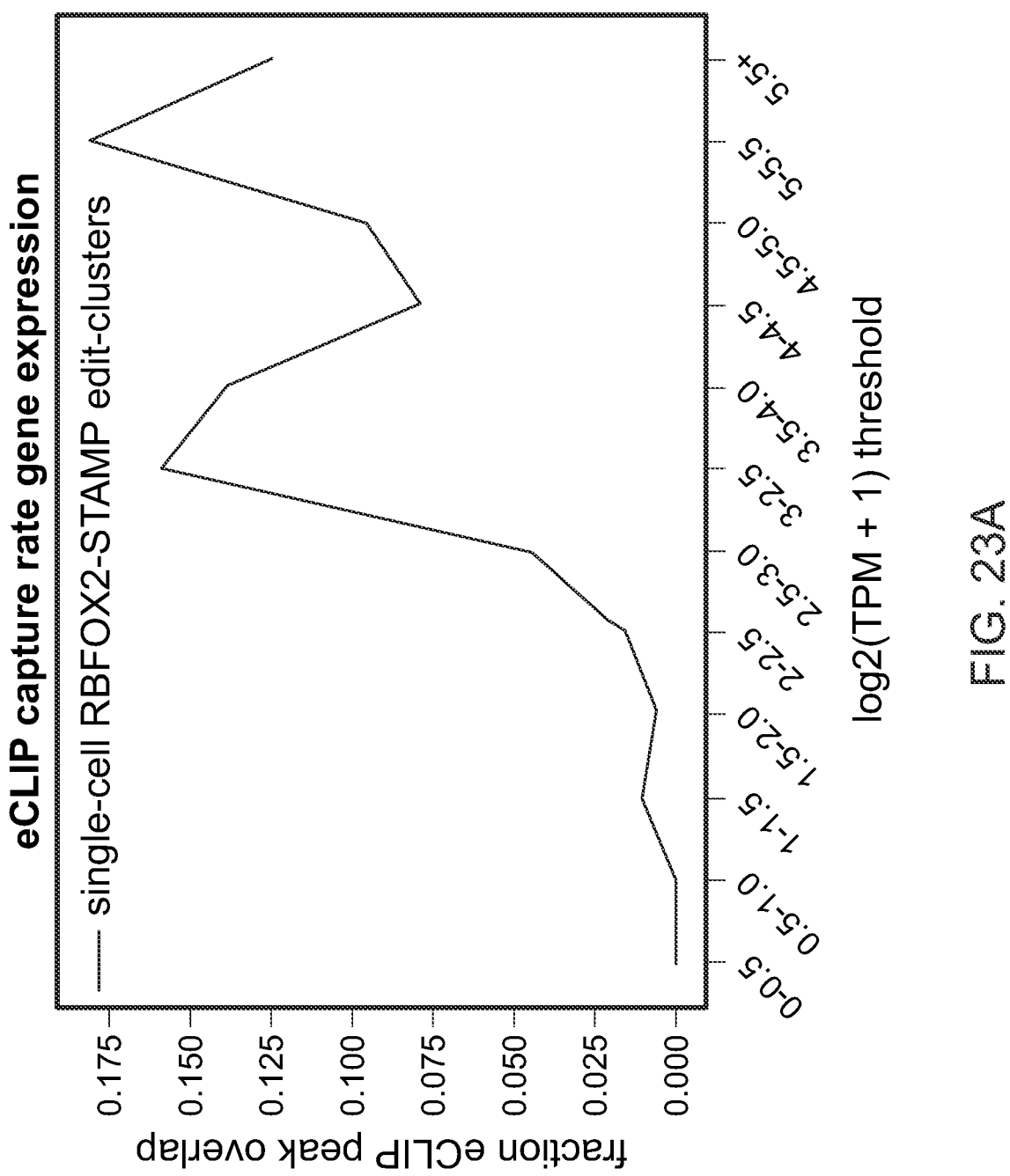

FIG. 23A is a graph showing fraction of RBFOX2-APOBEC1 eCLIP peaks overlapping low and high induction single-cell RBFOX2-STAMP edit clusters at increasing expression (TPM) thresholds where results show single-cell RBFOX2-STAMP eCLIP peak capture rate was associated with target expression level.

Figure 23B:
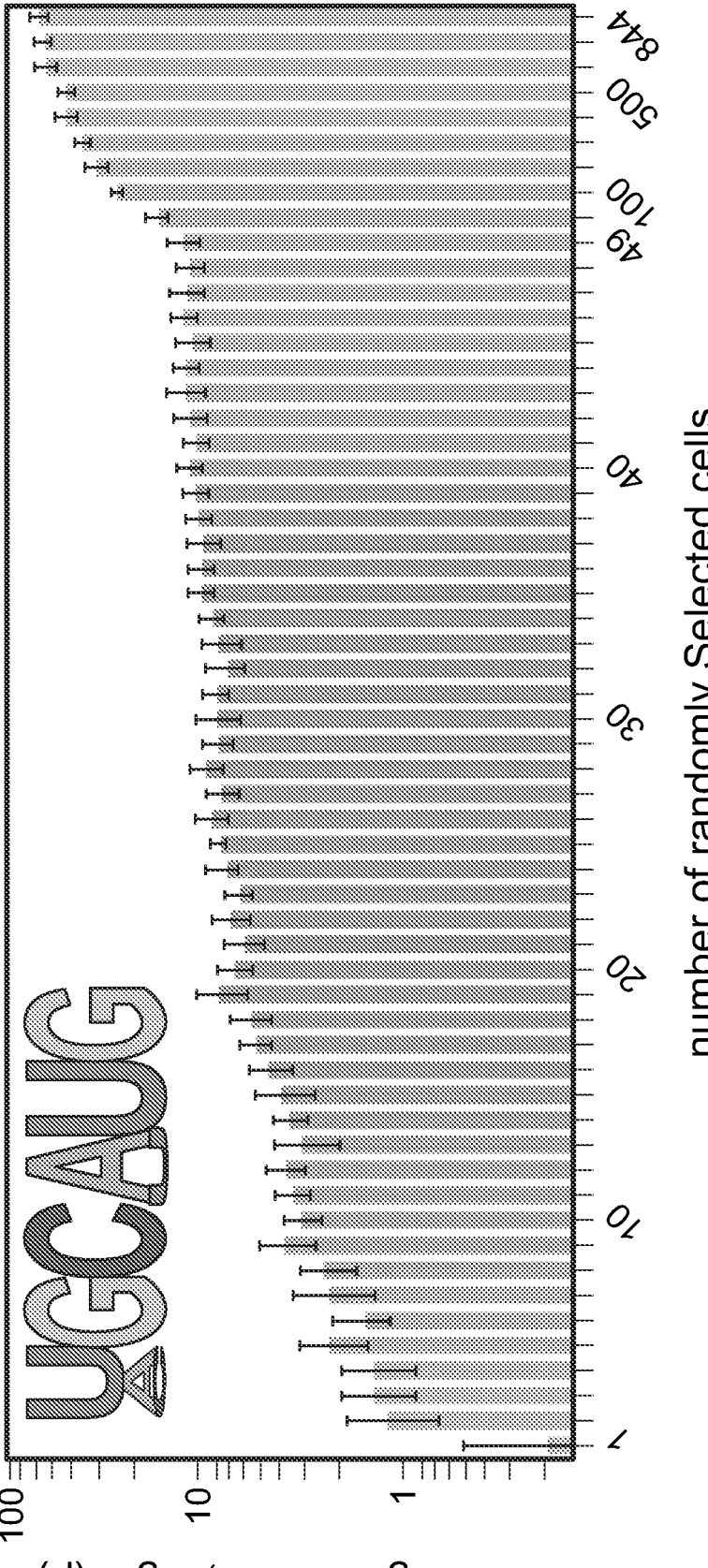

FIG. 23B shows –log10 of p-values (n=10 trials) for motifs extracted by HOMER (v4.9.1) using RBFOX2-STAMP≥0.99 confidence level edits from randomly sampled cells showing RBFOX2 motif detection to single cell resolution where results demonstrate the strength of single-cell STAMP.

Figures 24A, 24B, 24C, 25A, 25B, 25C:
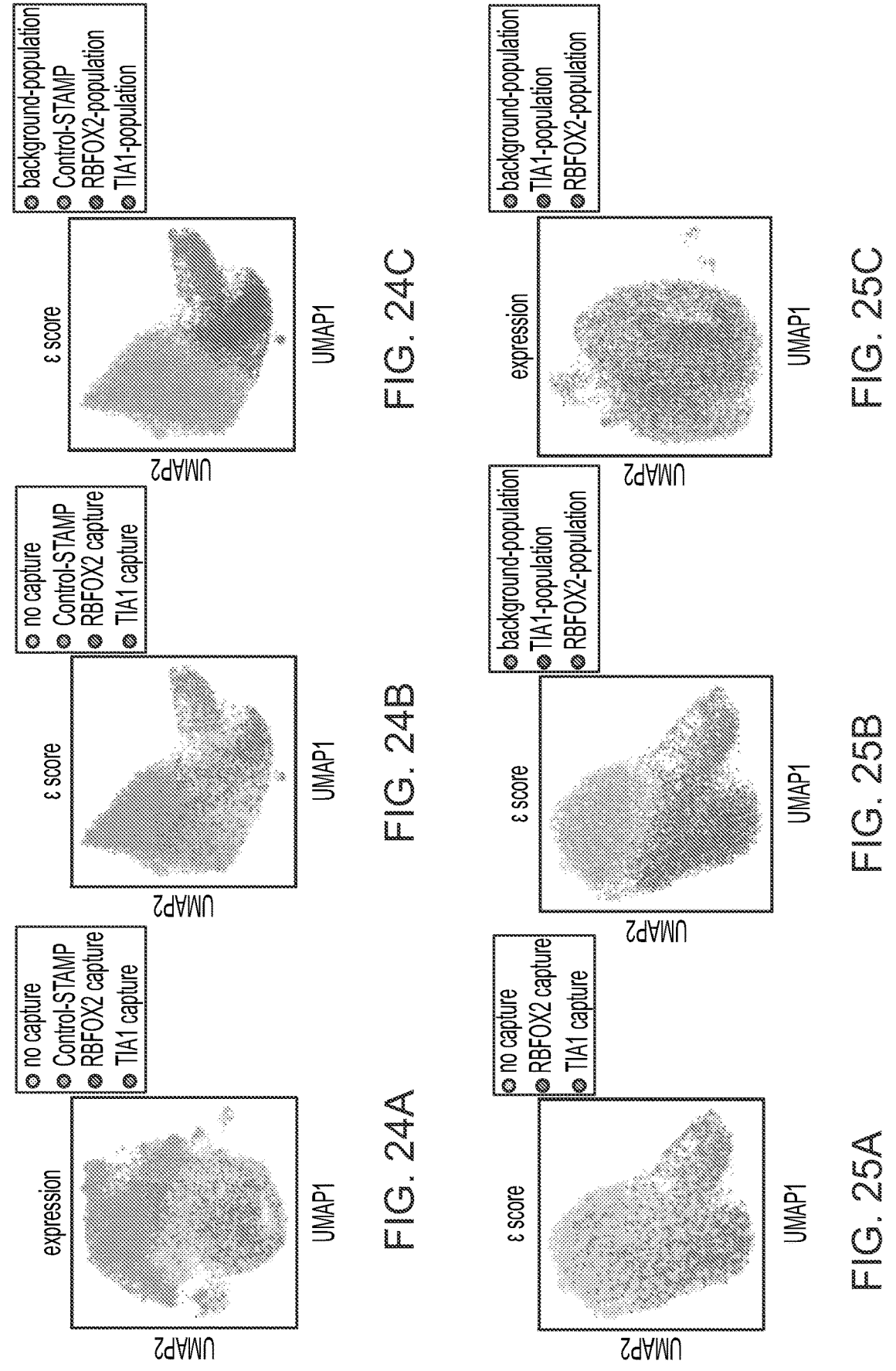

FIG. 24A shows a Uniform Manifold Approximation and Projection (UMAP) analysis of gene expression from merged 72-hour high-induction control- and RBFOX2:TIA1-STAMP cells with capture sequence RBFOX2-STAMP and TIA1-STAMP cells highlighted.

FIG. 24B shows a UMAP analysis using ε score rather than gene expression after merging 72-hour high-induction control-STAMP cells. Results show that the single-cell ε score profiles of TIA1- and RBFOX2-STAMP targets were sufficiently distinct, demonstrating that targets of multiple RBPs can be simultaneously discovered from a single multiplexed experiment.

FIG. 24C shows a UMAP plot as in FIG. 24B indicated by ε score Louvain clustering into RBFOX2-population, TIA1-population and background-population populations with control-STAMP cells overlaid.

FIG. 25A shows a UMAP plot using ε score from RBFOX2-STAMP and TIA1-STAMP mixture with capture sequence RBFOX2-STAMP and TIA1-STAMP cells highlighted.

FIG. 25B shows a UMAP plot as in FIG. 25A indicated by Louvain clustering into RBFOX2-cluster, and TIA1-cluster, or background-cluster populations.

FIG. 25C shows a UMAP plot of gene expression for ε score Louvain clusters defined in FIG. 25B.

Figures 26A, 26B:
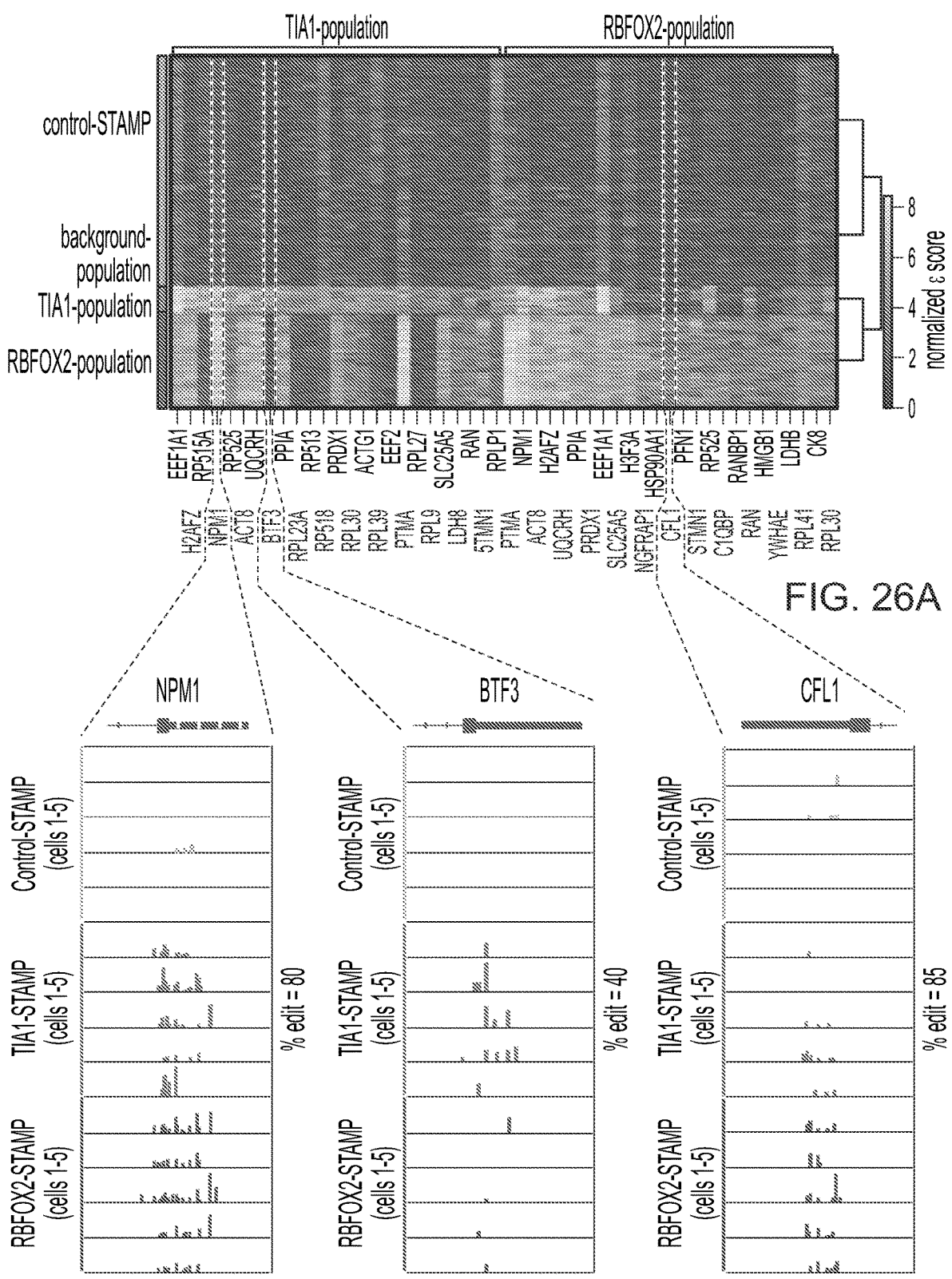

FIG. 26A shows a heatmap of normalized ε score signatures for RBFOX2- and TIA1-population cells compared to control-STAMP and background cells on the top 25 differentially edited gene targets.

FIG. 26B shows IGV browser tracks showing SAILOR quantified edit fractions for the top 5 control-, RBFOX2-, and TIA1-STAMP cells (ranked by summed ε scores) on the NPM1, BTF3 and CFL1 gene targets where results show individual cell edit enrichments were specific to TIA1-STAMP on the BTF3 target gene, and to RBFOX2-STAMP on the CFL1 target gene.

FIG. 26C shows motif enrichment using HOMER from ≥0.99 confidence edits from combined RBFOX2-cluster and control-STAMP cells.

Figures 27A, 27B:
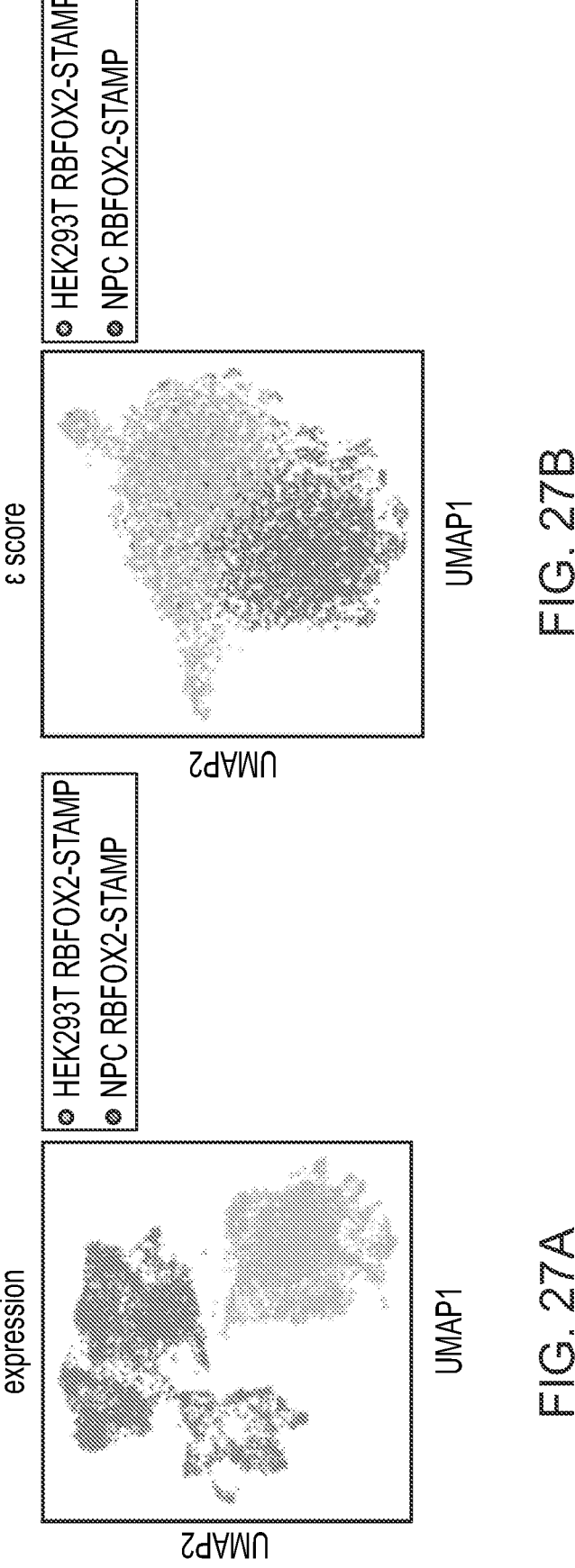

FIG. 27A shows a UMAP analysis of merged 72-hour high-induction RBFOX2-STAMP mixed NPC and HEK293T cells clustered by expression. Results show that cells clustered by gene expression into distinct HEK293T and NPC subgroups expressing cell-type specific markers.

FIG. 27B shows a UMAP analysis as in FIG. 27A using ε score.

Figures 28A, 28B:
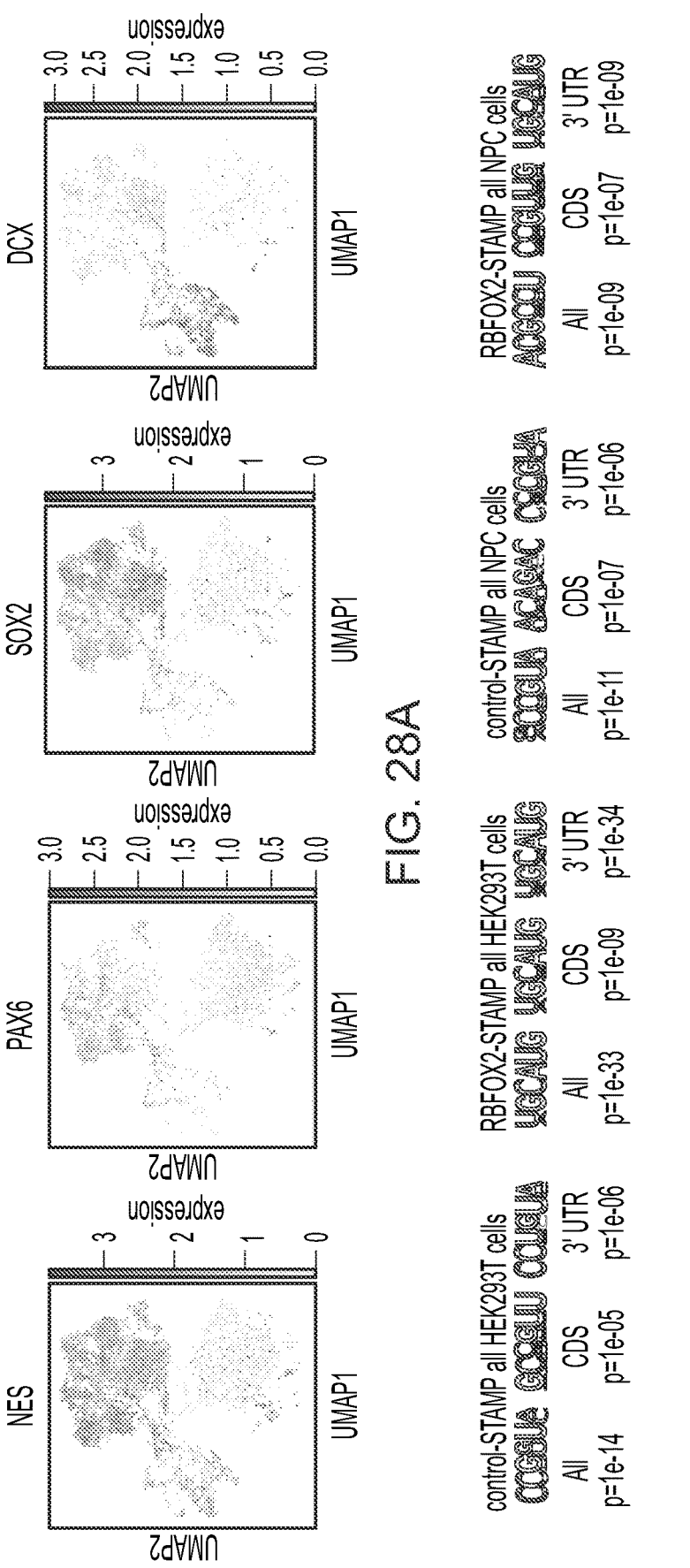

FIG. 28A shows UMAP plots showing expression of neural precursor cell markers NES, PAX6, SOX2 and DCX.

FIG. 28B shows motif enrichment using HOMER from ≥0.99 confidence edits from combined control- and RBFOX2-STAMP HEK293T and NPC cells.

FIG. 29A shows ε score distribution summarized by violin plot for HEK293T and NPC defined cell populations for the top differentially edited genes, where analysis of the top RBFOX2-STAMP differentially edited genes between cell types revealed cell-type specific targets.

FIG. 29B shows violin plots as in FIG. 29A summarizing expression rather than ε score. Results indicate cell-type specific RNA protein interactions independent of target expression levels.

FIG. 29C shows IGV browser tracks showing edit fractions and read coverage for the top 5 control- and RBFOX2-STAMP cells (ranked by summed ε scores) on the RPL14 and RPL13A gene targets. Results indicate that cell type-specific targets and binding sites can be extracted from RBFOX2-STAMP edit signatures by scRNA-seq within a mixture of heterogeneous cell types.

FIG. 30A shows UMAP analysis of EPKM for 72-hour high-induction RPS2-STAMP, control-STAMP where results indicate whether Ribo-STAMP can quantify ribosome association at the single-cell level.

FIG. 30B shows UMAP analysis of cells shown in FIG. 30A with EPKM Louvain clustering into background-population and RPS2-population.

FIG. 31A shows genome-wide comparison of CDS+3'UTR EPKM values for bulk and single-cell EPKM-derived RPS2-population.

FIG. 31B shows comparison of EPKM-derived RPS2-population CDS and CDS+3'UTR EPKM values.

FIG. 31C shows comparison of EPKM-derived RPS2-population total mRNA RPKM values with total mRNA RPKM values from polysome-seq input.

FIG. 31D shows comparison of EPKM-derived RPS2-population CDS+3'UTR EPKM values with total mRNA RPKM values from polysome-seq input.

FIG. 32A shows comparison of EPKM-derived RPS2-population CDS+3'UTR EPKM values with poly-ribosome-fraction-enriched polysome-seq RPKM values. Results show that single-cell Ribo-STAMP edit enrichments are more closely associated with ribosome occupancy than with transcript abundance, demonstrating that single-cell Ribo-STAMP, like single-cell RBP-STAMP, recapitulates results from bulk experiments and correlates well with standard measurements from orthogonal bulk approaches.

FIG. 32B shows a UMAP plot indicated by ε score Louvain clustering into background-cluster, RBFOX2-cluster, TIA1-cluster, and RPS2-cluster from merged 72-hour high-induction STAMP experiments.

FIG. 33A shows UMAP analysis of ε score from merged 72-hour high-induction RPS2-STAMP, control-STAMP and mixed-cell RBFOX2:TIA1-STAMP single-cell experiments.

FIG. 33B shows a UMAP plot as in FIG. 33A with only capture sequence RBFOX2-STAMP and TIA1-STAMP cells highlighted.

FIG. 33C shows individual cell barcode overlap for EPKM-derived and ε score-derived RPS2-populations.

Figure 34B:
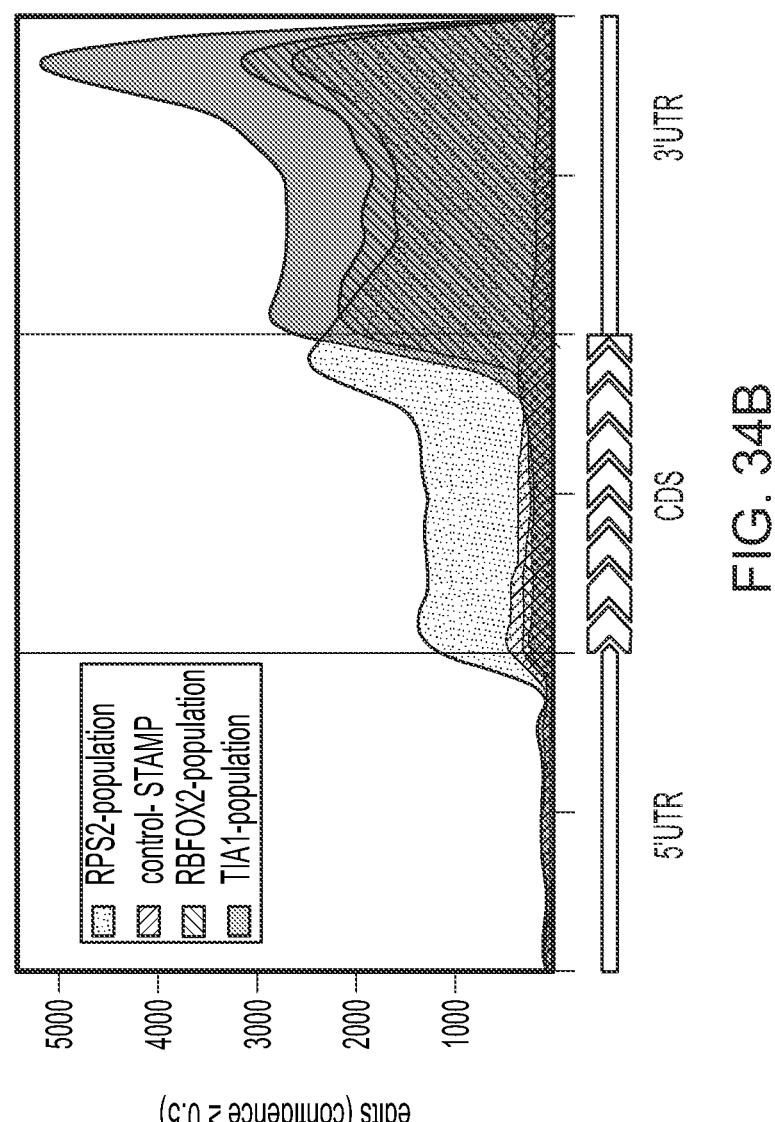
Figure 34A:
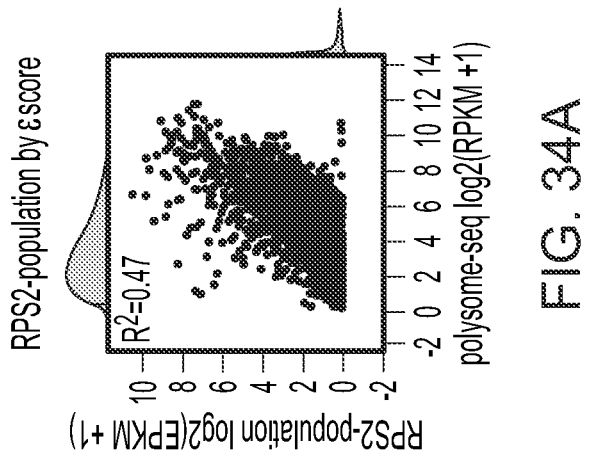

FIG. 34A shows comparison of ε score derived RPS2-population CDS+3'UTR EPKM values with poly-ribosome-fraction-enriched polysome-seq RPKM values.

FIG. 34B shows a metagene plot showing distribution for aggregate cell edits (≥0.5 confidence level) from control-STAMP, RPS2-cluster, TIA1-cluster, and RBFOX2-cluster cells across 5'UTR, CDS and 3'UTR gene regions for the top quartile of ribosome occupied genes (ribo-seq, n=4,931 genes). Results demonstrated CDS enrichment for single-cell RPS2-STAMP edits compared to more 3'UTR-centric enrichment for single-cell RBFOX2- and TIA1-STAMP.

Figures 35A, 35B:
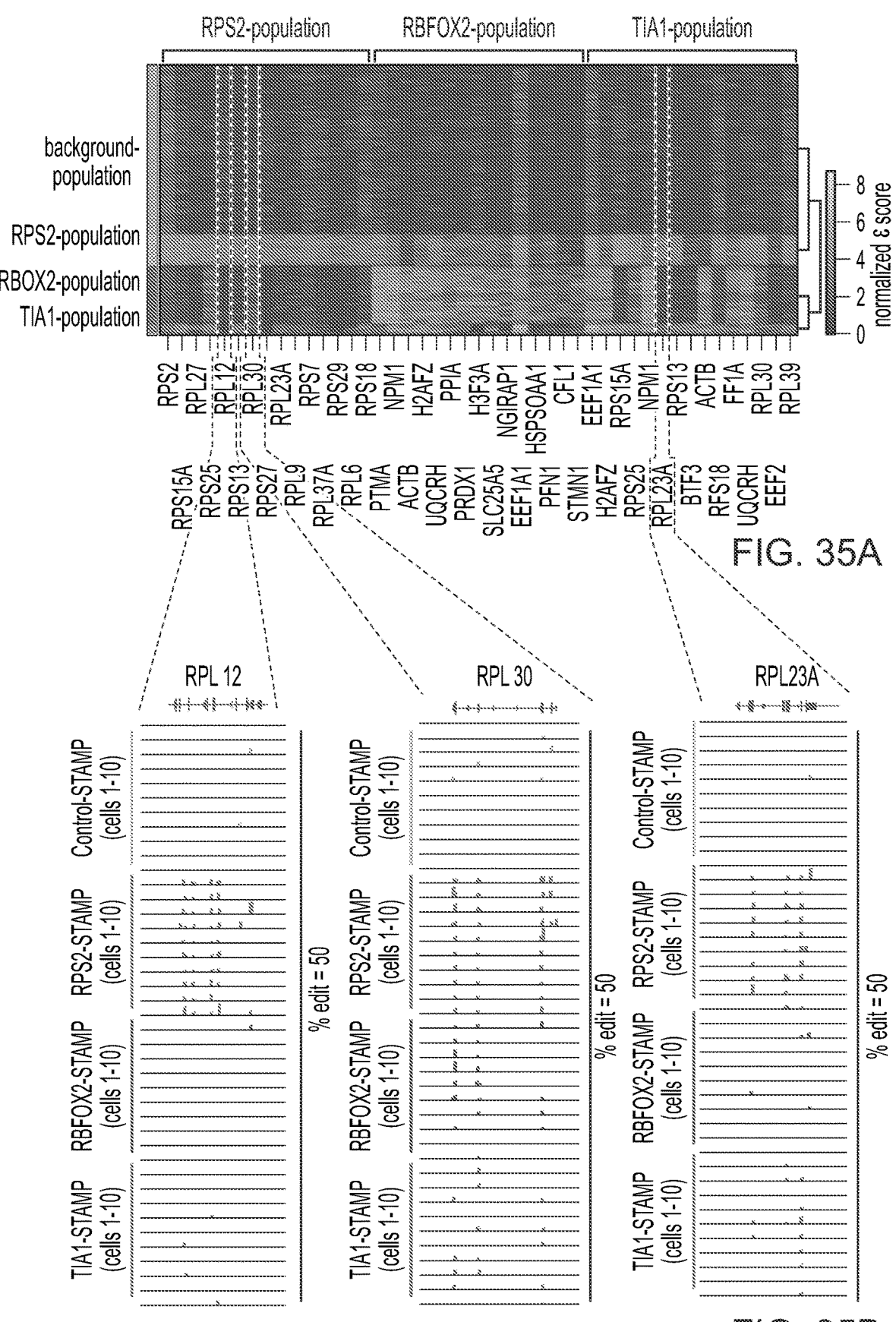

FIG. 35A shows a heatmap of normalized ε score signatures for RPS2-population, RBFOX2-population, and TIA1-population cells compared to background cells on the top 15 differentially edited gene targets.

FIG. 35B shows IGV browser tracks showing edit fractions for the top 10 control-, RPS2-, RBFOX2-, and TIA1-STAMP cells (ranked by summed ε scores) on the RPL12, RPL30 and RPL23A gene targets. Results demonstrate the capacity of STAMP to reveal RBP targets and ribosome association in parallel at single-cell resolution.

Figures 36A, 36B:
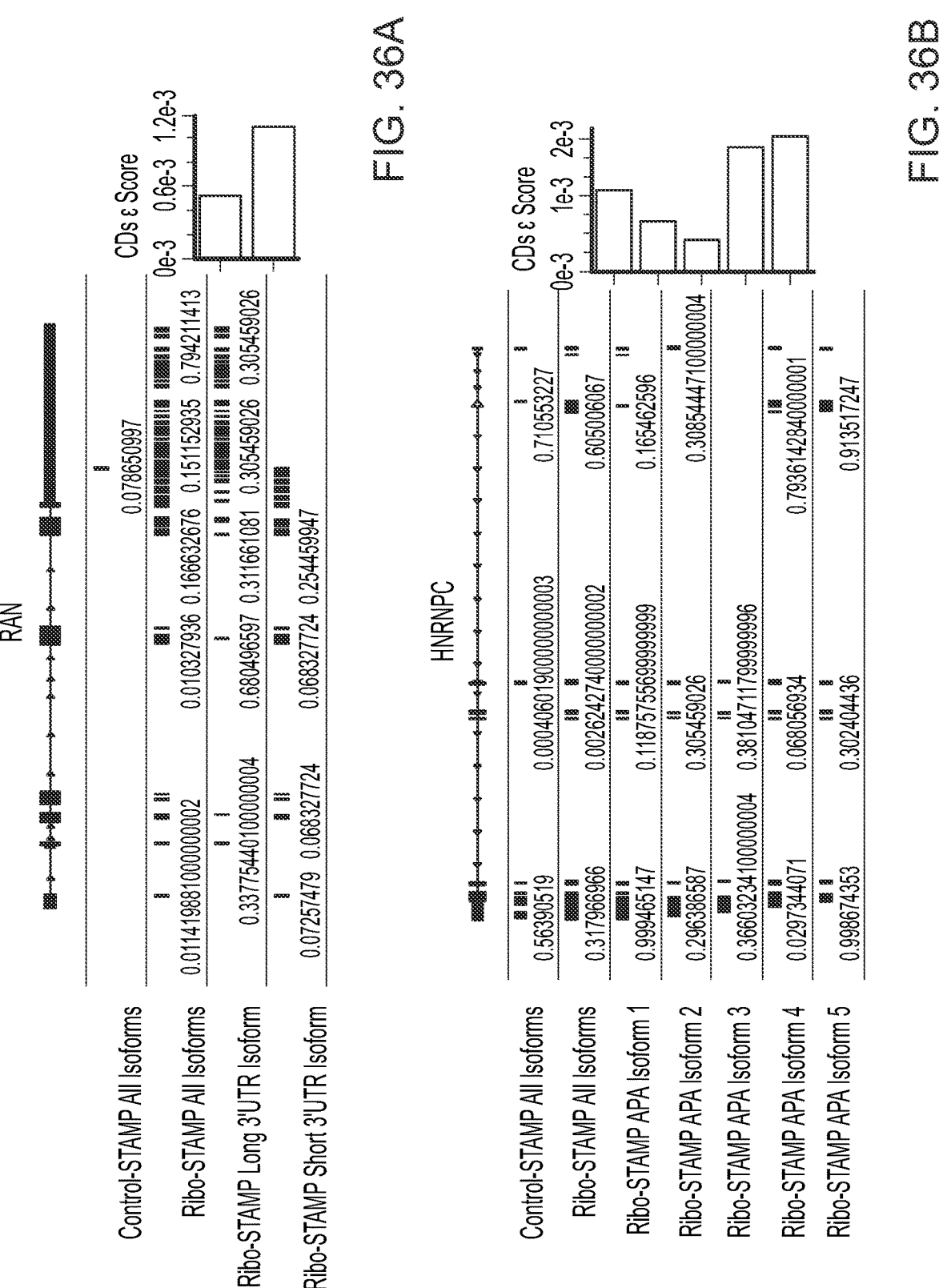

FIG. 36A shows IGV tracks showing control- and Ribo-STAMP edits with associated confidence scores from longreads (PacBio) across all isoforms and Ribo-STAMP edits on individual alternative polyadenylation (APA) isoforms for RAN example genes. The bar charts show Ribo-STAMP ε scores across the coding sequence (CDS) region for each APA isoform.

FIG. 36B shows IGV tracks showing control- and Ribo-STAMP edits with associated confidence scores from longreads (PacBio) across all isoforms and Ribo-STAMP edits on individual alternative polyadenylation (APA) isoforms for HNRNPC example genes. The bar charts show Ribo-STAMP ε scores across the coding sequence (CDS) region for each APA isoform. Results demonstrate long-read Ribo-STAMP shows isoform specific ribosome binding profiles.

DETAILED DESCRIPTION

This disclosure describes chimeric protein compositions and uses for chimeric proteins to enable RNA modifications that can be detected by sequencing methods as a surrogate measure for ribosome initiation, scanning, elongation and release.

RNA Binding Protein

RNA binding proteins (RBPs) are proteins that bind to the double or single stranded RNA in cells and have important roles in cellular processes (e.g., cellular transport, or localization). RBPs also play a role in post-transcriptional control of RNAs, such as RNA splicing, polyadenylation, mRNA stabilization, mRNA localization, and translation. In some embodiments, an RBP is a cytoplasmic protein. The term "RNA binding protein" can refer to a protein that interacts with RNA molecules (e.g., mRNA) from synthesis to decay to affect their metabolism, localization, stability, and translation. In some embodiments, an RBP is a nuclear protein. In some embodiments, RBPs can include, but are not limited to, splicing factors, RNA stability factors, histone stem-loop binding proteins, or ribosomes. For example, a eukaryotic ribosome can include a collection of RBPs that can interact directly with mRNA coding sequences.

In some embodiments, an RNA binding protein comprises a ribosomal protein, wherein the ribosomal protein binds to a ribosome and an mRNA during translation. In some embodiments, an RNA binding protein comprises a ribosomal protein, wherein the ribosomal protein binds to a ribosome or an mRNA during translation. In some embodiments, the RNA binding protein comprises at least one of: RBFOX1 (A2BP1), RBFOX2 (RBM9), RBFOX3 (NeuN), SLBP, RBM5, RBM6, PRBP1, ACO1, Adat1, PCBP1, PCBP2, PCBP3, PCBP4, RBM3, RBM4, RBM5, RBM6, and APOBEC1.

As used herein, "ribosomal protein" can refer to a protein that is present in a ribosome (e.g., a mammalian ribosome) or a protein that binds to a ribosome and an mRNA during translation (e.g., a translation initiation factor, a translation elongation factor, and a translation termination factor). In some embodiments, the ribosomal protein binds to a ribosome or an mRNA during translation. The term "translation initiation factor" can refer to a protein that binds to a ribosome, a subunit of a ribosome, and/or an mRNA during the start of translation of an mRNA. The term "translation elongation factor" can refer to a protein that binds to a ribosome, a subunit of a ribosome, and/or mRNA during translation of an mRNA. The term "translation termination factor" can refer to a protein that binds to a ribosome, a subunit or a ribosome, and/or mRNA during cessation of translation and/or release of an mRNA from a ribosome or a subunit of a ribosome. In a ribosome, ribosomal proteins can participate in the translation process and binding of translation factors (e.g., translation initiation factor, translation elongation factor, translation termination factor). In some embodiments, the ribosomal protein is selected from the group consisting of: RPS2, RPS3, RPS3A, RPS4X, RPS4Y1, RPS4Y2, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS28, RPS29, RPS30, RSSA, RACK1, RPL3, RPL4, RPL5, RPL6, RPL7A, RPL7, RPL8, RPL9, RPL10A, RPL10, RPL11, RPL12, RPL13A, RPL13, RPL14, RPL15, RPL17, RPL18A, RPL18, RPL19, RPL21, RPL22, RPL23A, RPL23, RPL24, RPL26, RPL27A, RPL27, RPL28, RPL29, RPL30, RPL31, RPL32, RPL34, RPL35A, RPL35, RPL36, RPL37A, RPL37, RPL38, RPL39, RPL40, RPL41, RPLA0, RPLA1, and RPLA2. In some embodiments, the ribosomal protein is a translation initiation factor. In some embodiments, the ribosomal protein is a translation elongation factor. In some embodiments, wherein the ribosomal protein is a translation termination factor.

RNA Modification

As used herein, "nucleic acid" is used to include any compound and/or substance that comprise a polymer of nucleotides. In some embodiments, a polymer of nucleotides are referred to as polynucleotides. Exemplary nucleic acids or polynucleotides can include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof. Naturally-occurring nucleic acids generally have a deoxyribose sugar (e.g., found in deoxyribonucleic acid (DNA)) or a ribose sugar (e.g., found in ribonucleic acid (RNA)).

A nucleic acid can contain nucleotides having any of a variety of analogs of these sugar moieties that are known in the art. A deoxyribonucleic acid (DNA) can have one or more bases selected from the group consisting of adenine (A), thymine (T), cytosine (C), or guanine (G), and a ribonucleic acid (RNA) can have one or more bases selected from the group consisting of uracil (U), adenine (A), cytosine (C), or guanine (G).

As used herein, "nucleoside" is used to include nucleotides without a phosphate group. A nucleoside comprises a nucleobase (e.g., nitrogenous base) and a five-carbon sugar ribose, and a nucleotide comprises a nucleobase, a five-carbon sugar, and one or more phosphate groups. For example, a nucleoside can be a cytidine, uridine, guanosine, thymidine, or inosine.

In some embodiments, the nucleic acid is a messenger RNA (mRNA). As used herein, "messenger RNA" (mRNA) can refer to any polynucleotide which encodes a polypeptide of interest and which is capable of being translated to produce the encoded polypeptide of interest in vitro, in vivo, in situ, or ex vivo.

Provided herein are methods of determining a relative translation rate of a target mRNA in a cell, the method comprising: introducing into the cell a chimeric protein comprising: an RNA binding protein and an RNA editing protein; determining a plurality of nucleotide substitutions introduced into the target mRNA by the RNA editing protein; and comparing the determined plurality of nucleotide substitutions introduced into the target mRNA to a plurality of nucleotide substitutions introduced into other non-target mRNAs in the cell, thereby determining the relative translation rate of the target mRNA in the cell. As used herein, "relative translation rate" means the relative level of translation of a target mRNA in a cell as compared to the translation of other non-target mRNAs in the cell over the same amount of time, as determined using the same or a similar assay.

Also provided herein are methods of determining an RNA binding protein binding site of a target mRNA in a cell, the method comprising: introducing into the cell a chimeric protein comprising (i) an RNA binding protein or a fragment thereof and (ii) an RNA editing protein or a fragment thereof; determining a plurality of nucleotide substitutions introduced into the target mRNA by the RNA editing protein or fragment thereof; and identifying a region on the target mRNA where the plurality of nucleotide substitutions are introduced into the target mRNA, thereby determining the RNA binding protein binding site wherein the RNA binding protein binds to the target mRNA in the cell.

In some embodiments, a nucleotide substitution is a point mutation, wherein a single nucleotide of a nucleic acid (e.g., DNA, RNA, or mRNA) is substituted. In some embodiments, the nucleotide substitution includes a transition, wherein a purine (e.g., adenine (A) or guanine (G)) is substituted with a purine, or a pyrimidine (e.g., cytosine (C), thymine (T), or uracil (U)) is substituted with a pyrimidine.

In some embodiments, the nucleotide substitution includes a transversion, wherein a purine is substituted for a pyrimidine, or a pyrimidine is substituted for a purine. In some embodiments, the nucleotide substitution includes nucleobase modifications such as cytidine (C) to uridine (U) deamination. In some embodiments, the nucleotide substitution includes nucleobase modifications such as adenosine (A) to inosine (I) deamination. In some embodiments, the nucleotide substitution includes nucleobase modifications such as adenosine (A) to guanine (G) deamination.

As used herein, "RNA editing protein" can refer to an enzyme that catalyzes a reaction that results in a detectable chemical modification of a nucleotide present in an RNA (e.g., an mRNA). RNA editing may include the insertion, deletion, and base substitution of nucleotides within the RNA molecule. In some embodiments, the RNA editing protein is an engineered enzyme. In some embodiments, the RNA editing protein is a modification of a natural enzyme. For example, RNA editing may include nucleobase modifications such as cytidine (C) to uridine (U) and adenosine (A) to inosine (I) or guanine (G) deaminations (FIG. 1). In some embodiments, the RNA editing protein is a cytidine deaminase which converts cytidine (C) to uridine (U). In some embodiments, the cytidine deaminase is an apolipoprotein B mRNA editing enzyme, catalytic polypeptide-like (APOBEC) protein. In some embodiments, the APOBEC protein is selected from the group consisting of: APOBEC1, APOBEC2, APOBEC3A, APOBEC3B, APOBEC3C, APOBEC3D, APOBEC3F, APOBEC3G, APOBEC3H, and APOBEC4. In some embodiments, the RNA editing protein is an adenosine deaminase which converts adenosine (A) to inosine (I) or guanine (G). In some embodiments, the adenosine deaminase is an adenosine deaminase acting on RNA (ADAR). In some embodiments, the adenosine deaminase is an adenosine aminohydrolase (ADA). In some embodiments, the adenosine deaminase is an adenosine deaminase acting on tRNA (ADAT). In some embodiments, the conversion of nucleotides by the RNA binding protein can be non-natural.

In some embodiments, the RNA editing protein is a plant RNA editing protein, wherein the plant RNA editing protein converts cytidine (C) to uridine (U). In some embodiments, the plant RNA editing protein can be used in human and/or mammalian cells. In some embodiments, an RNA editing protein in human and/or mammalian cells can be used in plant cells.

Chimeric Protein

As used herein, "chimeric protein" can refer to a polypeptide consisting of one or more domains from different proteins or mutations within a single protein giving the characteristics of another protein. A chimeric protein can be a polypeptide made by a combination (e.g., fusion) of two otherwise separated segments of amino acid sequences. For example, a chimeric protein can include a RNA binding protein and an RNA editing protein. In some embodiments, a chimeric protein includes an RNA binding protein, and RNA editing protein, and a ribosomal protein. In some embodiments, the ribosomal protein is a ribosomal subunit. In some embodiments, a chimeric protein includes two or more ribosomal subunits.

In some embodiments, the RNA binding protein is a full-length RNA binding protein. In some embodiments, the ribosomal protein is a full-length ribosomal protein. In some embodiments, the ribosomal protein is a subunit of the ribosomal protein. In some embodiments, the RNA binding protein is RBFOX2. In some embodiments, the RNA editing protein is APOBEC1.

As used herein, "full-length protein" can refer to a protein derived from a single nucleotide sequence without elimination or truncation of the N- or C-terminal portion of the protein. In some embodiments, a single gene that encodes a full-length protein can also produce protein isoforms. As used herein, "isoform" can refer to a member of a set of proteins that originate from a single gene or gene family. In some embodiments, an isoform can be formed from alternative splicing of a single gene. In some embodiments, an isoform can be formed from post-transcriptional modifications of a single gene. In some embodiments, a protein is a protein subunit. As used herein, "subunit of a protein" can refer to a single protein molecule that assembles with other protein molecules to form a protein complex. In some embodiments, a protein complex can be composed of more than one subunit. For example, a ribosomal protein can be a ribosomal subunit involved in the cellular process of translation.

In some embodiments, the chimeric protein comprises a single polypeptide. In some embodiments, the RNA editing protein and the ribosomal protein directly abut each other in the single polypeptide. In some embodiments, the single polypeptide further comprises a linker disposed between the RNA editing protein and the ribosomal protein. In some embodiments, the RNA editing protein is N-terminally positioned relative to the ribosomal protein in the single polypeptide. In some embodiments, the RNA editing protein is C-terminally positioned relative to the ribosomal protein in the single polypeptide.

In some embodiments, the chimeric protein is introduced into a cell. In some embodiments, the nucleic acid encoding the chimeric protein is introduced into the cell. In some embodiments, the nucleic acid encoding the chimeric protein is introduced into the cell by transfection (e.g., using transfectamine, cationic polymers, calcium polymers, calcium phosphate, or electroporation). In some embodiments, the chimeric protein is introduced into a cell by virus-mediated DNA transfer. In some embodiments, the chimeric protein is introduced into a cell by transduction (e.g., using a bacteriophage or recombinant viral vector). In some embodiments, the chimeric protein is introduced into a cell by mechanical delivery (e.g., magnetic beads). In some embodiments, the chimeric protein is introduced into a cell by transporter proteins. In some embodiments, the nucleic acid is present in an expression vector. For example, an expression vector can include a promoter sequence operably linked to the sequence encoding the molecule (e.g., a nucleic acid molecule). Non-limiting examples of expression vectors include plasmid vectors, transposon vectors, cosmid vectors, and viral derived vectors (e.g., any adenoviral derived vectors (AV), cytomegaloviral derived (CMV) vectors, simian viral derived (SV40) vectors, adeno-associated virus (AAV) vectors, lentivirus vectors, and retroviral vectors). In some embodiments, the expression vector is a viral vector. In some embodiments, the viral vector is a lentiviral vector.

In some embodiments, the chimeric protein is a multi-chain polypeptide. In some embodiments, the multi-chain polypeptide comprises a first polypeptide comprising the RNA editing protein and a second polypeptide comprising the ribosomal protein. In some embodiments, the first polypeptide further comprises a first dimerization domain, and the second polypeptide further comprises a second dimerization domain, and the first and second dimerization domains specifically bind to each other. In some embodiments, the chimeric polypeptide comprises a first polypeptide comprising the RNA editing protein connected through a chemical group to a second polypeptide comprising the ribosomal protein. In some embodiments, the chemical group is a disulfide bond, a thioether bond, and a 1, 4 cycloaddition product.

STAMP

Surveying targets by APOBEC mediated profiling (STAMP) is a method of efficiently detecting RBP-RNA interaction, and identifying RBP- and cell type-specific RNA-protein interactions, by using a chimeric protein including an RNA binding protein and RNA editing protein. In previous applications and publications, STAMP has also been referred to as Target by RBP-APOBEC C-to-U Editing (TRACE). STAMP is an integrated experimental and computational framework which demonstrates the discovery of RBP-RNA binding sites, including isoform-specific binding sites, at single-cell resolution. In some embodiments, STAMP is performed with computational methods that de-multiplex multiple RBPs by clustering cells using only edit signatures, allowing deconvolution of targets for multiplexed RBPs, and the cell-type specific binding of an RBP in a heterogenous mixtures of cell-types. STAMP allows for reproducible and quantitative identification of RBP-RNA binding sites, including isoform-specific binding sites. Further, STAMP can be used to determine a relative translation rate of an mRNA at single-cell resolution and in a heterogenous mixture of cell-types. In some embodiments, STAMP can be used to examine translational landscapes at a single cell resolution. In some embodiments, STAMP can be used with specific ribosome subunits, wherein gene expression can be measured simultaneously with detection of ribosome association.

In some embodiments, STAMP can identify cell-type specific RBP binding sites. In some embodiments, STAMP can identify multiple RBP binding sites for different RBPs in a single cell type. In some embodiments, STAMP can identify multiple RBP binding sites for different RBPs in multiple cell types. In some embodiments, STAMP can identify isoform-specific RBP binding sites. In some embodiments, STAMP and long-read sequencing can be used to identify isoform-specific RBP target sites. In some embodiments, STAMP can identify binding sites of full-length RBPs by C-to-U RNA editing. In some embodiments, STAMP can identify binding sites on single-stranded RNA targets. In some embodiments, STAMP provides a method for cell-type specific and multiplexed-RBP target identification in single cells. In some embodiments, STAMP can identify mammalian cell-type specific RBP binding sites. In some embodiments, STAMP can identify plant cell-type specific RBP binding sites. In some embodiments, STAMP can identify bacterial cell-type specific RBP binding site.

In some embodiments, STAMP can identify microRNA targets. In some embodiments, an Arogonaute (AGO) protein can be fused to an RNA editing protein (e.g., APOBEC), wherein the AGO protein is an RBP that binds with microRNAs thereby recognizing microRNA targets. In some embodiments, STAMP can identify RNA-DNA duplexes. In some embodiments, an RNaseH proteins can be fused to an RNA editing protein (e.g., APOBEC), wherein the RNaseH protein recognizes RNA-DNA duplexes in cells.

In some embodiments, STAMP provides a method for antibody-free detection of RBP by standard RNA sequencing. In some embodiments, STAMP provides a method for antibody-free detection of ribosome interactions with a target RNA. In some embodiments, STAMP provides a method for identifying RBP- and cell type-specific RNA-protein interactions without using immunoprecipitation. In some embodiments, STAMP demonstrates specificity for full-length RBPs that bind polyadenylated mRNAs (e.g., RBFOX2, TIA1). In some embodiments, STAMP demonstrates specificity for full-length RBPs that bind non-polyadenylated mRNAs (e.g., SLBP).

In some embodiments, STAMP is performed using with ribosome subunits. As used herein, "ribosome-subunit STAMP" (Ribo-STAMP) refers to a chimeric protein, wherein the chimeric protein includes an RNA binding protein, and a ribosome subunit, wherein the ribosome subunit is fused to the RNA editing protein. In some embodiments, Ribo-STAMP uses small ribosomal subunits to measure transcriptome-wide ribosome association in single cells. In some embodiments, Ribo-STAMP can be used to simultaneously measure ribosome association and gene expression. In some embodiments, ribosome association and gene expression can be examined in a single-cell, in a homologous cell population, or in a heterologous cell population. In some embodiments, Ribo-STAMP allows mRNA editing while identifying ribosome association with the mRNA, and also distinguishes genes with varying levels of ribosome occupancy. In some embodiments, Ribo-STAMP uses edited and non-edited reads to reflect ribosome-associated and input gene expression values simultaneously. In some embodiments, the simultaneous readouts can be used in complex and heterogenous cellular or in vivo models to address cell identity or disease states.

In some embodiments, the ribosomal subunit is fused to the RNA editing protein (e.g., APOBEC1) of the chimeric protein. In some embodiments, two or more ribosomal subunits are fused to the RNA editing protein of the chimeric protein. In some embodiments, the ribosomal subunit includes RPS2 or RPS3.

Analysis of RNA Modification

A wide variety of different sequencing methods can be used to analyze and determine the number of nucleotide substitutions introduced into a target mRNA by an RNA editing protein. Sequencing of polynucleotides can be performed by various methods. For example, methods for sequencing polynucleotides include, but are not limited to, nucleic acid amplification, polymerase chain reaction (PCR), isothermal amplification, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, microarray methods, targeted sequencing, single molecule real-time sequencing, and any combinations thereof.

In some embodiments, the number of nucleotide substitutions introduced into a target mRNA by a RNA editing protein is analyzed by sequencing the target mRNA. In some embodiments, the sequencing of the target mRNA is performed using single cell nucleic acid sequencing. In some embodiments, the sequencing of the target mRNA is performed using long-read sequencing. In some embodiments, the target mRNA is a full-length mRNA isoform. In some embodiments, the target mRNA can have a total length of 1 nucleotide to about 150 nucleotides (e.g., 1 nucleotide to about 125 nucleotides, 1 nucleotide to about 100 nucleotides, 1 nucleotide to about 90 nucleotides, 1 nucleotide to about 80 nucleotides, 1 nucleotide to about 70 nucleotides, 1 nucleotide to about 60 nucleotides, 1 nucleotide to about 50 nucleotides, 1 nucleotide to about 40 nucleotides, 1 nucleotide to about 30 nucleotides, 1 nucleotide to about 20 nucleotides, 1 nucleotide to about 10 nucleotides, 1 nucleotide to about 5 nucleotides, about 5 nucleotides to about 150 nucleotides, about 5 nucleotides to about 150 nucleotides, about 5 nucleotides to about 125 nucleotides, about 5 nucleotides to about 100 nucleotides, about 5 nucleotides to about 90 nucleotides, about 5 nucleotides to about 80 nucleotides, about 5 nucleotides to about 70 nucleotides, about 5 nucleotides to about 60 nucleotides, about 5 nucleotides to about 50 nucleotides, about 5 nucleotides to about 40 nucleotides, about 5 nucleotides to about 30 nucleotides, about 5 nucleotides to about 20 nucleotides, about 5 nucleotides to about 10 nucleotides, about 10 nucleotides to about 150 nucleotides, about 10 nucleotides to about 125 nucleotides, about 10 nucleotides to about 100 nucleotides, about 10 nucleotides to about 90 nucleotides, about 10 nucleotides to about 80 nucleotides, about 10 nucleotides to about 70 nucleotides, about 10 nucleotides to about 60 nucleotides, about 10 nucleotides to about 50 nucleotides, about 10 nucleotides to about 40 nucleotides, about 10 nucleotides to about 30 nucleotides, about 10 nucleotides to about 20 nucleotides, about 20 nucleotides to about 150 nucleotides, about 20 nucleotides to about 125 nucleotides, about 20 nucleotides to about 100 nucleotides, about 20 nucleotides to about 90 nucleotides, about 20 nucleotides to about 80 nucleotides, about 20 nucleotides to about 70 nucleotides, about 20 nucleotides to about 60 nucleotides, about 20 nucleotides to about 50 nucleotides, about 20 nucleotides to about 40 nucleotides, about 20 nucleotides to about 30 nucleotides, about 30 nucleotides to about 150 nucleotides, about 30 nucleotides to about 125 nucleotides, about 30 nucleotides to about 100 nucleotides, about 30 nucleotides to about 90 nucleotides, about 30 nucleotides to about 80 nucleotides, about 30 nucleotides to about 70 nucleotides, about 30 nucleotides to about 60 nucleotides, about 30 nucleotides to about 50 nucleotides, about 30 nucleotides to about 40 nucleotides, about 40 nucleotides to about 150 nucleotides, about 40 nucleotides to about 125 nucleotides, about 40 nucleotides to about 100 nucleotides, about 40 nucleotides to about 90 nucleotides, about 40 nucleotides to about 80 nucleotides, about 40 nucleotides to about 70 nucleotides, about 40 nucleotides to about 60 nucleotides, about 40 nucleotides to about 50 nucleotides, about 50 nucleotides to about 150 nucleotides, about 50 nucleotides to about 125 nucleotides, about 50 nucleotides to about 100 nucleotides, about 50 nucleotides to about 90 nucleotides, about 50 nucleotides to about 80 nucleotides, about 50 nucleotides to about 70 nucleotides, about 60 nucleotides to about 150 nucleotides, about 60 nucleotides to about 125 nucleotides, about 60 nucleotides to about 100 nucleotides, about 60 nucleotides to about 90 nucleotides, about 60 nucleotides to about 80 nucleotides, about 60 nucleotides to about 70 nucleotides, about 70 nucleotides to about 150 nucleotides, about 70 nucleotides to about 125 nucleotides, about 70 nucleotides to about 100 nucleotides, about 70 nucleotides to about 90 nucleotides, about 70 nucleotides to about 80 nucleotides, about 80 nucleotides to about 150 nucleotides, about 80 nucleotides to about 125 nucleotides, about 80 nucleotides to about 100 nucleotides, about 80 nucleotides to about 90 nucleotides, about 90 nucleotides to about 150 nucleotides, about 90 nucleotides to about 125 nucleotides, about 90 nucleotides to about 100 nucleotides, about 100 nucleotides to about 150 nucleotides, about 100 nucleotides to about 125 nucleotides, or about 125 nucleotides to about 150 nucleotides). In some embodiments, the mRNA can have a total length of longer than 100 nucleotides (e.g., longer than 125 nucleotides, longer than 150 nucleotides, longer than 200 nucleotides, longer than 250 nucleotides, longer than 500 nucleotides, longer than 750 nucleotides, longer than 1000 nucleotides, longer than 1250 nucleotides, longer than 1500 nucleotides, longer than 1750 nucleotides, longer than 2000 nucleotides, longer than 3000 nucleotides, longer than 4000 nucleotides, longer than 5000 nucleotides, longer than 6000 nucleotides, longer than 7000 nucleotides, longer than 8000 nucleotides, longer than 9000 nucleotides, or longer than 10,000 nucleotides).

In some embodiments, other non-target mRNAs in the cell are sequenced, and the translation rate of the target mRNA is compared to the translation rate of another, non-target mRNA in the cell to determine the relative translation rate of the target mRNA in the cell. In some embodiments, the number of nucleotide substitutions introduced into a target mRNA by a RNA editing protein is compared to the number of nucleotide substitutions introduced into other, non-target mRNAs in the cell. In some embodiments, the number of nucleotide substitutions introduced into the target mRNA by a RNA editing protein is compared to the number of nucleotide substitutions introduced into the same target mRNA in another cell expressing only he RNA editing protein (e.g., APOBEC1) as a control, wherein the relative translation efficiency of the target mRNA in the cell is determined.

EXAMPLES

The disclosure is further described in the following examples, which do not limit the scope of the disclosure.

Example 1—STAMP Identifies RBP Binding Sites Without Immunoprecipitation

Figures 2A, 2B, 2C:
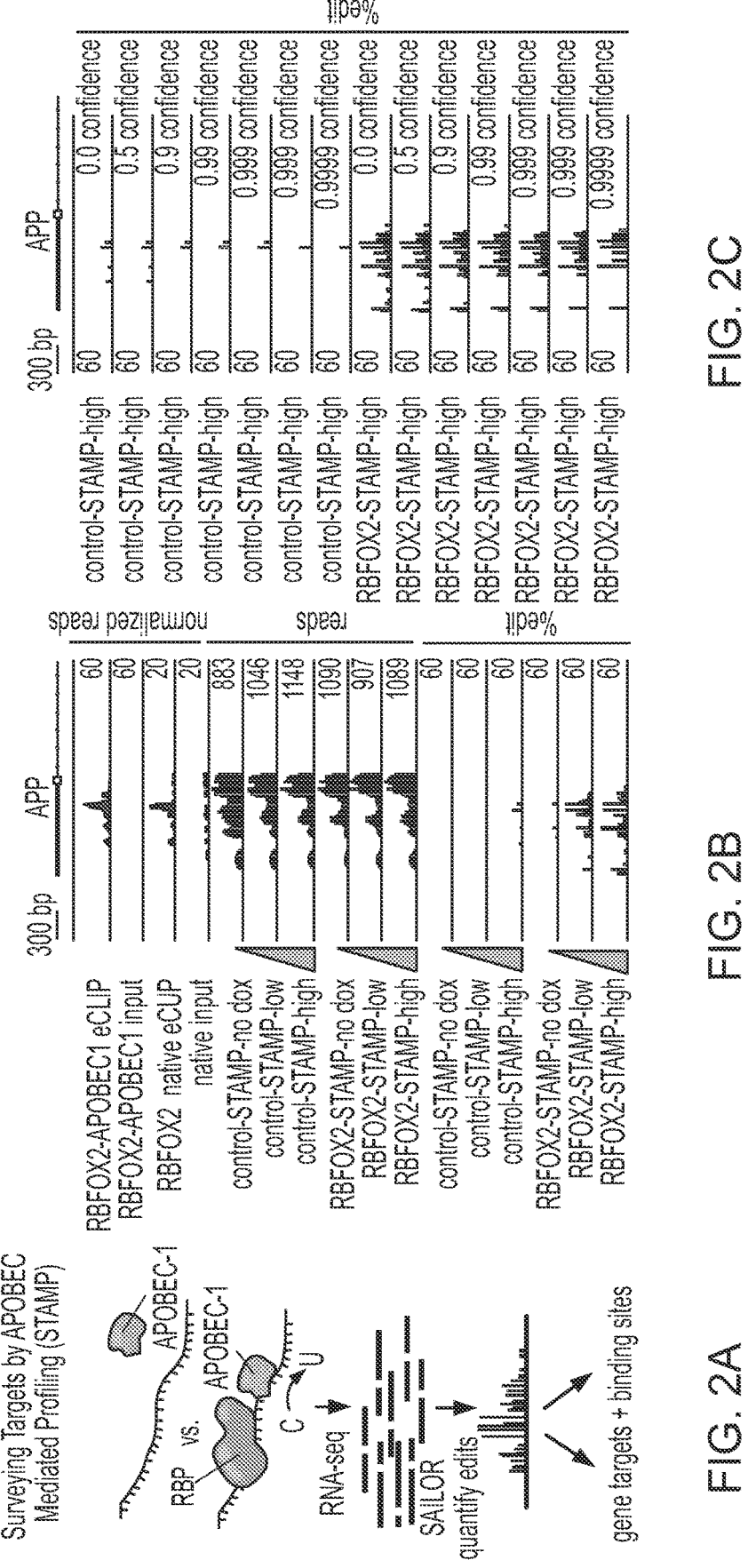
FIG. 2A shows an exemplary schematic showing Surveying Targets by Apobec-Mediated Profiling (STAMP) strategy fusing rat APOBEC1 module to an RBP of interest to deposit edits at or near RBP binding sites. C-to-U mutations from either APOBEC1-only control (control-STAMP) or RBP fusion (RBP-STAMP) can be detected by standard RNA sequencing and quantified using the SAILOR analysis pipeline.
FIG. 2B shows integrative genome viewer (IGV) browser tracks showing RBFOX2 and RBFOX2-APOBEC1 eCLIP peaks on the target gene APP, compared with control- and RBFOX2-STAMP signal and SAILOR quantified edit fraction for increasing induction levels of fusions (doxycycline: 0 ng=none, 50 ng=low, or 1 µg/ml=high, 72 hours). Results show that cells expressing low and higher levels of RBFOX2-STAMP for 72 hours had enriched C-to-U edit clusters on the 3' untranslated region of the known RBFOX2 target APP mRNA.
FIG. 2C shows IGV tracks showing 72-hour high-induction control- and RBFOX2-STAMP signal on the APP target gene at increasing confidence levels. Results demonstrate that fusion of the APOBEC1 module to a well-characterized RBP shows enriched target-specific edits.

Immunoprecipitation-free detection of RBP targets was performed by fusing full-length RBPs of interest to the cytidine deaminase enzyme APOBEC1, which is known to catalyze C-to-U editing on single-stranded RNA targets (FIG. 2A). Upon expression of an RBP-APOBEC1 fusion protein (RBP-STAMP), RBPs direct the deaminase module to their RNA targets leading to C-to-U base conversion proximal to RBP binding sites. These mutations are resolved using high-throughput RNA sequencing approaches and quantified using the SAILOR analysis pipeline, which was modified to identify and assign a confidence value for C-to-U mismatches using a beta distribution that factors both site coverage and editing percentage following removal of annotated hg19 SNPs.

Here, APOBEC1 was fused to the C-terminus of the RBP RBFOX2 and generated stable HEK293T cell lines using lentiviral integration. RBFOX2-STAMP is doxycycline inducible to allow modulation of the duration and magnitude of fusion expression, and no detectable change in cell viability or proliferation rate was noted at any induction level or time point. Cells expressing low (50 ng/ml doxycycline) and higher (1 μg/ml doxycycline) levels of RBFOX2-STAMP for 72 hours had enriched C-to-U edit clusters on the 3' untranslated region (3'UTR) of the known RBFOX2 target APP mRNA, and these edit clusters coincided with reproducible RBFOX2 binding sites as detected by enhanced CLIP (eCLIP) of either endogenous RBFOX2 or the RBFOX2-APOBEC1 fusion (FIG. 2B). Uninduced RBFOX2-STAMP, or control-STAMP (APOBEC1 only) at low and high induction, had few or no detectible C-to-U edits in the same region, indicating target specificity of RBFOX2-APOBEC1. RBFOX2-STAMP induced edits within this APP 3'UTR target region were 10-fold to 25-fold more frequent than background control-STAMP edits at 0.9 and 0.999 (SAILOR) confidence thresholds, respectively (FIG. 2C). These results demonstrate that fusion of the APOBEC1 module to a well characterized RBP produces target-specific edits.

Figure 3:
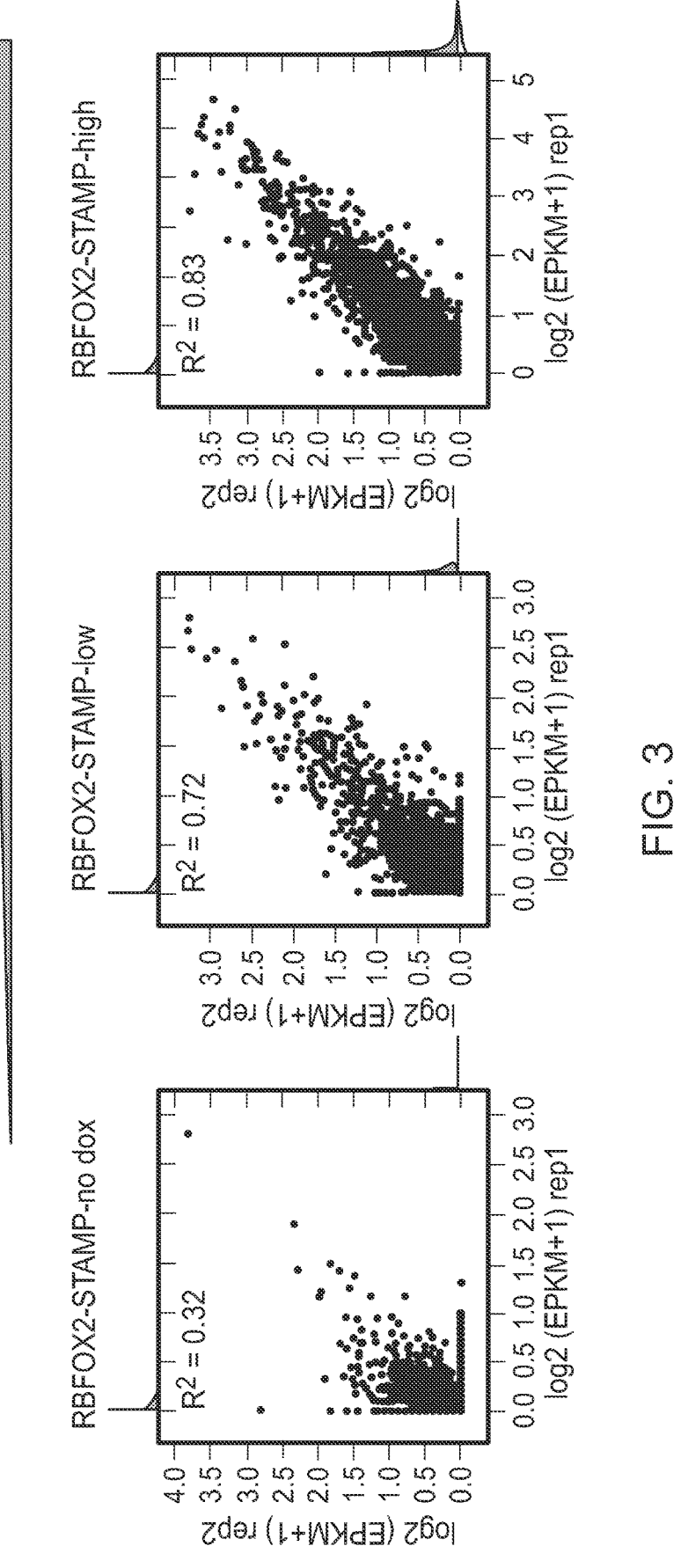
FIG. 3 shows RBFOX2-STAMP replicate correlations for the edited read counts per target normalized for length and coverage (EPKM). Results show the number of edited reads (E) on each target gene were highly reproducible and correlations between replicates improved upon induction.
Figure 4:
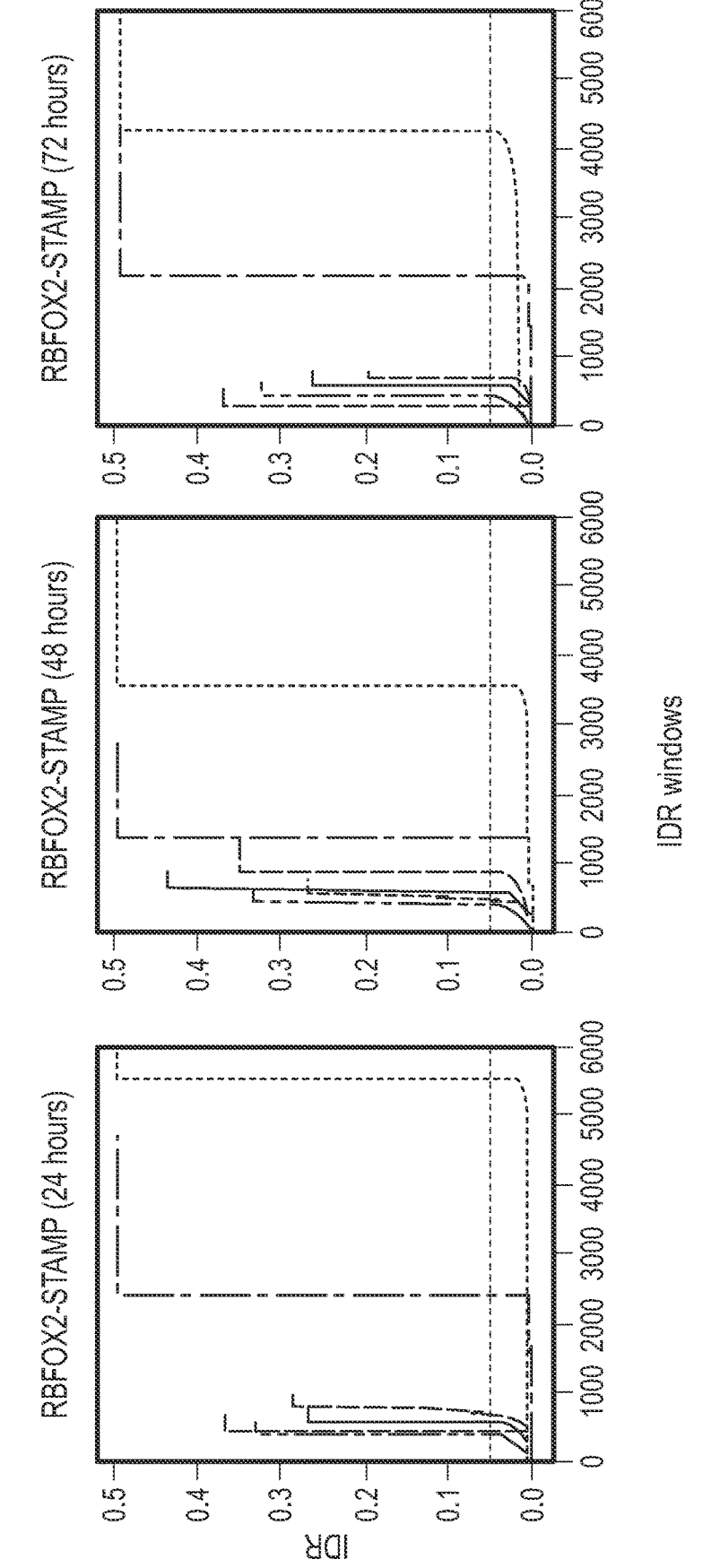
FIG. 4 shows irreproducible discovery rate (IDR) analysis comparing ≥0.5 confidence edit windows for increasing levels of RBFOX2-STAMP at 24, 48 and 72 hours. Results show that IDR analysis revealed reproducible windows with edits for RBFOX2-STAMP.
Figure 5:
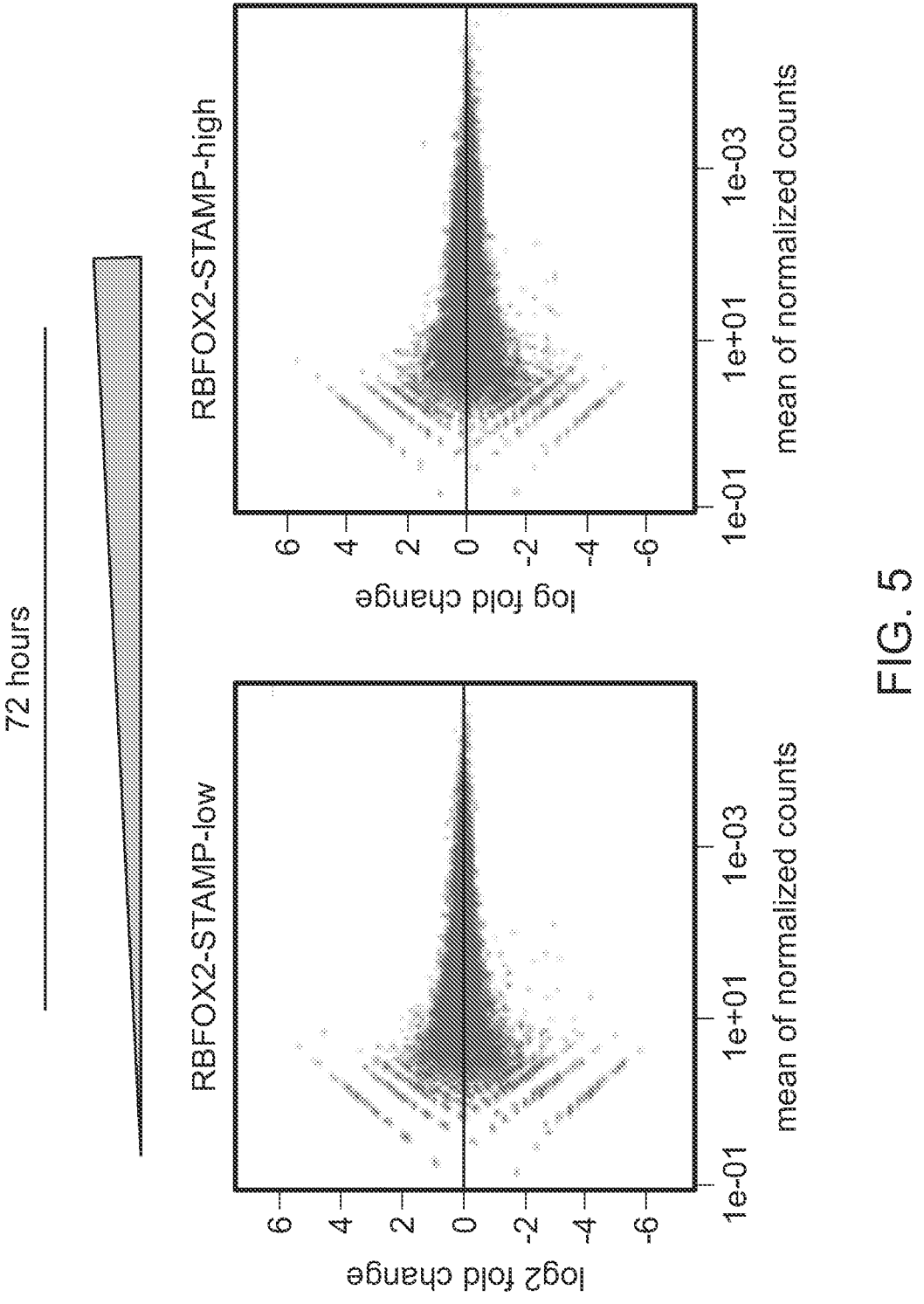
FIG. 5 shows differential expression (DEseq2) analysis of RBFOX2-STAMP for increasing levels of RBFOX2-STAMP at 72 hours where results show negligible changes in cellular gene expression compared to uninduced controls.
Figures 6A, 6B:
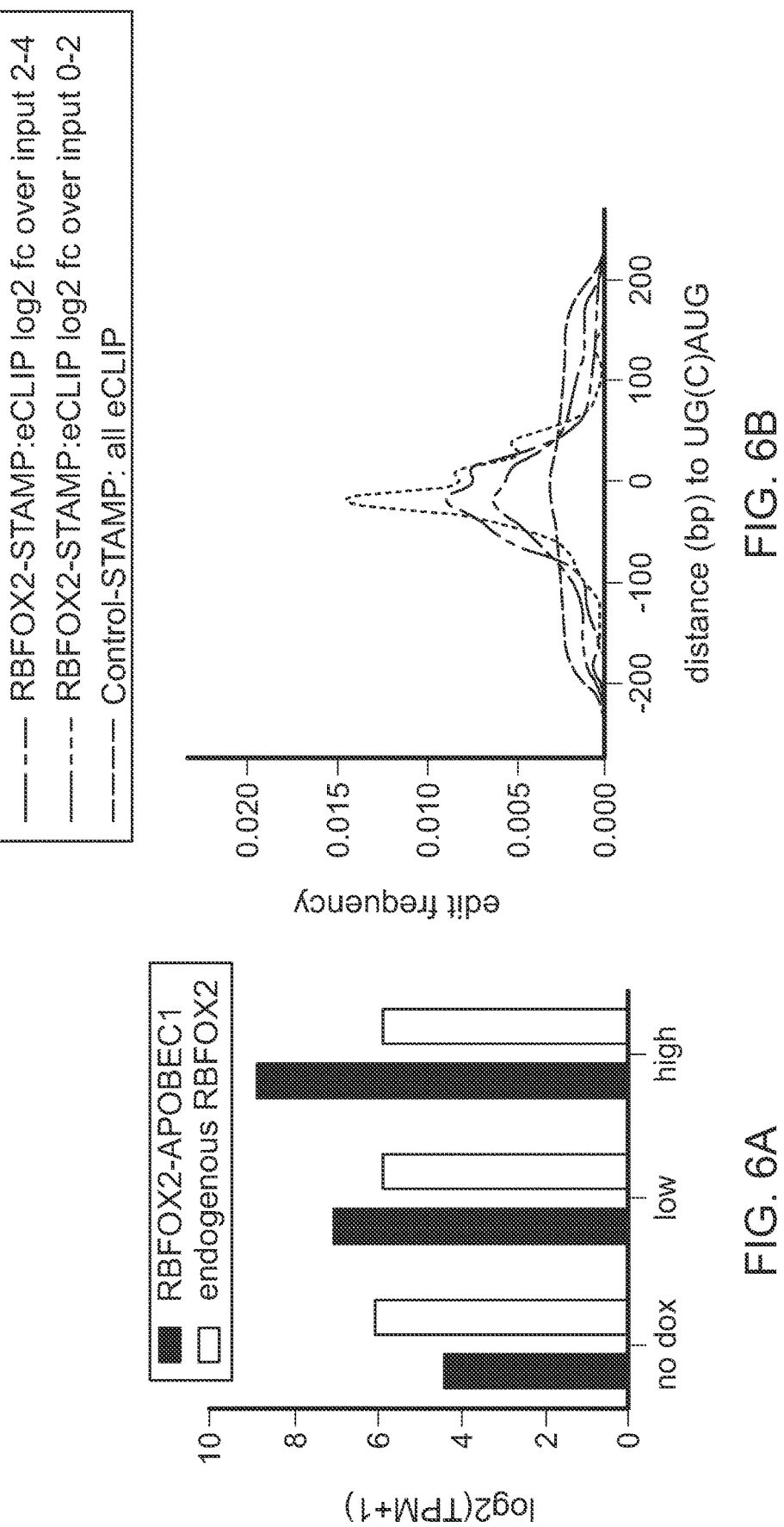
FIG. 6A shows quantification of expression from no dox (0 ng/ml), low (50 ng/ml) or high (1 µg/ml) doxycycline induction of RBFOX2-APOBEC1 fusion compared to endogenous RBFOX2 expression.
FIG. 6B is a graph showing RBFOX2-STAMP and control-STAMP (background) edit frequency distribution within a 400 bp window flanking RBFOX2 eCLIP binding-site motifs, split into increasing levels of log2 fold enrichment of eCLIP peak read-density over size-matched input. Results indicate that RBFOX2 RNA-binding activity is directing and enriching RBFOX2-STAMP specific edits at conserved sites.

To evaluate the reproducibility of STAMP, replicate control- and RBFOX2-STAMP was conducted with low and high doxycycline inductions for 24, 48, and 72 hours. The number of edited reads (E) on each target gene, normalized to read depth and gene length (PKM), were highly reproducible and correlations between replicates improved substantially upon induction ($R2=0.32$ at no dox treatment, to $R2=0.72$ and 0.83 at low and high dox, respectively; FIG. 3). Irreproducible discovery rate (IDR) analysis also revealed reproducible windows with edits for RBFOX2-STAMP, and the number of these reproducible edits also increased with dox induction of RBFOX2-STAMP (FIG. 4). The effects of RBFOX2-STAMP editing on target transcript levels was evaluated by conducting differential gene expression analysis on low and high-induction RBFOX2-STAMP at 24, 48, and 72 hours. Only negligible changes were detected in cellular gene expression compared to uninduced controls (FIG. 5 features the results for the 72 hour timepoint, which is similar to the 24 hour and 48 hour results). Expected basal leakiness of the doxycycline system was observed but with induction, RBFOX2-APOBEC1 mRNA levels increased to within 1.5-fold of the endogenous RBFOX2 levels (FIG. 6A).

To assess if RBFOX2-STAMP edits are enriched proximal to RBFOX2 motifs, the nucleotide distance of RBFOX2-STAMP edits from known RBFOX2 binding sites was measured. For 2,852 RBFOX2 eCLIP peaks that harbor the canonical RBFOX2 motif UGCAUG, distances from the motif to RBFOX2-STAMP and control-STAMP (background) edits were determined within a 400 bp window (FIG. 6B). Enriched edits for RBFOX2-STAMP within 200 bp of binding site motifs inside eCLIP peaks were observed, compared to edits from control-STAMP, and the proximity of edits to motifs correlated with eCLIP peak fold enrichment over size-matched input control, indicating that RBFOX2 RNA-binding activity is directing and enriching RBFOX2-STAMP specific edits at conserved sites.

Figures 7A, 7B, 7C:
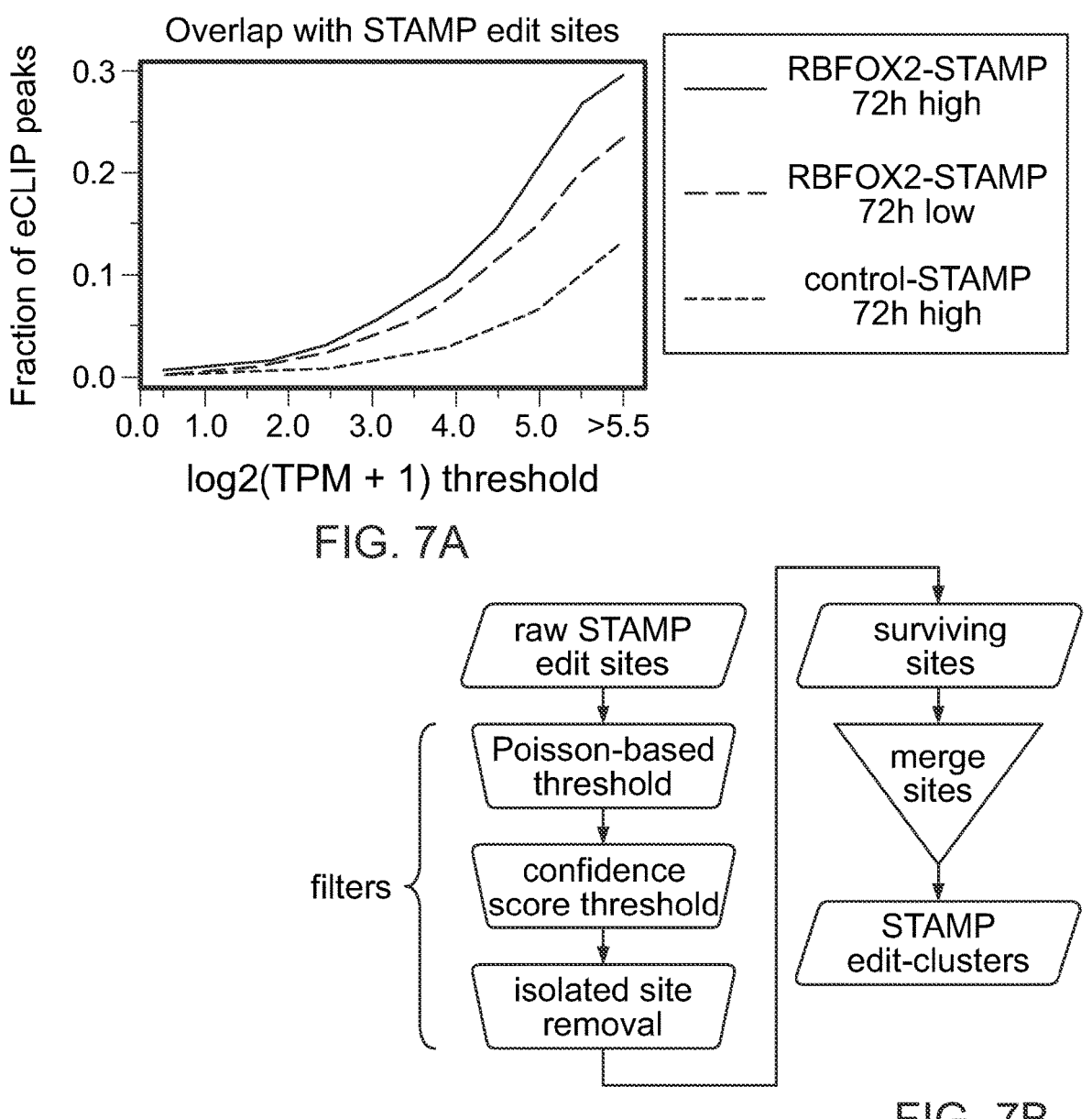
FIG. 7A is a graph showing fraction of RBFOX2-APOBEC1 eCLIP peaks overlapping low and high induction RBFOX2-STAMP edit sites at increasing expression (TPM) thresholds.
FIG. 7B is an exemplary schematic of a STAMP edit-site filtering and cluster-calling workflow showing an edit cluster-finding algorithm with gene-specific thresholds that assume Poisson-distributed edit-scores ε calculated for each site.
FIG. 7C is a table showing the number of control- and RBFOX2-STAMP edit sites and clusters retained after each filtering step in FIG. 7B.
Figures 8A, 8B:
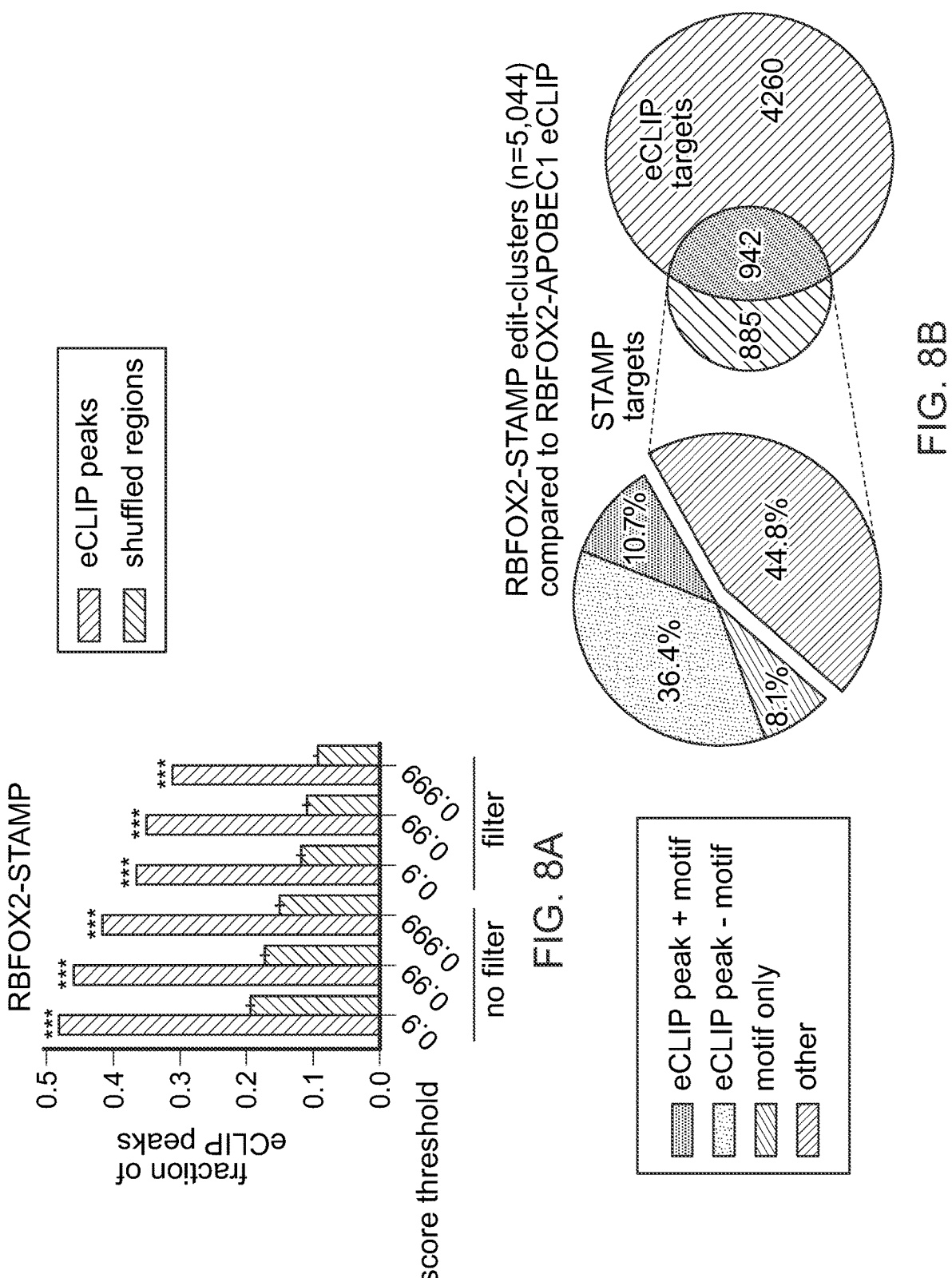
FIG. 8A is a bar graph showing fraction of RBFOX2-APOBEC1 eCLIP peaks (log2fc>2 and −log10p>3 over size-matched input) with RBFOX2-STAMP edit clusters, compared to size-matched shuffled regions, calculated at different edit site confidence levels before and after site filtering. Numbers atop bars are Z-scores computed comparing observed with the distribution from random shuffles.
FIG. 8B is a pie chart showing the proportion of filtered RBFOX2-STAMP edit clusters overlapping either 1) RBFOX2-APOBEC1 fusion high-confidence eCLIP peaks (log2fc>2 and −log10p>3) containing the conserved RBFOX2 binding motif, 2) equally stringent eCLIP peaks not containing the conserved motif, 3) the conserved motif falling outside of eCLIP peaks, or 4) neither eCLIP peaks or conserved motifs.
Figures 9A, 9B:
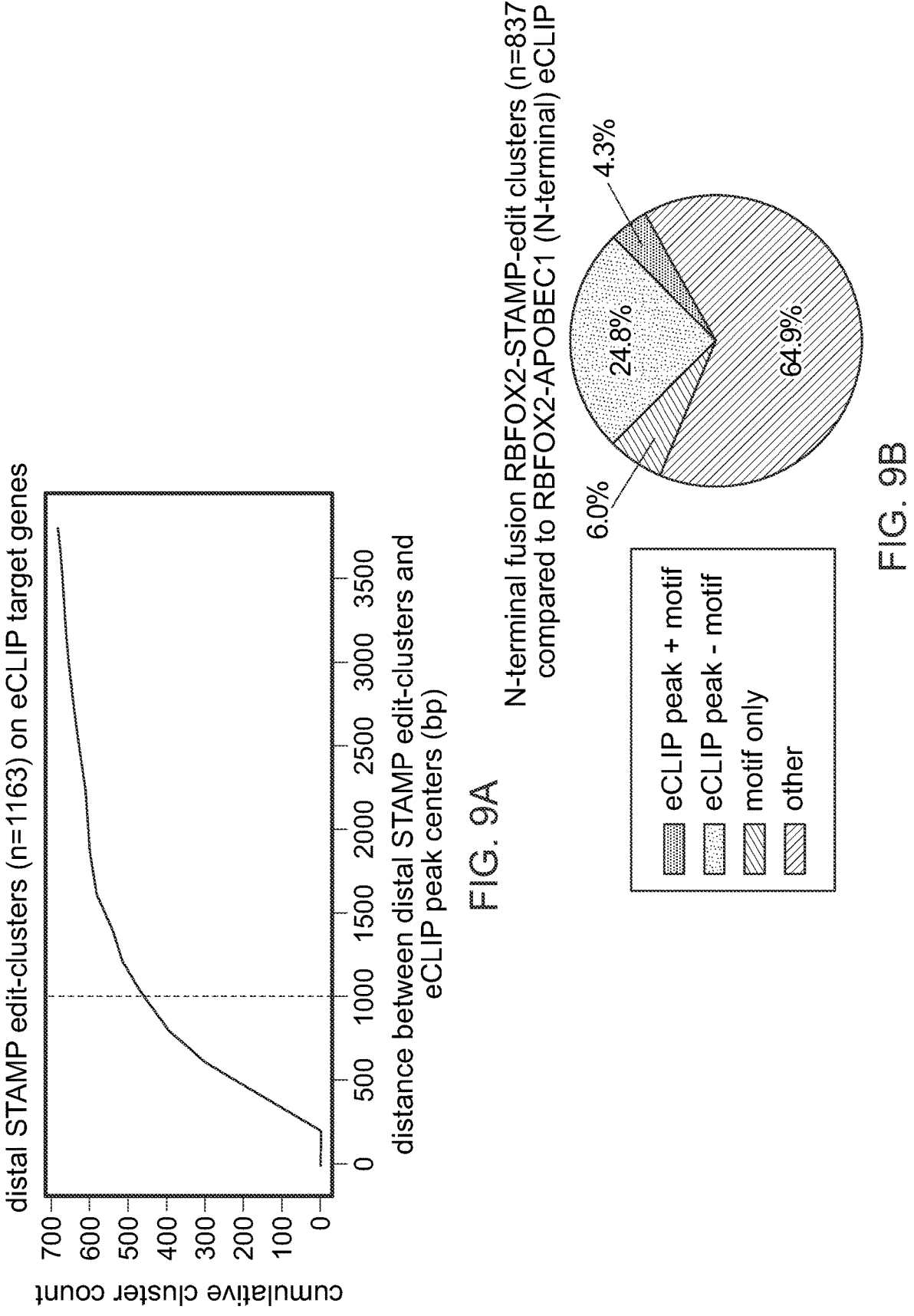
FIG. 9A is a graph showing cumulative distance measurement from RBFOX2-STAMP distal edit-clusters to eCLIP peaks on targets genes where results indicate that most clusters that did not overlap with eCLIP peaks were located within eCLIP target genes at a distance from neighboring eCLIP peaks.
FIG. 9B is a pie chart showing the proportion of N-terminally fused RBFOX2-APOBEC1 STAMP edit clusters overlapping with either 1) RBFOX2-APOBEC1 N-terminal fusion high-confidence eCLIP peaks (I2fc>2 and 110p>3 over input) containing the conserved RBFOX2 binding motif (GCAUG), 2) equally stringent eCLIP peaks not containing the conserved motif, 3) the conserved motif falling outside of eCLIP peaks, or 4) neither eCLIP peaks nor conserved motifs. Results show that the overlap was 20% smaller than what was observed for the C-terminal fusion, demonstrating that fusion orientation should be considered for each RBP of interest to maximize binding site capture.

Next, a set of criteria was developed that retrieves high-confidence edit-clusters for RBP-STAMP while reducing false positives, analogous to peak-calling in analyzing CLIP-seq datasets. It was observed that the frequency by which STAMP-mediated C-to-U edits overlap with RBFOX2-APOBEC1 eCLIP peaks increases with increasing gene expression thresholds that needed to be satisfied for the target genes (FIG. 7A). As expected, the read coverage of actual sites increases with the expression level of the target genes. However, more background edits within more highly expressed substrates can also be expected. To minimize this background while enriching for true binding sites, an edit cluster-finding algorithm was developed with gene-specific thresholds that assume Poisson-distributed edit-scores c calculated for each site. Sites that satisfied gene-specific c thresholds ($p<0.05$ with adjusted Bonferroni correction for multiple-hypothesis testing) and SAILOR confidence score thresholds were then merged with neighboring sites. Instances of edit sites with no neighboring edits within 100 bases in either direction were removed (workflow schematized in FIG. 7B). Similar to CLIP-peak callers, the workflow is tailored for RBPs which bind in a relatively specific manner (a few to several regions within a gene) and in practice, filter parameters can be user-defined for different RBPs that account for different modes of binding (such as broad-binding RBPs). These criteria established a set of 5044 edit-clusters for RBFOX2-STAMP (5.4% of the original unfiltered windows) and removed essentially all background control-STAMP sites (21 remaining, 0.04% of unfiltered windows) (FIG. 7C). Next, the fraction of RBFOX2-APOBEC1 e CLIP peaks detected by these RBFOX2-STAMP edit-clusters were determined. It was found that nearly half of all significant eCLIP peaks (>4-fold enriched over size-matched input and $P<0.001$) overlapped with RBFOX2 edit-clusters at a SAILOR confidence threshold of 0.9 for the edit sites, more than 2-fold higher compared to overlaps with size-matched randomly shuffled regions on exons of the same target genes (FIG. 8A). This may be a conservative estimate as the same RBFOX2 target gene often contains another region bound by the RBP, but this stringent comparison retains the expression profile of the target substrates. At higher SAILOR confidence thresholds, the fraction that overlaps decreases but the enrichment over background is preserved. It was observed that 47% of RBFOX2-STAMP edit-clusters overlapped with RBFOX2 eCLIP peaks, irrespective of whether the eCLIP peaks contained known RBFOX2 binding motifs and an additional 8% of the edit clusters contained the RBFOX2 motif (FIG. 8B). Interestingly, most clusters that did not overlap with eCLIP peaks were nevertheless located within eCLIP target genes at a distance from neighboring eCLIP peaks (FIG. 9A). While 14.4% of all 51,020 unfiltered control clusters overlapped with RBFOX2 eCLIP peaks and motifs, subjecting control-STAMP sites to the same criteria for RBFOX2-STAMP sites left essentially no background edit clusters to compare to eCLIP (FIG. 7C). The orientation of the APOBEC1 fusion protein was also evaluated and it was observed that edit-clusters obtained from N-terminally fused RBFOX2-STAMP also maintained overlap with eCLIP peaks from a separate N-terminal fusion of APOBEC1 to RBFOX2. However the overlap was 20% smaller than what was observed for the C-terminal fusion, demonstrating that fusion orientation should be considered for each RBP of interest to maximize binding site capture (FIG. 9B).

Figure 10A:
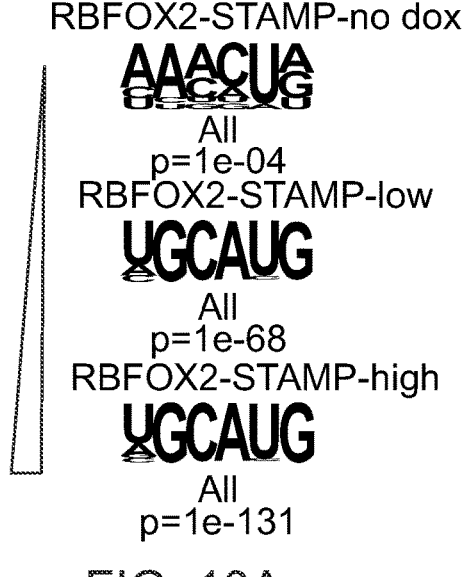
FIG. 10A shows motif enrichment using HOMER and shuffled background on RBFOX2-STAMP edit-clusters for increasing RBFOX2-STAMP induction levels. Results show the sensitivity and specificity of STAMP for discovering RBP binding sites.

Lastly, de novo motif discovery was performed using high-confidence RBFOX2-STAMP edit clusters, assessing enrichment above a shuffled background for each gene region. These edit-clusters were statistically significantly enriched for the UGCAUG RBFOX2 binding motif, and the enrichments were correlated with the doxycycline dose and subsequent expression levels of RBFOX2-STAMP (FIG. 10A). No level of control-STAMP expression at any window size or confidence level derived the (U)GCAUG motif, demonstrating the sensitivity and specificity of STAMP for discovering RBP binding sites.

Figure 10B:
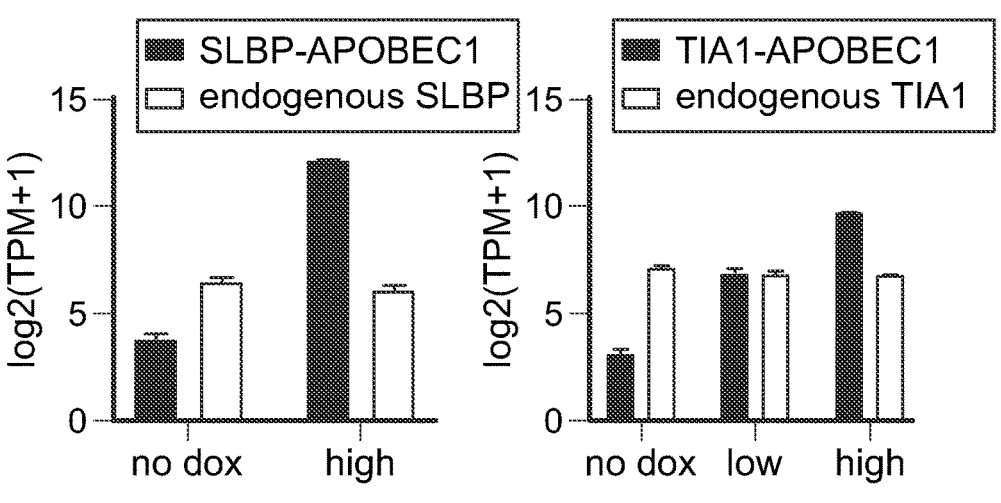
FIG. 10B is a set of bar graphs showing quantification of expression from no dox 836 (0 ng/ml) low (50 ng/ml) or high (1 µg/ml) doxycycline induction of SLBP-APOBEC1 and TIA1-APOBEC1 fusions compared to endogenous expression. Results show similar STAMP-fusion expression levels compared to endogenous TIA1 and SLBP.
Figure 10C:
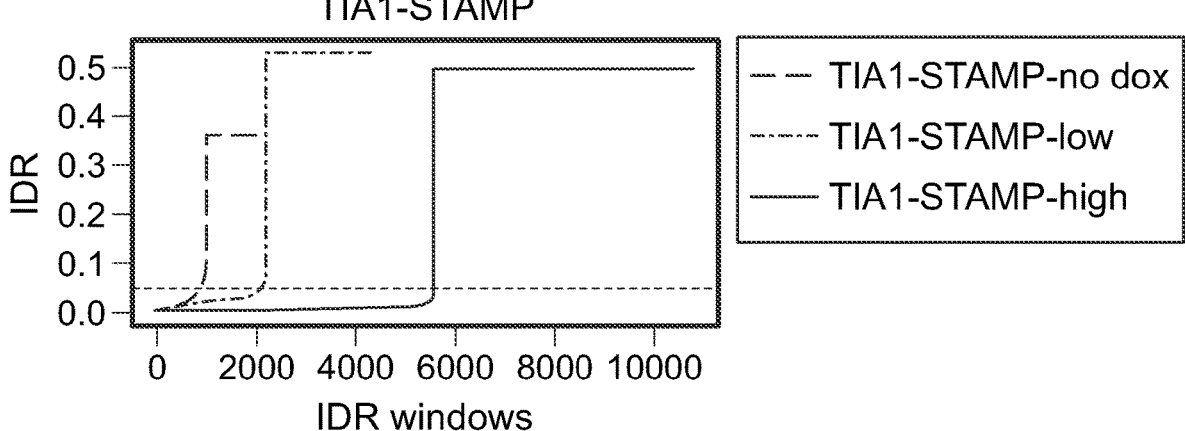
FIG. 10C is a graph showing irreproducible discovery rate (IDR) analysis comparing 0.5≥confidence level edit windows for increasing levels of TIA1-STAMP at 72 hours.
Figures 11A, 11B:
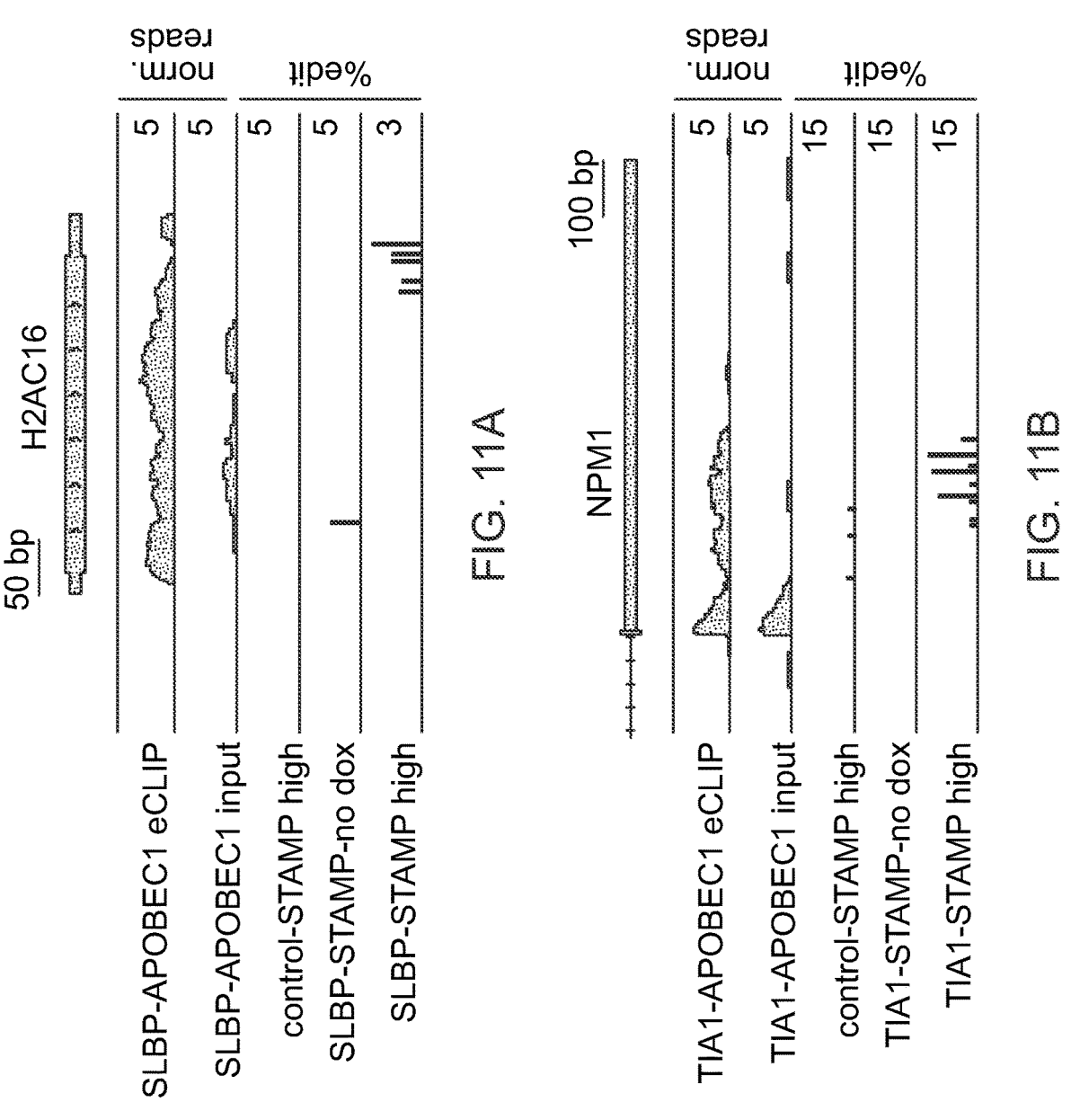
FIG. 11A shows IGV tracks showing control- and SLBP-STAMP edit fractions at no- and high-induction (doxycycline: 0 ng=none or 1 µg/ml=high, 72 hours) on the target histone gene H2AC16 compared to SLBP-APOBEC1 eCLIP.
FIG. 11B shows IGV tracks showing control- and TIA1-STAMP edit fractions at no- and high-induction (doxycycline: 0 ng=none or 1 µg/ml=high, 72 hours) on the target gene NPM1 compared to TIA1-APOBEC1 eCLIP.
Figures 12A, 12B, 12C:
FIG. 12A is a bar graph showing fraction of SLBP eCLIP peaks (log2fc>2 and −log10p>3 over size-matched input, reproducible by IDR) with SLBP-STAMP edit-clusters, compared to size-matched shuffled regions, calculated at different edit site confidence levels before and after site filtering. Results show greater than 70% of all significantly reproduced SCBP eCLIP peaks overlapped with SLBP-STAMP edit clusters.
FIG. 12B is a bar graph showing fraction of TIA1-APOBEC1 eCLIP peaks (log2fc>2 and −log10p>3 over size-matched input) with TIA1-STAMP edit-clusters, compared to size-matched shuffled regions, calculated at different edit site confidence levels before and after site filtering. Results show more than 30% of all significant TIA1-APOBEC1 eCLIP peaks overlapped with TIA1-STAMP edit clusters.
FIG. 12C shows motif enrichment using HOMER and shuffled background on TIA1-STAMP edit-clusters. Results demonstrate the versatility of the STAMP approach in specifically and reproducibly detecting the targets and binding sites of multiple RBPs.

Next, two additional HEK293T RBP-STAMP cell lines were generated, one that inducibly expresses APOBEC1 fused to the histone stem-loop binding protein SLBP, and another that expresses a fusion to the stress granule protein TIA1 that binds target mRNA 3'UTRs. SLBP has a very specific set of characterized RNA targets, binding histone mRNAs at 20 nucleotide stem loop regions near the very 3' end of 3'UTRs preceding non-polyadenylated cleavage sites. Similar STAMP-fusion expression levels were noted compared to endogenous TIA1 and SLBP, as they were observed for RBFOX2-STAMP (FIG. 10B). As with RBFOX2-STAMP, the number of TIA1-STAMP edits on target genes increased with doxycycline concentration and were strongly correlated across replicates, with summary IDR analysis revealing thousands of reproducible edits that increased in number with increasing induction levels (FIG. 10C). Comparison of SLBP-STAMP to SLBP-APOBEC1 eCLIP data showed that SLBP-STAMP edits were enriched compared to control-STAMP near eCLIP peaks within the 3'UTR of histone genes, such as H2AC16 (FIG. 11A) adjacent to stem loop regions, as expected. Much like RBFOX2- and SLBP-STAMP, comparison of control- and TIA1-STAMP to TIA1-APOBEC1 eCLIP revealed that there was inducible TIA1-STAMP edit enrichment overlapping the example eCLIP 3'UTR peak within the NPM1 gene (FIG. 11B). It was found that greater than 70% of all significantly reproduced SLBP eCLIP peaks (>4-fold enriched over size-matched input and P<0.001, reproducible by IDR) overlapped with SLBP-STAMP edit-clusters (FIG. 12A), and more than 30% of all significant TIA1-APOBEC1 eCLIP peaks (>4-fold enriched over size-matched input and P<0.001) overlapped with TIA1-STAMP edit clusters (FIG. 12B), with size-matched randomly shuffled regions on exons of the respective genes showing significantly lower concordance with edit-clusters at any threshold for both SLBP- and TIA1-STAMP. De novo motif analysis also showed the known eCLIP established U(A)-rich binding sequence from TIA1-STAMP edit-clusters (FIG. 12C). These results confirm the versatility of the STAMP approach in specifically and reproducibly detecting the targets and binding sites of multiple RBPs.

Figures 13A, 13B:
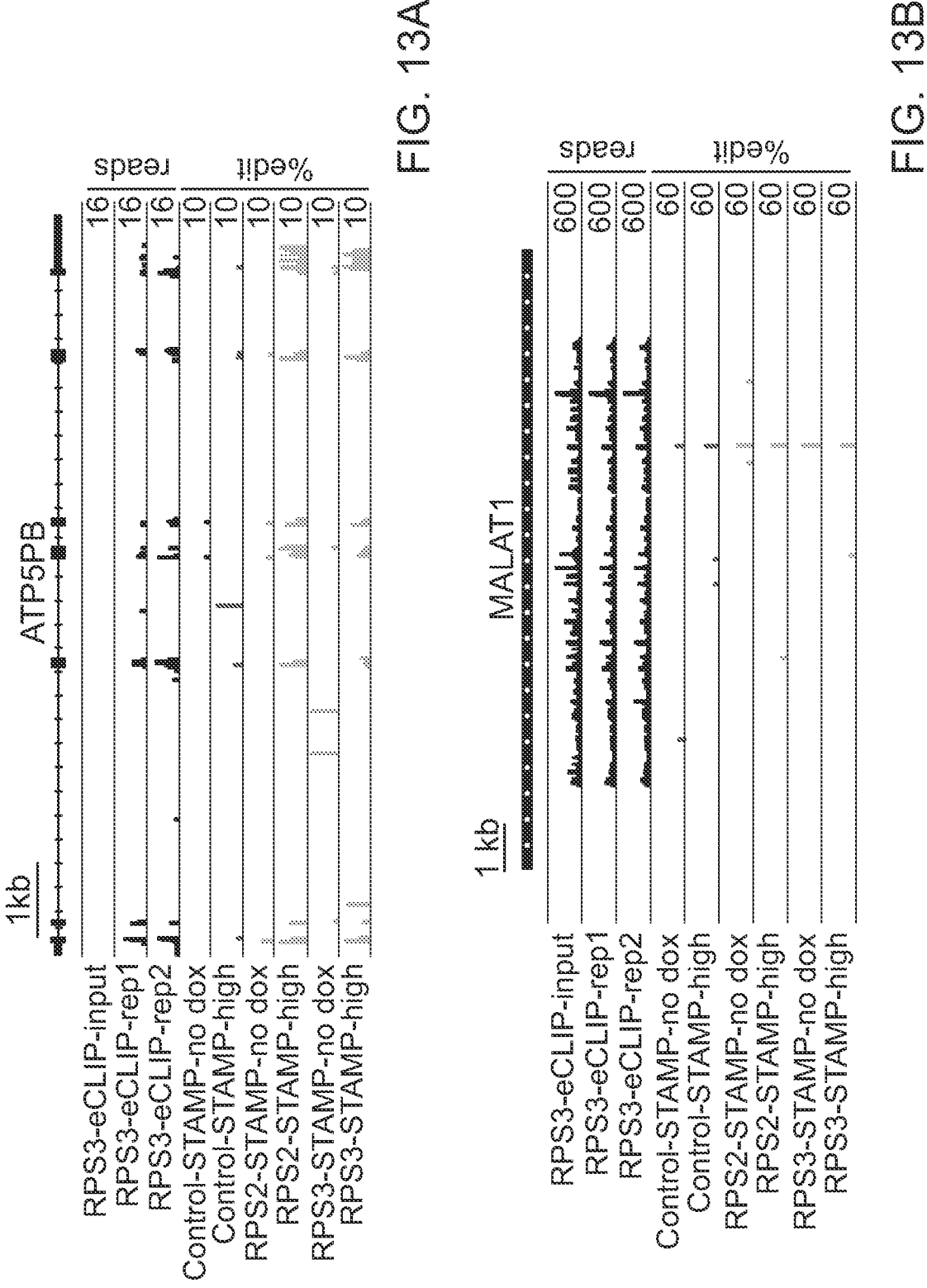
FIG. 13A shows IGV browser tracks displaying coding sequence edit frequency from control, RPS2-STAMP, and RPS3-STAMP at no induction or 72-hour high-induction on the ATP5BP gene locus. RPS3 eCLIP and input reads are shown for comparison. Results show that C-to-U edits were enriched relative to control-STAMP on exons of protein-coding genes that are highly translated in HEK293T cells, such as ATP5PB.
FIG. 13B shows IGV browser tracks as in FIG. 13A on the noncoding RNA MALAT1, showing no enrichment for RPS3 eCLIP reads, RPS2- or RPS3-STAMP edits.
Figures 14C, 14D, 14E:
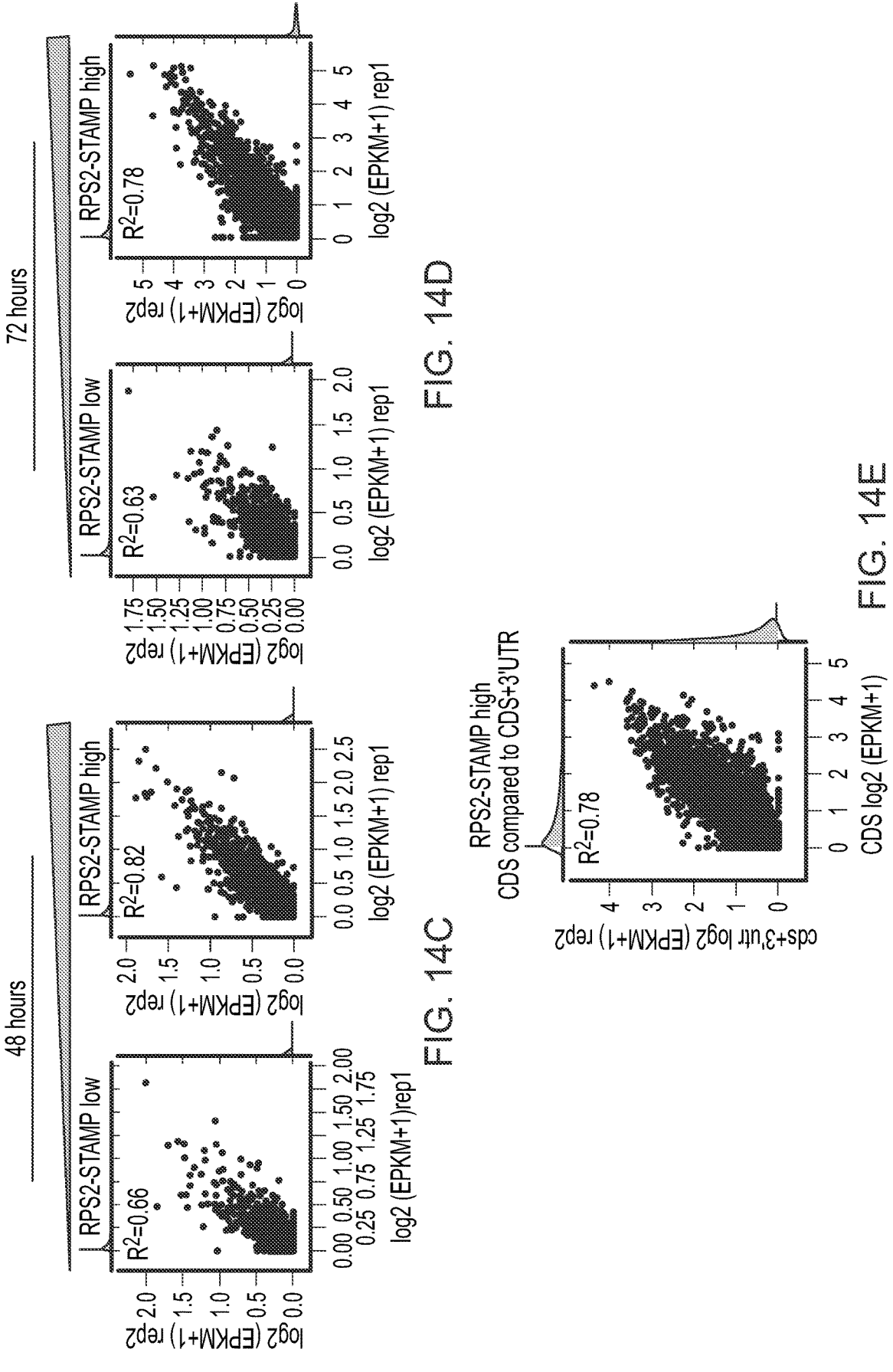

Example 2—Ribosome-Subunit STAMP
(Ribo-STAMP) Edits are Enriched in Highly
Translated Coding Sequences and Responsive to
mTOR Inhibition Since ribosomes have extensive association with mRNAs during translation, ribosomal subunits fused to APOBEC1 (Ribo-STAMP) may have the potential to edit mRNAs in a manner that reflects ribosome association. It was previously observed that eCLIP of the small ribosomal subunit RPS3 featured binding patterns that recapitulated the average profile captured by ribosome profiling. Independent HEK293T cell lines expressing APOBEC1 fusions to ribosomal subunits RPS2 and RPS3 were generated. For RPS2-STAMP and RPS3-STAMP, C-to-U edits were enriched relative to control-STAMP on exons of protein-coding genes that are highly translated in HEK293T cells, such as ATP5PB, coincident with RPS3 eCLIP signal enrichment over size-matched input control (FIG. 13A). In comparison, RPS2-STAMP and RPS3-STAMP signal were minimally detected on highly expressed non-coding genes such as the lncRNA MALAT1, which is localized to the cytoplasm in mitotic cell lines (FIG. 13B). Replicate RPS2-STAMP and control-STAMP inductions were performed at low and high doxycycline concentrations for 24, 48, and 72 hours and again observed dose-dependent STAMP-fusion expression compared to endogenous RPS2 levels (FIG. 14A) with strong EPKM reproducibility between replicates (R2=0.6 to 0.8) as well as low overlap (2.8% of all detectable edits) between control-STAMP and RPS2-STAMP edit sites at high induction (FIGS. 14B-14D). As edits from RPS2- and RPS3-STAMP were present in coding sequences (CDS) and also in 3'UTR sequences (FIG. 13A), it was determined whether these 3'UTR edits should be filtered or if they are coincident bystander edits to coding region edits. Comparison of EPKM computed from CDS only, to EPKM values computed from both CDS and 3'UTR revealed a strong correlation, indicating that 3'UTR edits need not be excluded from downstream analyses and in some instances may provide edits otherwise missed if only CDS regions in genes with short open-reading frames were considered (R2=0.78, FIG. 14E).

Figures 15A, 15B, 15C:
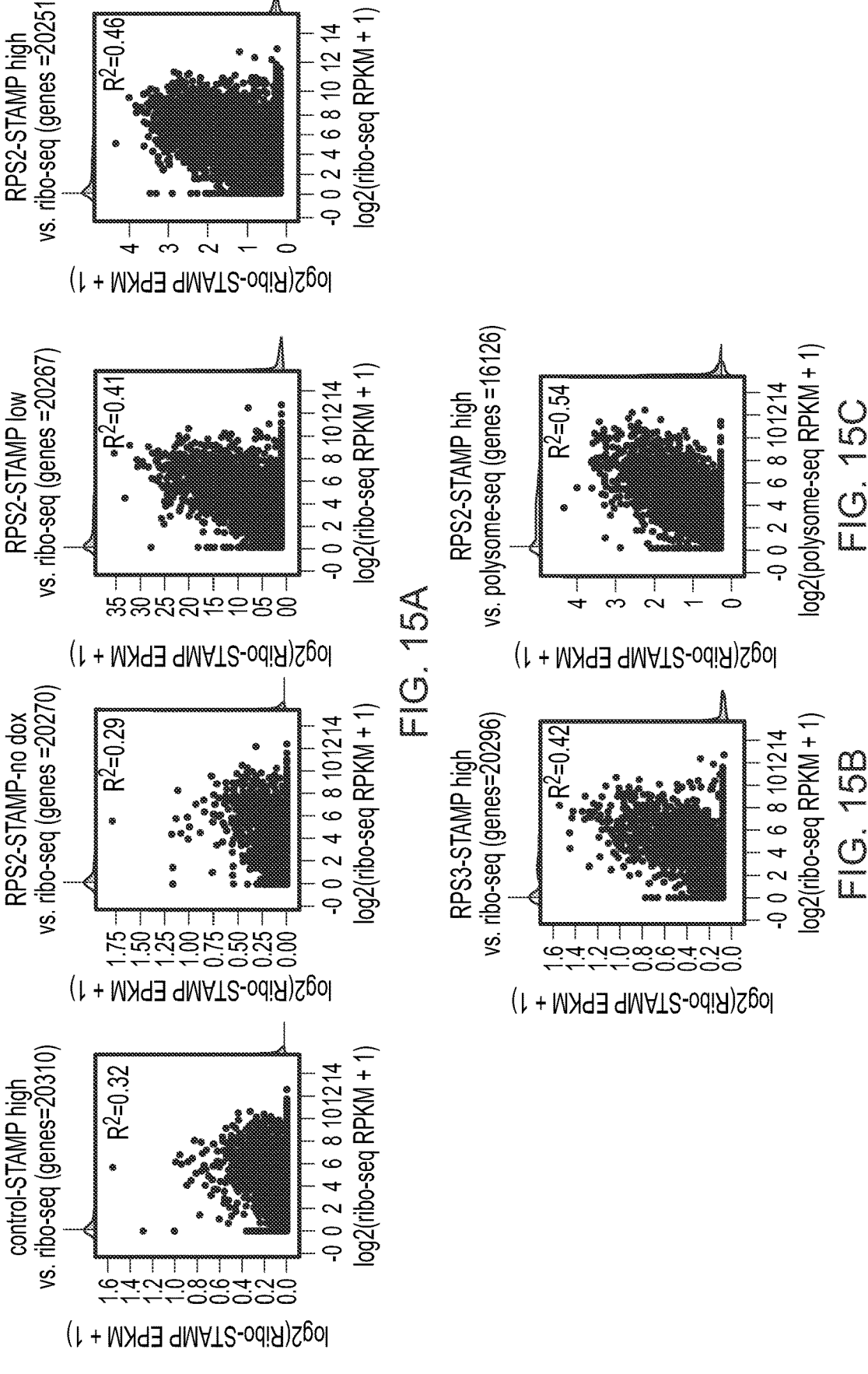
FIG. 15A shows genome-wide scatterplot comparison of control- and RPS2-STAMP EPKM and ribo-seq ribosome protected fragment (RPF) RPKM for increasing levels of RPS2-STAMP. Results show that at low and high levels of doxycyline induction, the correlations between EPKM values for RPS2-STAMP and ribo-seq RPF RPKM values improved significantly.
FIG. 15B shows comparison as in FIG. 15A with ribo-seq RPF RPKM and EPKM from RPS3-STAMP.
FIG. 15C shows comparison as in FIG. 15A with polysome-seq RPKM and EPKM from RPS2-STAMP.
Figure 16:
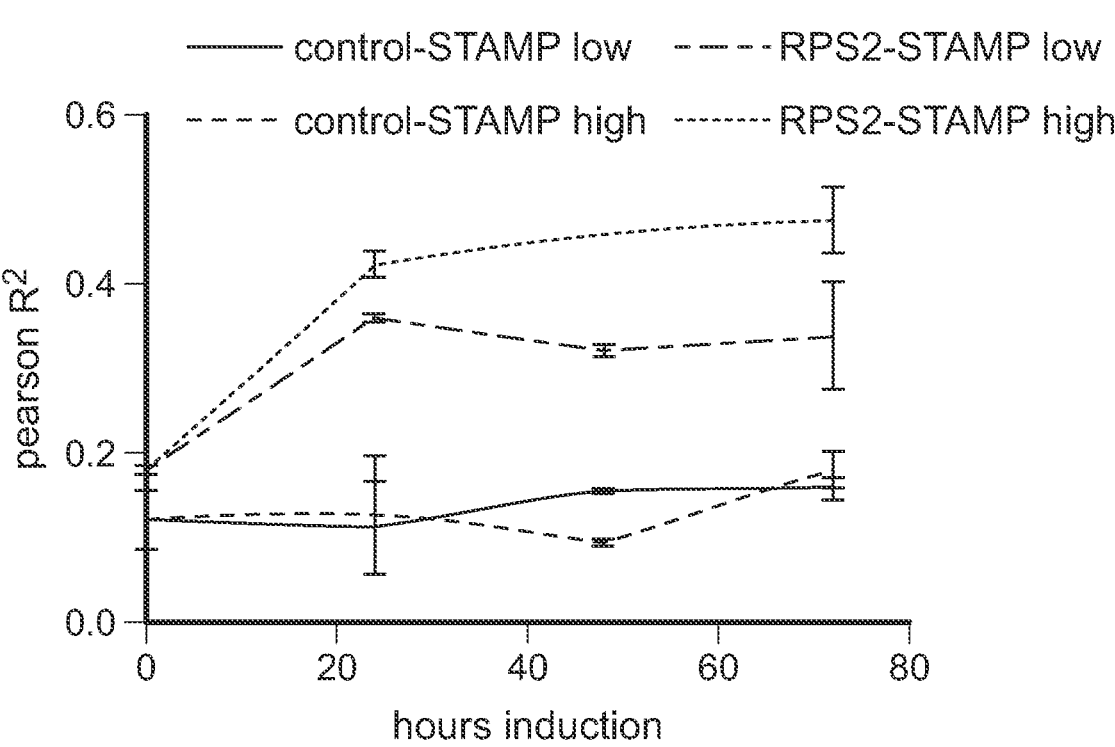
FIG. 16 is a graph showing pearson $R^2$ values for low and high induction control or RPS2-STAMP EPKM compared to poly-ribosome-enriched polysome-seq RPKM. Results demonstrate that Ribo-STAMP edit read counts can track ribosome occupancy measurements from multiple ribosome profiling approaches.

To evaluate whether Ribo-STAMP can distinguish genes with varying levels of ribosome occupancy combined genome-wide EPKM values from control-, RPS2- and RPS3-STAMP were compared to RPKM values from ribosome protected fragments (RPF) obtained from standard ribosome profiling (ribo-seq) and to RPKM values from poly-ribosome-fraction-enriched RNA (polysome seq) experiments performed in HEK293 cells. For control-STAMP and for uninduced RPS2-STAMP, EPKM values were poorly correlated with ribo-seq RPKM values (R2=0.32 and R2=0.29 respectively, FIG. 15A, left). At low and high levels of doxycyline induction, the correlations between EPKM values for RPS2-STAMP and ribo-seq RPF RPKM values improved significantly (R2=0.41 and R2=0.46 respectively FIG. 15A). A similar relationship was observed when comparing RPS3-STAMP to ribo-seq (R2=0.42 FIG. 15B). RPS2-STAMP and polysome-seq measurements were also well correlated (R2=0.54), consistent across replicates and improved at higher doxycycline induction concentrations and expression times (FIG. 15C, FIG. 16). As RPS2-STAMP had higher correlation with independent ribosome foot-printing approaches than RPS3-STAMP (FIG. 15B), RPS2-STAMP as the representative Ribo-STAMP fusion for downstream analysis was performed. Meta-coding gene analysis of RPS2-STAMP edits for the top quartile of ribosome-occupied (ribo-seq) genes revealed enrichment of edits within the CDS when compared to control-STAMP background edits and RBFOX2-STAMP edits, which showed the expected 3'UTR profile consistent with eCLIP (FIG. 17A). Enrichment of RPS2-STAMP edits within 3'UTRs likely indicates small ribosomal subunit association with these accessible regions following ribosome translation termination by release factors, as 3'UTR signal from endogenous RPS3 eCLIP was also observed (FIG. 13A). These results are in agreement with previous studies revealing widespread 3'UTR ribosome footprints in both yeast and human cells. Together these results demonstrate that, on a gene-by-gene basis, Ribo-STAMP edit read counts track ribosome occupancy measurements from multiple gold-standard ribosome profiling approaches.

To determine if Ribo-STAMP edits detect translational perturbations, stable high induction RPS2- and control-STAMP was performed and cells with the mammalian target of rapamycin (mTOR) pathway inhibitor Torin-1, a selective ATP-competitive inhibitor of mTOR kinase were simultaneously treated. Pharmacological inhibition of the mTOR pathway globally suppresses translation of mRNAs after initially suppressing translation of genes encoding the translational machinery itself 72-hour Torin-1 treatment resulted in reproducible suppression in RPS2-STAMP edit distributions compared to vehicle treated cells, exemplified by a marked decrease in edits on the top quartile of ribosome occupied genes (ribo-seq, FIG. 17B). RPS2-STAMP EPKM values were also significantly reduced upon Torin-1 treatment in the highest quartile of ribosome occupied genes as defined by ribo-seq (Q1 p=1.5 e-144, Wilcoxon rank-sum test), and polysome-seq (Q1 p=5.5 e-108, Wilcoxon rank-sum test), and all previously reported Torin-1 sensitive TOP genes were contained within these top quartiles (FIG. 18A). No significant reduction in EPKM values was observed for control-STAMP cells upon Torin-1 treatment for any matched comparisons (FIG. 18B). Together these results demonstrate that specific and dynamic translational responses are detected by Ribo-STAMP.

Example 3—Long-Read STAMP Reveals
Isoform-Specific Binding Profiles

Given that STAMP does not require isolation of RBP-protected RNA fragments, unlike CLIP assays, STAMP may enable RNA target detection on full-length mRNA isoforms using long-read sequencing technology. A 72-hour stable high-induction RBFOX2- and control-STAMP was performed and cDNA long reads were directly sequenced with the Oxford Nanopore Technologies (ONT) and PacBio (PB) sequencing platforms. Both long-read sequencing approaches resulted in enrichment above control of C-to-U edits from RBFOX2-STAMP that overlapped with both eCLIP signal and short read (Illumina) RBFOX2-STAMP signal, as illustrated by the target gene APP 3'UTR (FIG. 19A). Long-read high confidence (≥0.99) RBFOX2-STAMP edits enriched the known RBFOX2 UGCAUG binding motif for both approaches (FIG. 19B). As has been previously reported, PacBio sequencing has a lower base-calling error rate than Nanopore sequencing, leading to very clear separation between control-STAMP and RBFOX2-STAMP edits and more significant motif extraction. Long read data from PacBio sequencing was used for downstream isoform-specific editing analysis.

RBFOX2 3'UTR binding functionality is largely uncharacterized, but it is conceivable that RBFOX2 3'UTR binding can contribute to, or result from, alternative polyadenylation (APA) of certain targets, and RBFOX2 has been shown to bind alternative 3'UTR isoforms to influence stability or translation. To evaluate isoform-specific binding events, RBFOX2-STAMP or control-STAMP edit read fractions were calculated on the primary and secondary alternative polyadenylation APA isoforms of all genes (RBFOX2-STAMP n=1604, control-STAMP n=1878) that satisfied a minimal coverage threshold of 10 reads per isoform for long reads obtained from PacBio sequencing. Differential isoform editing signatures for RBFOX2-STAMP were observed compared to control-STAMP (FIG. 20A). To illustrate, edits on the FAR1 (FIGS. 20B-20C) as well as PIGN (FIGS. 20C-20D) genes were displayed and RBFOX2-STAMP (but not control-STAMP) APA isoform-specific edits were observed to be enriched on shared 3'UTR regions for different length 3'UTR isoforms, suggesting isoform-specific binding by RBFOX2 to these transcripts. These isoform specific binding sites coincided with both short-read RBFOX2-STAMP edit clusters and RBFOX2-APOBEC1 eCLIP peaks, however the alternate isoforms were not discernable using these short-read approaches. These results demonstrate that STAMP enables isoform-aware long read detection of RBP-RNA interactions.

Example 4—Detection of RBFOX2-RNA Targets at Single-Cell Resolution

To evaluate whether STAMP can discover RBP-RNA interactions in single cells, a commercially available single-cell capture platform was used. Plasmid vectors were modified to enable capture by the 10× Genomics Single Cell 3' v3 beads and performed 72-hour stable high-induction RBFOX2- and control-STAMP in distinct HEK293T cell-lines followed by standard single-cell (sc) RNA-seq. Using the inserted capture-sequence adjacent to the RBP open-reading frames, RBFOX2-STAMP cells and 5,242 control-STAMP cells were identified.

Comparison of bulk and single-cell edit fractions for control- and RBFOX2-STAMP experiments across the top 200 expressed genes (ranked by transcripts per million from bulk RBFOX2-STAMP RNA-seq) revealed nearly identical edit enrichment profiles of RBFOX2 samples above controls and further uncovered a spectrum of editing frequencies across individual cells (FIG. 21A). To illustrate, individual control- and RBFOX2-STAMP cells by summed e score were ranked and edit fractions were visualized for the top 10 cells on the RBFOX2 eCLIP target gene UQCRH. For all 10 selected RBFOX2-STAMP cells, but not control-STAMP cells, consistent edit signal in close proximity to the RBFOX2 eCLIP peak that overlapped with edit enrichment from both bulk RBFOX2-STAMP and the aggregate of all RBFOX2-STAMP cells was observed (FIG. 21B), revealing that STAMP can define RBP binding sites at single-cell resolution. Very strong concordance (80%) was observed in the target genes that contained filtered high-confidence RBFOX2-STAMP edit clusters obtained from single-cell and bulk datasets (FIG. 21C). At the binding site level, 60% of these high-confidence single-cell edit-clusters directly overlapped edit-clusters obtained from bulk RBFOX2-STAMP, and −70% of all single cell edit-clusters fell within 400 bp of bulk edit-clusters (FIG. 22A). In addition, 73% of single-cell STAMP targets that contained edit-clusters also contained significant RBFOX2-APOBEC1 eCLIP peaks (P<0.001; FIG. 22B). As with bulk RBFOX2-STAMP, a majority of the single-cell RBFOX2-STAMP edit-clusters overlapped eCLIP peaks and harbored RBFOX2 binding motifs (FIG. 22C), with a large number of clusters that did not directly overlap eCLIP peaks still present in target genes generally within 1000 bp of the neighboring eCLIP peak (FIG. 22D). Single-cell RBFOX2-STAMP eCLIP peak capture rate was associated with target expression level (FIG. 23A). De novo motif analysis from edit-clusters by randomly down sampling the numbers of single cells analyzed identified the canonical (U)GCAUG motif with significance, even to the resolution of one cell (FIG. 23B) showcasing the strength of single-cell STAMP.

Example 5—Deconvolution of RBP- and Cell Type-Specific RNA Binding

The ability of STAMP to recover RBP-RNA targets in single cells suggests that targets of multiple RBPs can be simultaneously discovered from a single multiplexed experiment. In a RBFOX2-STAMP experiment, 72-hour high-induction TIA1-STAMP was performed, prior to mixing equal number of RBFOX2- and TIA1-STAMP cells, followed by scRNA-seq. Cells harboring capture sequences for TIA1-and RBFOX2-STAMP were better distinguished from each other and from control-STAMP cells by UMAP visualization using ε scores, than by gene expression (FIGS. 24A-24B and FIG. 25A), congruent with expectations that the single-cell ε score profiles of TIA1- and RBFOX2-STAMP targets were sufficiently distinct. UMAP visualization of ε scores further revealed that control-STAMP cells (n=8,117 cells) were distinct from RBFOX2- and TIA-STAMP "capture cells" (FIG. 24B). Using Louvain clustering by ε score profiles an RBFOX2-population (n=6,003 cells), a TIA1-population (n=1,841 cells) and a background-population (n=6,623 cells) was defined for further analysis (FIG. 25B). Overlap with control (FIG. 24C) and re-clustering in the expression space (FIG. 25C) for these defined clusters highlighted the utility of ε score-based clustering for defining RBP-specific cell groups. De novo motif analysis of edits from the aggregated cells in the RBFOX2-cluster, but not control, confirmed edit enrichment at RBP-specific binding sites (FIG. 26C), and TIA1-and RBFOX2-clusters displayed distinct editing profiles when compared to control-STAMP (FIG. 26A). Cells were ranked based on summed ε scores to select cells with the most robust editing and found that the top 5 cells for each RBP displayed edit enrichment on the shared RBFOX2- and TIA1-STAMP target NPMJ, which was also detected as a TIA1 target by eCLIP and bulk TIA1-STAMP (FIG. 11B). Individual cell edit enrichments were specific to TIA1-STAMP on the BTF3 target gene, and to RBFOX2-STAMP on the CFL1 target gene (FIG. 26B), demonstrating that the targets and binding sites of multiplexed RBP-STAMP fusions can be delineated from edit signatures within single-cell experiments.

Next, cell-type specific RBP targets were identified using single-cell STAMP. STAMP was performed in HEK293T cells and pluripotent stem cell-derived neural progenitor cells (NPCs) by transient transfection with plasmids constitutively expressing either RBFOX2- or control-STAMP fusions, and then mixed equal numbers of HEK293T and NPC cells for each STAMP construct before performing scRNA-seq. UMAP visualization revealed that cells clustered by gene expression into distinct HEK293T and NPC subgroups expressing cell-type specific markers (FIG. 27A, FIG. 28A). UMAP clustering on ε score also resulted in separation of cell types (as determined by gene expression clustering) based on RBFOX2-STAMP edits (FIG. 27B), and the RBFOX2 binding motif was extracted using edit clusters from 2,178 NPC cells editing 468 target genes, and 3,258 HEK293 cells editing 939 target genes (FIG. 28B). Analysis of the top RBFOX2-STAMP differentially edited genes between cell types revealed cell-type specific targets (FIG. 29A) that were often not differentially expressed (FIG. 29B), indicating cell-type specific RNA protein interactions independent of target expression levels. Individual cell edits for the top 5 control- or RBFOX2-STAMP cells from each cell-type ranked by summed ε score illustrated targets that were edited specifically in HEK293 cells such as RPL14 or in NPC cells such as RPL13A (FIG. 29C). Together, these results indicate that cell type-specific targets and binding sites can be extracted from RBFOX2-STAMP edit signatures by scRNA-seq within a mixture of heterogeneous cell types.

Example 6—Ribo-STAMP Reveals Translational Landscapes at Single-Cell Resolution To examine whether Ribo-STAMP can quantify ribosome association at the single-cell level, stable 72-hour high-induction control- and RPS2-STAMP was performed and scRNA-seq was conducted. To distinguish control- and RPS2-STAMP cell populations EPKM measurements were computed for protein coding genes for each cell. EPKM-based UMAP representation (FIG. 30A) followed by Louvain clustering (FIG. 30B) revealed a group of RPS2-STAMP (RPS2-population) cells that was clearly distinct from a population of background cells that contained a mixture of both control-STAMP and RPS2-STAMP cells (background-population). Focusing on this RPS2-population, it was shown that EPKM values (from CDS and 3'UTR) aggregated from the 3,917 single cells correlated meaningfully (R2=0.53) with genome-wide EPKM values from bulk Ribo-STAMP (FIG. 31A). EPKM values computed from edits within the combination of CDS and 3'UTR, versus only CDS regions, correlated very strongly (R2=0.81; FIG. 31B), therefore 3'UTR-derived edit measurements were not excluded. It was next addressed if aggregated single-cell Ribo-STAMP EPKM values can approximate ribosome-occupancy measurements derived from bulk poly-ribosome-fraction-enriched RNA (polysome-seq). RNA abundance measurements assessed for total mRNA from Ribo-STAMP and polysome-seq experiments were in good agreement and a positive relationship was observed (R2=0.54,FIG. 31C). Ribo-STAMP mRNA edits were then compared to polysome-seq mRNA abundance and less agreement between these measurements (R2=0.32, FIG. 31D) was observed, suggesting that Ribo-STAMP edit enrichment is not simply dictated by transcript levels. In contrast, poly-ribosome-fraction-enriched RNA measurements from polysome-seq were well correlated with Ribo-STAMP edits (R2=0.51, FIG. 32A), implying that single-cell Ribo-STAMP edit enrichments are more closely associated with ribosome occupancy than with transcript abundance. These results strongly indicate that single-cell Ribo-STAMP, like single-cell RBP-STAMP, recapitulates results from bulk experiments and correlates well with standard measurements from orthogonal bulk approaches.

Ribo-STAMP was next integrated with RBP-STAMP to define ribosome association and RBP binding sites in parallel after merging all control-, RBFOX2-, TIA1 and RPS2-STAMP single-cell edits matrices. UMAP visualization of single-cell, transcriptome-wide ε scores revealed that control-STAMP cells overlapped with a subpopulation of RBFOX2-, TIA1- and RPS2-STAMP cells (FIG. 33A), highlighting cells that have similar background-level edit patterns. Louvain clustering within UMAP projection space defined four distinct groups of single cells for downstream analysis: (i) RPS2-population cells (n=3,587 cells), (ii) RBFOX2-population cells (n=7,000 cells), containing the majority (92%) of RBFOX2 cells identified by capture sequencing, (iii) TIA1-population cells (n=1312 cells) containing the majority (57%) of TIA1 capture cells, and (iv) a background-population (n=20,655 cells), composed of control-STAMP cells and any cells that overlap spatially with control-STAMP cells (FIG. 32B, FIG. 33B). The ε score-derived RPS2-population was 84% matched to the EPKM-derived RPS2-population (FIG. 33C), and also had good EPKM value correlation with polysome-seq measurements (FIG. 34A). Metagene plotting of edits from these four subgroups for the top quartile of ribosome occupied genes (ribo-seq, n=4,931 genes) demonstrated CDS enrichment for single-cell RPS2-STAMP edits compared to more 3'UTR-centric enrichment for single-cell RBFOX2- and TIA1-STAMP (FIG. 34B), in agreement with results from bulk (FIG. 17A). Differential ε score analysis showed distinct editing signatures for RPS2-, RBFOX2- and TIA1-population cells compared to the background-population (FIG. 35A). To illustrate, the top 10 cells ranked by summed ε score exhibited the expected specific editing signatures on the RPL12, RPL30 and RPL23A target transcripts (FIG. 35B). These results highlight the capacity of STAMP to reveal RBP targets and ribosome association in parallel at single-cell resolution.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method for determining a relative translation rate of a target mRNA in a cell, as compared to a non-target mRNA, the method comprising:
    (a) introducing into the cell a chimeric protein comprising
        (i) a ribosomal protein consisting of RPS2 or RPS3 and
        (ii) an RNA editing protein;

(b) determining a plurality of nucleotide substitutions introduced into the target mRNA by the RNA editing protein; and (c) comparing the determined plurality of nucleotide substitutions introduced into the target mRNA to a plurality of nucleotide substitutions introduced into the non-target mRNA in the cell, thereby determining the relative translation rate of the target mRNA in the cell, as compared to the non-target mRNA.

2. The method of claim 1, wherein step (a) introducing into the cell the chimeric protein comprises introducing a nucleic acid encoding the chimeric protein.

3. The method of claim 2, wherein the nucleic acid is present in an expression vector, wherein the expression vector is a viral vector.

4. The method of claim 1, wherein the RNA editing protein is a cytidine deaminase or a fragment thereof.

5. The method of claim 4, wherein the cytidine deaminase is an apolipoprotein B mRNA editing enzyme, catalytic polypeptide-like (APOBEC) protein.

6. The method of claim 5, wherein the APOBEC protein is selected from the group consisting of: APOBEC1, APOBEC2, APOBEC3A, APOBEC3B, APOBEC3C, APOBEC3D, APOBEC3F, APOBEC3G, APOBEC3H, and APOBEC4.

7. The method of claim 1, wherein the RNA editing protein is an adenosine deaminase or a fragment thereof.

8. The method of claim 7, wherein the adenosine deaminase is an adenosine deaminase acting on RNA (ADAR).

9. The method of claim 7, wherein the adenosine deaminase is an adenosine aminohydrolase (ADA).

10. The method of claim 1, wherein step (b) comprises sequencing the target mRNA.

11. The method of claim 10, wherein the sequencing of the target mRNA is performed using single cell nucleic acid sequencing.

12. The method of claim 10, wherein the sequencing of the target mRNA is performed using long-read sequencing.

* * * * *